US011781122B2

(12) United States Patent
Louis et al.

(10) Patent No.: US 11,781,122 B2
(45) Date of Patent: Oct. 10, 2023

(54) ECTOINE-PRODUCING YEAST

(71) Applicant: ALDERYS, Orsay (FR)

(72) Inventors: Dominique Louis, Forges les Bains (FR); Karine Jaillardon, Saint Michel sur Orge (FR); Dominique Thomas, Gif sur Yvette (FR)

(73) Assignee: GIVAUDAN SA, Vernier (CH)

( * ) Notice: Subject to any disclaimer, the term of this patent is extended or adjusted under 35 U.S.C. 154(b) by 311 days.

(21) Appl. No.: 16/630,262

(22) PCT Filed: Jul. 10, 2018

(86) PCT No.: PCT/EP2018/068719
§ 371 (c)(1),
(2) Date: Jan. 10, 2020

(87) PCT Pub. No.: WO2019/011947
PCT Pub. Date: Jan. 17, 2019

(65) Prior Publication Data
US 2021/0222136 A1 Jul. 22, 2021

(30) Foreign Application Priority Data
Jul. 11, 2017 (EP) ..................... 17305910

(51) Int. Cl.
| | |
|---|---|
| *C12N 9/12* | (2006.01) |
| *C12N 9/04* | (2006.01) |
| *C12N 9/02* | (2006.01) |
| *C12N 9/10* | (2006.01) |
| *C12N 9/80* | (2006.01) |
| *C12N 9/88* | (2006.01) |
| *C12P 17/12* | (2006.01) |

(52) U.S. Cl.
CPC ......... *C12N 9/1217* (2013.01); *C12N 9/0006* (2013.01); *C12N 9/0008* (2013.01); *C12N 9/1029* (2013.01); *C12N 9/1096* (2013.01); *C12N 9/80* (2013.01); *C12N 9/88* (2013.01); *C12P 17/12* (2013.01); *C12Y 101/01003* (2013.01); *C12Y 102/01011* (2013.01); *C12Y 203/01031* (2013.01); *C12Y 203/01178* (2013.01); *C12Y 206/01076* (2013.01); *C12Y 207/02004* (2013.01); *C12Y 402/01108* (2013.01)

(58) Field of Classification Search
None
See application file for complete search history.

(56) References Cited

U.S. PATENT DOCUMENTS

2007/0087403 A1* 4/2007 Bestel-Corre ......... C12P 13/005
 435/254.2
2019/0264245 A1* 8/2019 Haas ....................... C12P 13/06

FOREIGN PATENT DOCUMENTS

| CN | 106318917 A | * | 1/2017 | .......... C12N 9/0008 |
|---|---|---|---|---|
| DE | 1999 25 615 A1 | | 12/2000 | |
| EP | 2 743 350 A1 | | 6/2014 | |

OTHER PUBLICATIONS

Ning et al., Pathway construction and metabolic engineering for fermentative production of ectoine in *Escherichia coli*, Metabolic Eng. 36, 2016, 10-18. (Year: 2016).*
Eijsink et al., Rational engineering of enzyme stability, J. Biotechnol. 113, 2004, 105-20. (Year: 2004).*
Tun et al., Effects of metal ions and hydrogen peroxide on the phenotype of yeast hom6Δ mutant, Lett. Appl. Microbiol. 60, 2014, 20-26. (Year: 2014).*
Uniprot, Accession No. W1Q994, 2016, www.uniprot.org. (Year: 2016).*
Celik et al., Production of recombinant proteins by yeast cells, Biotechnol. Adv. 30, 2012, 1108-18 (Year: 2012).*
Asadollahi et al., Enhancing sesquiterpene production in *Saccharomyces cerevisiae* through in silico driven metabolic engineering, Metabolic Eng. 11, 2009, 328-334. (Year: 2009).*
Farfan et al., Threonine Overproduction in Yeast Strains Carrying the HOM3-R2 Mutant Allele under the Control of Different Inducible Promoters, Appl. Environ. Microbiol. 65, 1999, 110-16. (Year: 1999).*
Jain et al., Elimination of glycerol and replacement with alternative products in ethanol fermentation by *Saccharomyces cerevisiae*, J. Ind. Microbiol. Biotechnol. 38, 2011, 1427-35. (Year: 2011).*
He et al: "High production of ectoine from aspartate and glycerol by use of whole-cell biocatalysis in recombinant *Escherichia coli*", Microbial Cell Ractories, vol. 14, No. 55 pp. 1-10, Apr. 15, 2015.
Stoveken et al: "A Specialized Aspartokinase Enhances the Biosynthesis of the Osmoprotectants Ectoine and Hydroxyectoine in Pseudomonas stutzeriA1501", Journal of Bacteriology, vol. 193, No. 17, Jul. 1, 2011.
Bestvater et al: "Heterologous ectoine production of *Escherichia coli*: By-passing the metabolic bottle-neck", Saline Systems, Biomed Central, London, GB, vol. 4, No. 1, p. 12, Aug. 29, 2008.
Kunte et al: "Industrial production of the cell protectant ectoine: Protection mechanisms, processes, and products", Current Biotechnology 2014 Bentham Science Publishers B.V. NLD, vol. 3, No. 1 pp. 10-25, 2014.
Lentzen et al: "Extremolytes: natural compounds form extremophiles for versatile applications", Appl Microbiol Biotechnol, vol. 72, pp. 623-634, 2006.

(Continued)

*Primary Examiner* — Todd M Epstein
(74) *Attorney, Agent, or Firm* — WCF IP

(57) ABSTRACT

The present invention relates to the field of bio-production of ectoine. There is a need in the art for ectoine production methods allowing its highly efficient synthesis and secretion. The solution proposed in the present invention is the use of a genetically modified yeast comprising many modifications as described in the present text.

15 Claims, No Drawings
Specification includes a Sequence Listing.

(56) References Cited

OTHER PUBLICATIONS

Graf et al: "The multifunctional role of ectoine as a natural cell protectant", Clinics in Dermatology, vol. 26, pp. 326-333, 2008.
Ono et al., "Characterization of Biosynthetic Enzymes for Ectoine as a Compatible Solute in a Moderately Halophilic Eubacterium, Halomonas elongata", Journal of Bacteriology, Jan. 1999, vol. 181, No. 1, p. 91-99.

\* cited by examiner

SEQUENCE LISTING

<160> NUMBER OF SEQ ID NOS: 121

<210> SEQ ID NO 1
<211> LENGTH: 1583
<212> TYPE: DNA
<213> ORGANISM: Saccharomyces cerevisiae
<220> FEATURE:
<223> OTHER INFORMATION: ASPARTOKINASE (HOM3)
<220> FEATURE:
<223> OTHER INFORMATION: ASPARTOKINASE (HOM3)

<400> SEQUENCE: 1

```
atgccaatgg atttccaacc tacatcaagt cattcgaact gggtcgtgca aaagttcggt      60
ggtacatctg tcggtaaatt tcccgtccaa atagtggatg acattgtgaa gcactattct     120
aaacctgacg gcccaaacaa taatgtcgct gtcgtttgtt ccgcccgttc ttcatacacc     180
aaggctgaag gtaccacttc tcgtcttttg aaatgttgtg atttggcttc gcaagaatct     240
gaatttcaag acattatcga agttatcaga caagaccata tcgataatgc cgaccgcttc     300
attctcaatc ctgccttgca agccaagtta gtggatgata ccaataaaga acttgaactg     360
gtcaagaaat atttaaatgc ttcaaaagtt ttgggtgaag tgagttcacg tacagtagat     420
ctggtgatgt catgtggtga agttgagt tgtttgttca tgactgcttt atgtaatgac      480
cgtggctgta aggccaaata tgtggatttg agccacattg ttccctctga tttcagtgcc     540
agcgctttgg ataacagttt ctacactttc ctggttcaag cattgaaaga aaaattggcc     600
ccctttgtaa gtgctaaaga gcgtatcgtt ccagtcttta caggttttt tggtttagtt      660
ccaactggtc ttctgaatgg tgttggtcgt ggctataccg atttatgtgc cgctttgata     720
gcagttgctg taaatgctga tgaactacaa gtttggaagg aagttgatgg tatatttact     780
gctgatcctc gtaaggttcc tgaagcacgt ttgctagaca gtgttactcc agaagaagct     840
tctgaattaa catattatgg ttccgaagtt atacatcctt ttacgatgga acaagttatt     900
agggctaaga ttcctattag aatcaagaat gttcaaaatc cattaggtaa cggtaccatt     960
atctacccag ataatgtagc aaagaagggg gaatctactc caccacatcc tcctgagaac    1020
ttatcctcat ctttctatga aaagagaaag agaggtgcca ctgctatcac caccaaaaat    1080
gacatttttcg tcatcaacat tcattccaat aagaaaaccc tatcccatgg tttcctagct    1140
caaatattta ccatcctgga taagtacaag ttagtcgtag atttaatatc tacttctgaa    1200
gttcatgttt cgatggcttt gcccattcca gatgcagact cattaaaatc tctgagacaa    1260
gctgaggaaa aattgagaat tttaggttct gttgatatca caagaagtt gtctattgtt     1320
tcattagttg gtaaacatat gaaacaatac atcggcattg ctggtaccat gtttactact    1380
cttgctgaag aaggcatcaa cattgaaatg atttctcaag gggcaaatga aataaacata    1440
tcctgcgtta tcaatgaatc tgactccata aaagcgctac aatgtattca tgccaagtta    1500
ctaagtgagc ggacaaatac ttcaaaccaa tttgaacatg ccattgatga acgtttagaa    1560
caattgaaaa gacttggaat taa                                            1583
```

<210> SEQ ID NO 2
<211> LENGTH: 526
<212> TYPE: PRT
<213> ORGANISM: Saccharomyces cerevisiae
<220> FEATURE:
<223> OTHER INFORMATION: ASPARTOKINASE (HOM3)
<220> FEATURE:
<223> OTHER INFORMATION: ASPARTOKINASE (HOM3)

<400> SEQUENCE: 2

```
Pro Met Asp Phe Gln Pro Thr Ser Ser His Ser Asn Trp Val Val Gln
1               5                   10                  15

Lys Phe Gly Gly Thr Ser Val Gly Lys Phe Pro Val Gln Ile Val Asp
            20                  25                  30

Asp Ile Val Lys His Tyr Ser Lys Pro Asp Gly Pro Asn Asn Asn Val
        35                  40                  45

Ala Val Val Cys Ser Ala Arg Ser Ser Tyr Thr Lys Ala Glu Gly Thr
    50                  55                  60

Thr Ser Arg Leu Leu Lys Cys Cys Asp Leu Ala Ser Gln Glu Ser Glu
65                  70                  75                  80

Phe Gln Asp Ile Ile Glu Val Ile Arg Gln Asp His Ile Asp Asn Ala
                    85                  90                  95

Asp Arg Phe Ile Leu Asn Pro Ala Leu Gln Ala Lys Leu Val Asp Asp
                100                 105                 110

Thr Asn Lys Glu Leu Glu Leu Val Lys Lys Tyr Leu Asn Ala Ser Lys
        115                 120                 125

Val Leu Gly Glu Val Ser Ser Arg Thr Val Asp Leu Val Met Ser Cys
    130                 135                 140

Gly Glu Lys Leu Ser Cys Leu Phe Met Thr Ala Leu Cys Asn Asp Arg
145                 150                 155                 160

Gly Cys Lys Ala Lys Tyr Val Asp Leu Ser His Ile Val Pro Ser Asp
                165                 170                 175

Phe Ser Ala Ser Ala Leu Asp Asn Ser Phe Tyr Thr Phe Leu Val Gln
                180                 185                 190

Ala Leu Lys Glu Lys Leu Ala Pro Phe Val Ser Ala Lys Glu Arg Ile
        195                 200                 205

Val Pro Val Phe Thr Gly Phe Phe Gly Leu Val Pro Thr Gly Leu Leu
    210                 215                 220

Asn Gly Val Gly Arg Gly Tyr Thr Asp Leu Cys Ala Ala Leu Ile Ala
225                 230                 235                 240

Val Ala Val Asn Ala Asp Glu Leu Gln Val Trp Lys Glu Val Asp Gly
                245                 250                 255

Ile Phe Thr Ala Asp Pro Arg Lys Val Pro Glu Ala Arg Leu Leu Asp
                260                 265                 270

Ser Val Thr Pro Glu Glu Ala Ser Glu Leu Thr Tyr Tyr Gly Ser Glu
        275                 280                 285

Val Ile His Pro Phe Thr Met Glu Gln Val Ile Arg Ala Lys Ile Pro
    290                 295                 300

Ile Arg Ile Lys Asn Val Gln Asn Pro Leu Gly Asn Gly Thr Ile Ile
305                 310                 315                 320

Tyr Pro Asp Asn Val Ala Lys Lys Gly Glu Ser Thr Pro Pro His Pro
                325                 330                 335

Pro Glu Asn Leu Ser Ser Ser Phe Tyr Glu Lys Arg Lys Arg Gly Ala
                340                 345                 350

Thr Ala Ile Thr Thr Lys Asn Asp Ile Phe Val Ile Asn Ile His Ser
        355                 360                 365

Asn Lys Lys Thr Leu Ser His Gly Phe Leu Ala Gln Ile Phe Thr Ile
    370                 375                 380

Leu Asp Lys Tyr Lys Leu Val Asp Leu Ile Ser Thr Ser Glu Val
385                 390                 395                 400

His Val Ser Met Ala Leu Pro Ile Pro Asp Ala Asp Ser Leu Lys Ser
                405                 410                 415
```

Leu Arg Gln Ala Glu Glu Lys Leu Arg Ile Leu Gly Ser Val Asp Ile
            420                 425                 430

Thr Lys Lys Leu Ser Ile Val Ser Leu Val Gly Lys His Met Lys Gln
                435                 440                 445

Tyr Ile Gly Ile Ala Gly Thr Met Phe Thr Thr Leu Ala Glu Glu Gly
        450                 455                 460

Ile Asn Ile Glu Met Ile Ser Gln Gly Ala Asn Glu Ile Asn Ile Ser
465                 470                 475                 480

Cys Val Ile Asn Glu Ser Asp Ser Ile Lys Ala Leu Gln Cys Ile His
                485                 490                 495

Ala Lys Leu Leu Ser Glu Arg Thr Asn Thr Ser Asn Gln Phe Glu His
        500                 505                 510

Ala Ile Asp Glu Arg Leu Glu Gln Leu Lys Arg Leu Gly Ile
        515                 520                 525

<210> SEQ ID NO 3
<211> LENGTH: 1215
<212> TYPE: DNA
<213> ORGANISM: Bacillus subtilis
<220> FEATURE:
<223> OTHER INFORMATION: ASPARTATE KINASE (AK)
<220> FEATURE:
<223> OTHER INFORMATION: ASPARTATE KINASE (AK)

<400> SEQUENCE: 3
atggctatta tcgtccaaaa attcggagga actagcgtta aggatgacaa agggagaaag      60
ttggccttag gcacattaa ggaggcaatt cagagggtt ataaggtggt tgtagttgta       120
tcggctatgg gtagaaaagg ggaccctac gcgacggact cactattggg tttactttac     180
ggggatcaat cagcaatcag cccaagagag caggatctgc tgctatcatg tggagaaacc    240
atatcctcgg ttgtgttcac cagcatgtta ttagataatg gagtaaaagc agcagccctg    300
acgggagccc aggctggttt tttaaccaac gatcagcata ctaatgcaaa aattatagag    360
atgaagcctg aacgtctttt cagtgttctt gcaaaccacg acgcagttgt cgtcgctgga    420
tttcagggcg ctaccgagaa aggagatact accacaatcg gtagaggtgg ctcggacacg    480
tcagctgcag ccctaggtgc tgctgttgat gcagagtaca tagatatctt tactgacgta    540 gaagggtga tgaccgcaga tccaagagta gtagaaaatg caaagccact accagtggta    600
acttataccg aaatctgcaa cttggcttac caaggtgcta aggtaatatc tccaagagct    660
gtggaaattg ctatgcaagc aaaggttcct atccgtgtta ggagtactta ttcaaacgat    720
aaaggtacgt tagtaactag tcatcatagt tccaaagttg gctctgacgt ctttgaaagg    780
ttaatcactg gtatcgcaca tgttaaagac gtcactcaat tcaaggtccc ggcgaaaata    840
ggtcaatata acgttcaaac agaagtgttt aaagcgatgg cgaatgccgg tatatctgtc    900
gatttcttta atattacacc ctctgaaata gtatatacag tcgcgggtaa taagactgaa    960
acagctcaaa ggattttgat ggatatgggc tatgatccta tggtcacaag aaattgtgcc   1020
aaggtgtctg ccgtgggtgc tggcattatg ggtgtcccag gtgtgacatc gaaaattgtt   1080
tctgccttat ctgaaaaaga aattccgatt ttgcaatctg ctgattccca tacaacaatt   1140
tgggttttgg ttcatgaagc cgatatggtt cctgctgtta atgccttgca cgaagttttt   1200
gaattgtcca ataa                                                      1215

<210> SEQ ID NO 4
<211> LENGTH: 404
<212> TYPE: PRT

```
<213> ORGANISM: Bacillus subtilis
<220> FEATURE:
<223> OTHER INFORMATION: ASPARTATE KINASE (AK)
<220> FEATURE:
<223> OTHER INFORMATION: ASPARTATE KINASE (AK)

<400> SEQUENCE: 4
```

Met Ala Ile Ile Val Gln Lys Phe Gly Gly Thr Ser Val Lys Asp Asp
1               5                   10                  15

Lys Gly Arg Lys Leu Ala Leu Gly His Ile Lys Glu Ala Ile Ser Glu
            20                  25                  30

Gly Tyr Lys Val Val Val Val Ser Ala Met Gly Arg Lys Gly Asp
        35                  40                  45

Pro Tyr Ala Thr Asp Ser Leu Leu Gly Leu Leu Tyr Gly Asp Gln Ser
50                  55                  60

Ala Ile Ser Pro Arg Glu Gln Asp Leu Leu Ser Cys Gly Glu Thr
65                  70                  75                  80

Ile Ser Ser Val Val Phe Thr Ser Met Leu Leu Asp Asn Gly Val Lys
                85                  90                  95

Ala Ala Ala Leu Thr Gly Ala Gln Ala Gly Phe Leu Thr Asn Asp Gln
            100                 105                 110

His Thr Asn Ala Lys Ile Ile Glu Met Lys Pro Glu Arg Leu Phe Ser
        115                 120                 125

Val Leu Ala Asn His Asp Ala Val Val Val Ala Gly Phe Gln Gly Ala
130                 135                 140

Thr Glu Lys Gly Asp Thr Thr Thr Ile Gly Arg Gly Gly Ser Asp Thr
145                 150                 155                 160

Ser Ala Ala Ala Leu Gly Ala Ala Val Asp Ala Glu Tyr Ile Asp Ile
                165                 170                 175

Phe Thr Asp Val Glu Gly Val Met Thr Ala Asp Pro Arg Val Val Glu
            180                 185                 190

Asn Ala Lys Pro Leu Pro Val Val Thr Tyr Thr Glu Ile Cys Asn Leu
        195                 200                 205

Ala Tyr Gln Gly Ala Lys Val Ile Ser Pro Arg Ala Val Glu Ile Ala
210                 215                 220

Met Gln Ala Lys Val Pro Ile Arg Val Arg Ser Thr Tyr Ser Asn Asp
225                 230                 235                 240

Lys Gly Thr Leu Val Thr Ser His His Ser Ser Lys Val Gly Ser Asp
                245                 250                 255

Val Phe Glu Arg Leu Ile Thr Gly Ile Ala His Val Lys Asp Val Thr
            260                 265                 270

Gln Phe Lys Val Pro Ala Lys Ile Gly Gln Tyr Asn Val Gln Thr Glu
        275                 280                 285

Val Phe Lys Ala Met Ala Asn Ala Gly Ile Ser Val Asp Phe Phe Asn
290                 295                 300

Ile Thr Pro Ser Glu Ile Val Tyr Thr Val Ala Gly Asn Lys Thr Glu
305                 310                 315                 320

Thr Ala Gln Arg Ile Leu Met Asp Met Gly Tyr Asp Pro Met Val Thr
                325                 330                 335

Arg Asn Cys Ala Lys Val Ser Ala Val Gly Ala Gly Ile Met Gly Val
            340                 345                 350

Pro Gly Val Thr Ser Lys Ile Val Ser Ala Leu Ser Glu Lys Glu Ile
        355                 360                 365

Pro Ile Leu Gln Ser Ala Asp Ser His Thr Thr Ile Trp Val Leu Val
370                 375                 380

His Glu Ala Asp Met Val Pro Ala Val Asn Ala Leu His Glu Val Phe
385                 390                 395                 400

Glu Leu Ser Lys

<210> SEQ ID NO 5
<211> LENGTH: 1098
<212> TYPE: DNA
<213> ORGANISM: Saccharomyces cerevisiae
<220> FEATURE:
<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 5

```
atggctggaa agaaaattgc tggtgttttg ggtgctactg gttccgttgg tcaacgtttc      60
attctgttgt tggcaaatca ccctcatttc gaactgaaag ttcttggtgc ctcttctaga     120
tcagctggca agaaatacgt tgacgctgtg aactggaagc aaaccgattt gctaccggaa     180
tctgctaccg atattattgt ttccgaatgt aaatctgaat tctttaaaga gtgtgacatc     240
gtcttttccg gattggatgc tgactatgct ggcgctatcg aaaaggaatt catggaagct     300
ggtatcgcca ttgtttccaa tgccaagaat tatagaagag aacaagatgt gccattgatt     360
gttcctgttg tcaatcctga gcatttggat attgtagctc aaaagcttga caccgccaag     420
gctcaaggta agccaagacc agggttcatt atctgtattt ccaattgttc cactgcaggt     480
ttggttgcac cattgaagcc tttgattgaa aaattcggtc ctattgatgc tttgaccact     540
actactttgc aagcaatctc aggtgctggt ttctccccag tgtaccagg tattgatatt     600
ctagacaata ttattccata cattggtggt gaagaagaca agatggaatg ggagaccaag     660
aaaatcttgg ctccattagc agaagacaag acacacgtca aactattgac tccagaagaa     720
atcaaagtct ctgctcaatg taacagagtc gctgttttcc gatgggcaca cgaatgtatc     780
tctttgaggt tcaagaacag acctgctcca tccgtcgagc aagtcaagac atgcctaaaa     840
gaatacgtct gcgatgccta caaattaggc tgtcattctg ctccaaagca aactattcat     900
gttttggaac aaccagacag acctcaacca aggttggaca ggaacagaga cagcggttac     960
ggtgttttccg ttggtagaat cagagaagac ccattgttag atttcaaaat ggttgtcctt    1020
tcccacaaca ccattattgg tgccgctggt tctggtgtct tgattgccga atcttacta     1080
gcaagaaact tgatttaa                                                  1098
```

<210> SEQ ID NO 6
<211> LENGTH: 1098
<212> TYPE: DNA
<213> ORGANISM: Saccharomyces cerevisiae
<220> FEATURE:
<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 6

```
atggctggaa agaaaattgc tggtgttttg ggtgctactg gttccgttgg tcaacgtttc      60
attctgttgt tggcaaatca ccctcatttc gaactgaaag ttcttggtgc ctctgagaga    120
tcagctggca agaaatacgt tgacgctgtg aactggaagc aaaccgattt gctaccggaa     180
tctgctaccg atattattgt ttccgaatgt aaatctgaat tctttaaaga gtgtgacatc     240
gtcttttccg gattggatgc tgactatgct ggcgctatcg aaaaggaatt catggaagct     300
ggtatcgcca ttgtttccaa tgccaagaat tatagaagag aacaagatgt gccattgatt     360
```

```
gttcctgttg tcaatcctga gcatttggat attgtagctc aaaagcttga caccgccaag    420
gctcaaggta agccaagacc agggttcatt atctgtattt ccaattgttc cactgcaggt    480
ttggttgcac cattgaagcc tttgattgaa aaattcggtc ctattgatgc tttgaccact    540
actactttgc aagcaatctc aggtgctggt ttctccccag gtgtaccagg tattgatatc    600
ctagacaata ttattccata cattggtggt gaagaagaca agatggaatg ggagaccaag    660
aaaatcttgg ctccattagc agaagacaag acacacgtca aactattgac tccagaagaa    720
atcaaagtct ctgctcaatg taacagagtc gctgtttccg atgggcacac cgaatgtatc    780
tctttgaggt tcaagaacag acctgctcca tccgtcgagc aagtcaagac atgcctaaaa    840
gaatacgtct gcgatgccta caaattaggc tgtcattctg ctccaaagca aactattcat    900
gttttggaac aaccagacag acctcaacca aggttggaca ggaacagaga cagcggttac    960
ggtgtttccg ttggtagaat cagagaagac ccattgttag atttcaaaat ggttgtcctt   1020
tcccacaaca ccattattgg tgccgctggt tctggtgtct tgattgccga aatcttacta   1080
gcaagaaact tgatttaa                                                 1098
```

<210> SEQ ID NO 7
<211> LENGTH: 365
<212> TYPE: PRT
<213> ORGANISM: Saccharomyces cerevisiae
<220> FEATURE:
<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 7

```
Met Ala Gly Lys Lys Ile Ala Gly Val Leu Gly Ala Thr Gly Ser Val
1               5                   10                  15

Gly Gln Arg Phe Ile Leu Leu Leu Ala Asn His Pro His Phe Glu Leu
            20                  25                  30

Lys Val Leu Gly Ala Ser Ser Arg Ser Ala Gly Lys Lys Tyr Val Asp
        35                  40                  45

Ala Val Asn Trp Lys Gln Thr Asp Leu Leu Pro Glu Ser Ala Thr Asp
    50                  55                  60

Ile Ile Val Ser Glu Cys Lys Ser Glu Phe Phe Lys Glu Cys Asp Ile
65                  70                  75                  80

Val Phe Ser Gly Leu Asp Ala Asp Tyr Ala Gly Ala Ile Glu Lys Glu
                85                  90                  95

Phe Met Glu Ala Gly Ile Ala Ile Val Ser Asn Ala Lys Asn Tyr Arg
            100                 105                 110

Arg Glu Gln Asp Val Pro Leu Ile Val Pro Val Val Asn Pro Glu His
        115                 120                 125

Leu Asp Ile Val Ala Gln Lys Leu Asp Thr Ala Lys Ala Gln Gly Lys
    130                 135                 140

Pro Arg Pro Gly Phe Ile Ile Cys Ile Ser Asn Cys Ser Thr Ala Gly
145                 150                 155                 160

Leu Val Ala Pro Leu Lys Pro Leu Ile Glu Lys Phe Gly Pro Ile Asp
                165                 170                 175

Ala Leu Thr Thr Thr Thr Leu Gln Ala Ile Ser Gly Ala Gly Phe Ser
            180                 185                 190

Pro Gly Val Pro Gly Ile Asp Ile Leu Asp Asn Ile Ile Pro Tyr Ile
        195                 200                 205

Gly Gly Glu Glu Asp Lys Met Glu Trp Glu Thr Lys Lys Ile Leu Ala
```

```
                210                 215                 220
Pro Leu Ala Glu Asp Lys Thr His Val Lys Leu Leu Thr Pro Glu Glu
225                 230                 235                 240

Ile Lys Val Ser Ala Gln Cys Asn Arg Val Ala Val Ser Asp Gly His
                245                 250                 255

Thr Glu Cys Ile Ser Leu Arg Phe Lys Asn Arg Pro Ala Pro Ser Val
            260                 265                 270

Glu Gln Val Lys Thr Cys Leu Lys Glu Tyr Val Cys Asp Ala Tyr Lys
        275                 280                 285

Leu Gly Cys His Ser Ala Pro Lys Gln Thr Ile His Val Leu Glu Gln
    290                 295                 300

Pro Asp Arg Pro Gln Pro Arg Leu Asp Arg Asn Arg Asp Ser Gly Tyr
305                 310                 315                 320

Gly Val Ser Val Gly Arg Ile Arg Glu Asp Pro Leu Leu Asp Phe Lys
                325                 330                 335

Met Val Val Leu Ser His Asn Thr Ile Ile Gly Ala Ala Gly Ser Gly
            340                 345                 350

Val Leu Ile Ala Glu Ile Leu Leu Ala Arg Asn Leu Ile
        355                 360                 365

<210> SEQ ID NO 8
<211> LENGTH: 1413
<212> TYPE: DNA
<213> ORGANISM: Pseudomonas aeruginosa
<220> FEATURE:
<223> OTHER INFORMATION: DIAMINOBUTYRATE AMINOTRANSFERASE (EctB)
<220> FEATURE:
<223> OTHER INFORMATION: DIAMINOBUTYRATE AMINOTRANSFERASE (EctB)

<400> SEQUENCE: 8
atggctcacg ttgctacatc agttatcgag gaccaaccct acgcgccac tcccgcagaa       60 ggcgagactc tgtacgagtt ctcccaatct cctctcttag aacgtcagtc tcgccaagag      120
agcaatgctc gaagctatcc acgtagaata ccacttgcat taaagaaggc ccgaggtctg      180
ctagtggaag acgtcgaagg gaggactttc attgactgtc tcgccggtgc aggaacccta      240
gcattgggac ataatcaccc ggtagttata gaagccatta gacaggttct tgctgatgaa      300
ttgcccttgc acaccttaga tttgacgacc cctgtgaagg accaattcgt ccaggattta      360
tttgggttgc tcccacctgc tttggcagcg aagccaaga tccaattctg tgggccaaca      420
ggaacagacg cagttgaggc cgctcttaag cttgtgcgga cggcgactgg ccgttctaca      480
atactaagtt ttcaaggagg atatcacgga atgtcccaag gtgcactggg cttgatgggc      540
aacctcggtc caaagaagcc attgggcgca gtactctcaa ccggcgtcca attcctccca      600
tacccgtacg attacagatg tccattcggt ctgggtggcg aagctggagt caaggcgaat      660
ctacattact tagaaaattt gctcaatgat cctgaaggag gtgtacaatt gccggccgct      720
gtcattgttg aagttgtaca aggcgaaggt ggggtcgtgc cagcagattt ggactggtta      780
cgaggattac gtaggattac tgagcaggcc ggtgtagccc ttattgtgga tgaaattcaa      840
tccggctttg cgcgtactgg tcggatgttc gcctttgagc atgccggcat cgtgcctgat      900
gtggtagtgc tttccaaagc tatcggtggc tccctccctt tagctgtggt cgtatatcgg      960
gaatggctag acaagtggca acctggggca catgctggaa ccttcagagg caatcagatg     1020
gcgatggcag ctggcagtgc agtcatgaga tacctaaaag agcatgatct ggcagcccat     1080
gcagccgcca tgggcgaacg actagctgag catctcagga tcttgcagag agactatccg     1140
```

```
cagttaggtg atatacgagg ccgcggctta atgttaggtg tcgagatagt agatccgcag   1200
ggcgaagctg acgctctagg tcatccaccc actgacggag ccctggcctc gcgggtacaa   1260
cgggaatgtt tgagaagagg tctcatattg gaattaggcg ggcgacacgg atctgttgta   1320
agattcttgc cacctttgat tattggggca gaacagatag acgaagtggc gcgtagattt   1380
gccagggcat taggagctgc ccttgctggg taa                                1413

<210> SEQ ID NO 9
<211> LENGTH: 1266
<212> TYPE: DNA
<213> ORGANISM: Halomonas elongata
<220> FEATURE:
<223> OTHER INFORMATION: DIAMINOBUTYRATE AMINOTRANSFERASE (EctB)
<220> FEATURE:
<223> OTHER INFORMATION: DIAMINOBUTYRATE AMINOTRANSFERASE (EctB)

<400> SEQUENCE: 9
atgcagacac aaatcttgga acgtatggaa tccgacgtca gaacgtactc aagatctttc     60
cctgtagtct ttaccaaggc gcgaaatgct cgacttaccg acgaagaagg gcgagagtac   120
atagacttcc tagcaggcgc tggtacgcta aattatgggc ataacaatcc acacctgaag   180
caagcattac tcgactacat tgattcagac ggcattgtcc atggtctgga tttctggacc   240
gcggcaaagc gcgattacct tgagacactc gaagaggtca ttttgaaacc gcgtggtttg   300
gactataagg ttcacttacc gggcccaacg ggcaccaatg cagttgaagc cgccattcgt   360
ttggccaggg tcgccaaagg tcgtcataat attgtctctt ttacaaatgg ctttcacggt   420
gttactatgg gcgctctggc gacgaccggt aacagaaagt tcgggaagc acaggtggc     480 gtccctactc aggcagcgag cttcatgcca tttgacgggt atcttggctc ttccactgat   540
acacttgatt acttcgaaaa gttattgggt gataagtcag gtgggcttga tgtgccagcc   600
gcggtaatag ttgaaacagt ccaaggagaa ggcggaataa acgttgcggg acttgagtgg   660
ctcaagagat tagaaagcat tgtagagca atgatatttt tgttaatcat cgatgatata   720
caagccggct gcggaagaac tggaaagttc ttctcattcg aacatgctgg tattactcct   780
gatattgtca caaactcgaa atcttttgtca ggatatggtt tgccctttgc tcatgtgctt   840
atgagaccgg agcttgataa atggaaacca ggacaatata cggaacatt ccggggtttc    900 aatctagctt tcgcgaccgc tgctgcagca atgaggaaat actggtcgga cgatacgttt   960
gaacgagacg ttcaaaggaa agctagaata gttgaggaaa gatttggtaa atcgcagct   1020 tggcttttctg aaaacggtat tgaagcttcc gaacggggta ggggtttgat gagaggtatc 1080
gacgttggtt ctggggacat agcagataaa attacgcatc aagcgtttga aaatggttta 1140
atcatcgaaa caagtggtca agatggtgag gttgttaaat gcttatgccc cttaaccata   1200
ccagatgaag atttagtaga aggtttagac atattagaaa ctagcacaaa acaagccttc   1260
tcttaa                                                                1266

<210> SEQ ID NO 10
<211> LENGTH: 470
<212> TYPE: PRT
<213> ORGANISM: Pseudomonas aeruginosa
<220> FEATURE:
<223> OTHER INFORMATION: DIAMINOBUTYRATE AMINOTRANSFERASE (EctB)
<220> FEATURE:
<223> OTHER INFORMATION: DIAMINOBUTYRATE AMINOTRANSFERASE (EctB)

<400> SEQUENCE: 10

Met Ala His Val Ala Thr Ser Val Ile Glu Asp Gln Pro Leu Arg Ala
```

```
1               5                   10                  15
Thr Pro Ala Glu Gly Glu Thr Leu Tyr Glu Phe Ser Gln Ser Pro Leu
                20                  25                  30

Leu Glu Arg Gln Ser Arg Gln Glu Ser Asn Ala Arg Ser Tyr Pro Arg
                35                  40                  45

Arg Ile Pro Leu Ala Leu Lys Lys Ala Arg Gly Leu Leu Val Glu Asp
50                          55                  60

Val Glu Gly Arg Thr Phe Ile Asp Cys Leu Ala Gly Ala Gly Thr Leu
65                  70                  75                  80

Ala Leu Gly His Asn His Pro Val Val Ile Glu Ala Ile Arg Gln Val
                    85                  90                  95

Leu Ala Asp Glu Leu Pro Leu His Thr Leu Asp Leu Thr Thr Pro Val
                100                 105                 110

Lys Asp Gln Phe Val Gln Asp Leu Phe Gly Leu Leu Pro Pro Ala Leu
                115                 120                 125

Ala Ala Glu Ala Lys Ile Gln Phe Cys Gly Pro Thr Gly Thr Asp Ala
            130                 135                 140

Val Glu Ala Ala Leu Lys Leu Val Arg Thr Ala Thr Gly Arg Ser Thr
145                 150                 155                 160

Ile Leu Ser Phe Gln Gly Gly Tyr His Gly Met Ser Gln Gly Ala Leu
                165                 170                 175

Gly Leu Met Gly Asn Leu Gly Pro Lys Lys Pro Leu Gly Ala Val Leu
                180                 185                 190

Ser Thr Gly Val Gln Phe Leu Pro Tyr Pro Tyr Asp Tyr Arg Cys Pro
                195                 200                 205

Phe Gly Leu Gly Gly Glu Ala Gly Val Lys Ala Asn Leu His Tyr Leu
210                     215                 220

Glu Asn Leu Leu Asn Asp Pro Glu Gly Gly Val Gln Leu Pro Ala Ala
225                 230                 235                 240

Val Ile Val Glu Val Val Gln Gly Glu Gly Gly Val Val Pro Ala Asp
                245                 250                 255

Leu Asp Trp Leu Arg Gly Leu Arg Arg Ile Thr Glu Gln Ala Gly Val
            260                 265                 270

Ala Leu Ile Val Asp Glu Ile Gln Ser Gly Phe Ala Arg Thr Gly Arg
            275                 280                 285

Met Phe Ala Phe Glu His Ala Gly Ile Val Pro Asp Val Val Val Leu
            290                 295                 300

Ser Lys Ala Ile Gly Gly Ser Leu Pro Leu Ala Val Val Val Tyr Arg
305                 310                 315                 320

Glu Trp Leu Asp Lys Trp Gln Pro Gly Ala His Ala Gly Thr Phe Arg
                325                 330                 335

Gly Asn Gln Met Ala Met Ala Ala Gly Ser Ala Val Met Arg Tyr Leu
                340                 345                 350

Lys Glu His Asp Leu Ala Ala His Ala Ala Met Gly Glu Arg Leu
                355                 360                 365

Ala Glu His Leu Arg Ile Leu Gln Arg Asp Tyr Pro Gln Leu Gly Asp
                370                 375                 380

Ile Arg Gly Arg Gly Leu Met Leu Gly Val Glu Ile Val Asp Pro Gln
385                 390                 395                 400

Gly Glu Ala Asp Ala Leu Gly His Pro Pro Thr Asp Gly Ala Leu Ala
                405                 410                 415

Ser Arg Val Gln Arg Glu Cys Leu Arg Arg Gly Leu Ile Leu Glu Leu
                420                 425                 430
```

```
Gly Gly Arg His Gly Ser Val Val Arg Phe Leu Pro Pro Leu Ile Ile
        435                 440                 445

Gly Ala Glu Gln Ile Asp Glu Val Ala Arg Arg Phe Ala Arg Ala Leu
    450                 455                 460

Gly Ala Ala Leu Ala Gly
465                 470

<210> SEQ ID NO 11
<211> LENGTH: 421
<212> TYPE: PRT
<213> ORGANISM: Halomonas elongata
<220> FEATURE:
<223> OTHER INFORMATION: DIAMINOBUTYRATE AMINOTRANSFERASE (EctB)
<220> FEATURE:
<223> OTHER INFORMATION: DIAMINOBUTYRATE AMINOTRANSFERASE (EctB)

<400> SEQUENCE: 11

Met Gln Thr Gln Ile Leu Glu Arg Met Glu Ser Asp Val Arg Thr Tyr
1               5                   10                  15

Ser Arg Ser Phe Pro Val Val Phe Thr Lys Ala Arg Asn Ala Arg Leu
            20                  25                  30

Thr Asp Glu Glu Gly Arg Glu Tyr Ile Asp Phe Leu Ala Gly Ala Gly
        35                  40                  45

Thr Leu Asn Tyr Gly His Asn Asn Pro His Leu Lys Gln Ala Leu Leu
    50                  55                  60

Asp Tyr Ile Asp Ser Asp Gly Ile Val His Gly Leu Asp Phe Trp Thr
65                  70                  75                  80

Ala Ala Lys Arg Asp Tyr Leu Glu Thr Leu Glu Val Ile Leu Lys
                85                  90                  95

Pro Arg Gly Leu Asp Tyr Lys Val His Leu Pro Gly Pro Thr Gly Thr
            100                 105                 110

Asn Ala Val Glu Ala Ala Ile Arg Leu Ala Arg Val Ala Lys Gly Arg
        115                 120                 125

His Asn Ile Val Ser Phe Thr Asn Gly Phe His Gly Val Thr Met Gly
    130                 135                 140

Ala Leu Ala Thr Thr Gly Asn Arg Lys Phe Arg Glu Ala Thr Gly Gly
145                 150                 155                 160

Val Pro Thr Gln Ala Ala Ser Phe Met Pro Phe Asp Gly Tyr Leu Gly
                165                 170                 175

Ser Ser Thr Asp Thr Leu Asp Tyr Phe Glu Lys Leu Leu Gly Asp Lys
            180                 185                 190

Ser Gly Gly Leu Asp Val Pro Ala Ala Val Ile Val Glu Thr Val Gln
        195                 200                 205

Gly Glu Gly Gly Ile Asn Val Ala Gly Leu Glu Trp Leu Lys Arg Leu
    210                 215                 220

Glu Ser Ile Cys Arg Ala Asn Asp Ile Leu Leu Ile Ile Asp Asp Ile
225                 230                 235                 240

Gln Ala Gly Cys Gly Arg Thr Gly Lys Phe Phe Ser Phe Glu His Ala
                245                 250                 255

Gly Ile Thr Pro Asp Ile Val Thr Asn Ser Lys Ser Leu Ser Gly Tyr
            260                 265                 270

Gly Leu Pro Phe Ala His Val Leu Met Arg Pro Glu Leu Asp Lys Trp
        275                 280                 285

Lys Pro Gly Gln Tyr Asn Gly Thr Phe Arg Gly Phe Asn Leu Ala Phe
    290                 295                 300
```

```
Ala Thr Ala Ala Ala Ala Met Arg Lys Tyr Trp Ser Asp Asp Thr Phe
305                 310                 315                 320

Glu Arg Asp Val Gln Arg Lys Ala Arg Ile Val Glu Glu Arg Phe Gly
                325                 330                 335

Lys Ile Ala Ala Trp Leu Ser Glu Asn Gly Ile Glu Ala Ser Glu Arg
            340                 345                 350

Gly Arg Gly Leu Met Arg Gly Ile Asp Val Gly Ser Gly Asp Ile Ala
        355                 360                 365

Asp Lys Ile Thr His Gln Ala Phe Glu Asn Gly Leu Ile Ile Glu Thr
    370                 375                 380

Ser Gly Gln Asp Gly Glu Val Val Lys Cys Leu Cys Pro Leu Thr Ile
385                 390                 395                 400

Pro Asp Glu Asp Leu Val Glu Gly Leu Asp Ile Leu Glu Thr Ser Thr
                405                 410                 415

Lys Gln Ala Phe Ser
            420

<210> SEQ ID NO 12
<211> LENGTH: 1461
<212> TYPE: DNA
<213> ORGANISM: Saccharomyces cerevisiae
<220> FEATURE:
<223> OTHER INFORMATION: HOMOSERINE O-ACETYLTRANSFERASE (MET2; METX)
<220> FEATURE:
<223> OTHER INFORMATION: HOMOSERINE O-ACETYLTRANSFERASE (MET2; METX)

<400> SEQUENCE: 12
atgtcgcata ctttaaaatc gaaaacgctc caagagctgg acattgagga gattaaggaa      60
actaacccat tgctcaaact agttcaaggg cagaggattg ttcaagttcc ggaactagtg     120
cttgagtctg gcgtggtcat aaataatttc cctattgctt ataagacgtg gggtacactg     180
aatgaagctg gtgataatgt tctggtaatt tgtcatgcct tgactgggtc cgcagatgtt     240
gctgactggt ggggcccctct tctgggtaac gacttagcat tcgacccatc aaggtttttt     300
atcatatgtt taaactctat gggctctcca tatgggtctt tttcgccatt aacgataaat     360
gaggagacgg gcgttagata tggacccgaa ttcccattat gtactgtgcg cgatgacgtt     420
agagctcaca gaattgttct ggattctctg ggagtaaagt caatagcctg tgttattggt     480
ggctctatgg gggggatgct gagttttgaa tgggctgcca tgtatggtaa ggaatatgtg     540
aagaatatgg ttgctctggc gacatcagca agacattctg cctggtgcat atcgtggtct     600
gaggctcaaa gacaatcgat ttactcagat cccaactact tggacgggta ctatccggta     660
gaggagcaac tgtgtggccgg actatcggct gcacgtatgt ctgcattgtt gacgtacagg     720
acaagaaaca gtttcgagaa caaattctcc agaagatctc cttcaatagc acaacaacaa     780
aaagctcaaa gggaggagac acgcaaacca tctactgtca gcgaacactc cctacaaatc     840
cacaatgatg gtataaaaac aaaagccagc actgccatcg ctggcatttc tgggcaaaaa     900
ggtcaaagcg tggtgtccac cgcatcttct tcggattcat tgaattcttc aacatcgatg     960
acttcggtaa gttctgtaac gggtgaagtg aaggacataa agcctgcgca gacgtatttt    1020
tctgcacaaa gttacttgag gtaccagggc acaaagttca tcataggtt cgacgccaat    1080 tgttacattg ccatcacacg taactggat acgcacgatt tggcaagaga cagagtagat    1140
gacatcactg aggtcctttc taccatccaa caaccatccc tgatcatcgg tatccaatct    1200
gatggactgt tcacatattc agaacaagaa ttttttggctg agcacatacc gaagtcgcaa    1260
ttagaaaaaa ttgaatctcc cgaaggccac gatgccttcc tattggagtt taagctgata    1320
```

```
aacaaactga tagtacaatt tttaaaaacc aactgcaagg ccattaccga tgccgctcca    1380
agagcttggg gaggtgacgt tggtaacgat gaaacgaaga cgtctgtctt tggtgaggcc    1440
gaagaagtta ccaactggta g                                              1461
```

<210> SEQ ID NO 13
<211> LENGTH: 486
<212> TYPE: PRT
<213> ORGANISM: Saccharomyces cerevisiae
<220> FEATURE:
<223> OTHER INFORMATION: HOMOSERINE O-ACETYLTRANSFERASE (MET2; METX)
<220> FEATURE:
<223> OTHER INFORMATION: HOMOSERINE O-ACETYLTRANSFERASE (MET2; METX)

<400> SEQUENCE: 13

```
Met Ser His Thr Leu Lys Ser Lys Thr Leu Gln Glu Leu Asp Ile Glu
1               5                   10                  15

Glu Ile Lys Glu Thr Asn Pro Leu Leu Lys Leu Val Gln Gly Gln Arg
            20                  25                  30

Ile Val Gln Val Pro Glu Leu Val Leu Glu Ser Gly Val Val Ile Asn
        35                  40                  45

Asn Phe Pro Ile Ala Tyr Lys Thr Trp Gly Thr Leu Asn Glu Ala Gly
    50                  55                  60

Asp Asn Val Leu Val Ile Cys His Ala Leu Thr Gly Ser Ala Asp Val
65                  70                  75                  80

Ala Asp Trp Trp Gly Pro Leu Leu Gly Asn Asp Leu Ala Phe Asp Pro
                85                  90                  95

Ser Arg Phe Phe Ile Ile Cys Leu Asn Ser Met Gly Ser Pro Tyr Gly
            100                 105                 110

Ser Phe Ser Pro Leu Thr Ile Asn Glu Glu Thr Gly Val Arg Tyr Gly
        115                 120                 125

Pro Glu Phe Pro Leu Cys Thr Val Arg Asp Asp Val Arg Ala His Arg
    130                 135                 140

Ile Val Leu Asp Ser Leu Gly Val Lys Ser Ile Ala Cys Val Ile Gly
145                 150                 155                 160

Gly Ser Met Gly Gly Met Leu Ser Leu Glu Trp Ala Ala Met Tyr Gly
                165                 170                 175

Lys Glu Tyr Val Lys Asn Met Val Ala Leu Ala Thr Ser Ala Arg His
            180                 185                 190

Ser Ala Trp Cys Ile Ser Trp Ser Glu Ala Gln Arg Gln Ser Ile Tyr
        195                 200                 205

Ser Asp Pro Asn Tyr Leu Asp Gly Tyr Tyr Pro Val Glu Glu Gln Pro
    210                 215                 220

Val Ala Gly Leu Ser Ala Ala Arg Met Ser Ala Leu Leu Thr Tyr Arg
225                 230                 235                 240

Thr Arg Asn Ser Phe Glu Asn Lys Phe Ser Arg Arg Ser Pro Ser Ile
                245                 250                 255

Ala Gln Gln Gln Lys Ala Gln Arg Glu Glu Thr Arg Lys Pro Ser Thr
            260                 265                 270

Val Ser Glu His Ser Leu Gln Ile His Asn Asp Gly Tyr Lys Thr Lys
        275                 280                 285

Ala Ser Thr Ala Ile Ala Gly Ile Ser Gly Gln Lys Gly Gln Ser Val
    290                 295                 300

Val Ser Thr Ala Ser Ser Ser Asp Ser Leu Asn Ser Thr Ser Met
305                 310                 315                 320
```

```
Thr Ser Val Ser Ser Val Thr Gly Glu Val Lys Asp Ile Lys Pro Ala
            325                 330                 335

Gln Thr Tyr Phe Ser Ala Gln Ser Tyr Leu Arg Tyr Gln Gly Thr Lys
        340                 345                 350

Phe Ile Asn Arg Phe Asp Ala Asn Cys Tyr Ile Ala Ile Thr Arg Lys
    355                 360                 365

Leu Asp Thr His Asp Leu Ala Arg Asp Arg Val Asp Ile Thr Glu
370                 375                 380

Val Leu Ser Thr Ile Gln Gln Pro Ser Leu Ile Ile Gly Ile Gln Ser
385                 390                 395                 400

Asp Gly Leu Phe Thr Tyr Ser Glu Gln Glu Phe Leu Ala Glu His Ile
            405                 410                 415

Pro Lys Ser Gln Leu Glu Lys Ile Glu Ser Pro Glu Gly His Asp Ala
        420                 425                 430

Phe Leu Leu Glu Phe Lys Leu Ile Asn Lys Leu Ile Val Gln Phe Leu
    435                 440                 445

Lys Thr Asn Cys Lys Ala Ile Thr Asp Ala Ala Pro Arg Ala Trp Gly
450                 455                 460

Gly Asp Val Gly Asn Asp Glu Thr Lys Thr Ser Val Phe Gly Glu Ala
465                 470                 475                 480

Glu Glu Val Thr Asn Trp
            485
```

<210> SEQ ID NO 14
<211> LENGTH: 579
<212> TYPE: DNA
<213> ORGANISM: Halomonas elongata
<220> FEATURE:
<223> OTHER INFORMATION: ACID ACETYLTRANSFERASE (EctA)
<220> FEATURE:
<223> OTHER INFORMATION: ACID ACETYLTRANSFERASE (EctA)

<400> SEQUENCE: 14

```
atgactccca caacagaaaa ttttactcct agtgcagatc tggctcgccc ttcagtggct    60
gacaccgtta ttggctccgc caagaaaaca ctattcatca gaaagcctac cacggacgat   120 ggttgggta tctacgagtt agttaaggcg tgcccaccct tggacgtaaa ctctggatac    180
gcttacttat tattagccac gcaatttagg gatacgtgtg ctgtcgctac cgacgaggaa   240
ggggagatcg ttggctttgt atcaggatac gttaagcgta acgcacctga tacctatttt   300
ctatggcaag ttgctgtggg cgaaaaggct cgtgggacgg tcttgcaag aagattagtc    360 gaagccgtat tgatgagacc aggtatggga gatgtccggc acctggagac taccataact   420
cctgataacg aagcaagctg gggtctcttt aaacgacttg ccgatagatg caagcgcca    480 ttgaattcta gggaatattt ctctactggt cagttgggtg gtgaacatga tccggaaaat   540
ctggtgagaa ttggaccgtt cgaaccacag caaatttaa                          579
```

<210> SEQ ID NO 15
<211> LENGTH: 192
<212> TYPE: PRT
<213> ORGANISM: Halomonas elongata
<220> FEATURE:
<223> OTHER INFORMATION: ACID ACETYLTRANSFERASE (EctA)
<220> FEATURE:
<223> OTHER INFORMATION: ACID ACETYLTRANSFERASE (EctA)

<400> SEQUENCE: 15

```
Met Thr Pro Thr Thr Glu Asn Phe Thr Pro Ser Ala Asp Leu Ala Arg
1               5                   10                  15
```

-continued

```
Pro Ser Val Ala Asp Thr Val Ile Gly Ser Ala Lys Lys Thr Leu Phe
            20                  25                  30

Ile Arg Lys Pro Thr Thr Asp Asp Gly Trp Gly Ile Tyr Glu Leu Val
        35                  40                  45

Lys Ala Cys Pro Pro Leu Asp Val Asn Ser Gly Tyr Ala Tyr Leu Leu
    50                  55                  60

Leu Ala Thr Gln Phe Arg Asp Thr Cys Ala Val Ala Thr Asp Glu Glu
65                  70                  75                  80

Gly Glu Ile Val Gly Phe Val Ser Gly Tyr Val Lys Arg Asn Ala Pro
                85                  90                  95

Asp Thr Tyr Phe Leu Trp Gln Val Ala Val Gly Glu Lys Ala Arg Gly
            100                 105                 110

Thr Gly Leu Ala Arg Arg Leu Val Glu Ala Val Leu Met Arg Pro Gly
        115                 120                 125

Met Gly Asp Val Arg His Leu Glu Thr Thr Ile Thr Pro Asp Asn Glu
130                 135                 140

Ala Ser Trp Gly Leu Phe Lys Arg Leu Ala Asp Arg Trp Gln Ala Pro
145                 150                 155                 160

Leu Asn Ser Arg Glu Tyr Phe Ser Thr Gln Leu Gly Gly Glu His
                165                 170                 175

Asp Pro Glu Asn Leu Val Arg Ile Gly Pro Phe Glu Pro Gln Gln Ile
            180                 185                 190
```

<210> SEQ ID NO 16
<211> LENGTH: 414
<212> TYPE: DNA
<213> ORGANISM: Halomonas elongata
<220> FEATURE:
<223> OTHER INFORMATION: ECTOINE SYNTHASE (EctC)
<220> FEATURE:
<223> OTHER INFORMATION: ECTOINE SYNTHASE (EctC)

<400> SEQUENCE: 16

```
atgatagttc gtaacctgga ggaagctagg caaacagata gattagtgac cgctgagaat      60
ggcaactggg acagtaccag attatcatta gctgaggacg gaggtaattg ttcttttcac     120
attaccagaa tatttgaagg gactgaaact cacatacact acaagcatca ctttgaagcc     180
gtttactgca tcgagggtga aggagaagtc gaaaccctcg ctgatggaaa gatctggccc     240
ataaaacctg gggatattta tattttggat cagcatgacg aacatttgct tagggcttcg     300
aaaactatgc atctagcatg cgtattcacg ccgggtctaa ctggtaatga agttcatcga     360
gaagacggtt cctatgcacc agcggatgaa gcagatgatc agaaaccact ttaa           414
```

<210> SEQ ID NO 17
<211> LENGTH: 137
<212> TYPE: PRT
<213> ORGANISM: Halomonas elongata
<220> FEATURE:
<223> OTHER INFORMATION: ECTOINE SYNTHASE (EctC)
<220> FEATURE:
<223> OTHER INFORMATION: ECTOINE SYNTHASE (EctC)

<400> SEQUENCE: 17

```
Met Ile Val Arg Asn Leu Glu Glu Ala Arg Gln Thr Asp Arg Leu Val
1               5                   10                  15

Thr Ala Glu Asn Gly Asn Trp Asp Ser Thr Arg Leu Ser Leu Ala Glu
            20                  25                  30

Asp Gly Gly Asn Cys Ser Phe His Ile Thr Arg Ile Phe Glu Gly Thr
```

```
              35                  40                  45
Glu Thr His Ile His Tyr Lys His His Phe Glu Ala Val Tyr Cys Ile
 50                  55                  60

Glu Gly Glu Gly Glu Val Glu Thr Leu Ala Asp Gly Lys Ile Trp Pro
 65                  70                  75                  80

Ile Lys Pro Gly Asp Ile Tyr Ile Leu Asp Gln His Asp Glu His Leu
                 85                  90                  95

Leu Arg Ala Ser Lys Thr Met His Leu Ala Cys Val Phe Thr Pro Gly
                100                 105                 110

Leu Thr Gly Asn Glu Val His Arg Glu Asp Gly Ser Tyr Ala Pro Ala
            115                 120                 125

Asp Glu Ala Asp Asp Gln Lys Pro Leu
130                 135

<210> SEQ ID NO 18
<211> LENGTH: 1080
<212> TYPE: DNA
<213> ORGANISM: Saccharomyces cerevisiae
<220> FEATURE:
<223> OTHER INFORMATION: HOMOSERINE DESHYDROGENASE (HOM6)
<220> FEATURE:
<223> OTHER INFORMATION: HOMOSERINE DESHYDROGENASE (HOM6)

<400> SEQUENCE: 18
atgagcacta aagttgttaa tgttgccgtt atcggtgccg gtgttgttgg ttcagctttc      60
ttggatcaat tgttagccat gaagtctacc attacttaca atctagttct tttggctgaa     120
gctgagcgtt ctttaatctc caaggacttt tctccattaa atgttggttc tgattggaag     180
gctgctttag cagcctccac tactaaaacg ttgcctttgg atgatttaat tgctcatttg     240
aagacttcac ctaagccagt cattttggtt gataacactt ccagcgctta cattgctggt     300
ttttacacta gttttgtcga aatggtatt tccattgcta ctccaaacaa gaaggccttt     360
tcctctgatt tggctacctg gaaggctctt ttctcaaata agccaactaa cggttttgtc     420
tatcatgaag ctaccgtcgg tgctggtttg cctatcatca gtttcttaag agaaattatt     480
caaaccggtg acgaagttga aaaaattgaa ggtatcttct ctggtactct atcttatatt     540
ttcaacgagt tctccactag tcaagctaac gacgtcaaat tctctgatgt tgtcaaagtt     600
gctaaaaaat tgggttatac tgaaccagat ccaagagatg atttgaatgg ttggatgtt     660 gctagaaagg ttaccattgt tggtaggata tctggtgtgg aagttgaatc tccaacttcc     720
ttccctgtcc agtctttgat tccaaaacca ttggaatctg tcaagtctgc tgatgaattc     780
ttggaaaaat tatctgatta cgataaagat ttgactcaat gaagaagga agctgccact     840 gaaaataagg tattgagatt cattggtaaa gtcgatgttg ccaccaaatc tgtgtctgta     900
ggaattgaaa agtacgatta ctcacaccca ttcgcatcat gaagggatc agataacgtt     960 atttccatca agactaagcg ttacaccaat cctgttgtca ttcaaggtgc cggtgccggt    1020
gctgccgtta ctgccgctgg tgttttgggt gatgttatca agattgctca aagactttaa    1080

<210> SEQ ID NO 19
<211> LENGTH: 308
<212> TYPE: PRT
<213> ORGANISM: Saccharomyces cerevisiae
<220> FEATURE:
<223> OTHER INFORMATION: HOMOSERINE DESHYDROGENASE (HOM6)
<220> FEATURE:
<223> OTHER INFORMATION: HOMOSERINE DESHYDROGENASE (HOM6)

<400> SEQUENCE: 19
```

```
Met Ser Thr Lys Val Val Asn Val Ala Val Ile Gly Ala Gly Val Val
1               5                   10                  15

Gly Ser Ala Phe Leu Asp Gln Leu Leu Ala Met Lys Ser Thr Ile Thr
            20                  25                  30

Tyr Asn Leu Val Leu Leu Ala Glu Ala Glu Arg Ser Leu Ile Ser Lys
                35                  40                  45

Asp Phe Ser Pro Leu Asn Val Gly Ser Asp Trp Lys Ala Ala Leu Ala
        50                  55                  60

Ala Ser Thr Thr Lys Thr Leu Pro Leu Asp Asp Leu Ile Ala His Leu
65                  70                  75                  80

Lys Thr Ser Pro Lys Pro Val Ile Leu Val Asp Asn Thr Ser Ser Ala
                85                  90                  95

Tyr Ile Ala Gly Phe Tyr Thr Lys Phe Val Glu Asn Gly Ile Ser Ile
            100                 105                 110

Ala Thr Pro Asn Lys Lys Ala Phe Ser Ser Asp Leu Ala Thr Trp Lys
        115                 120                 125

Ala Leu Phe Ser Asn Lys Pro Thr Asn Gly Phe Val Tyr His Glu Ala
130                 135                 140

Thr Val Gly Ala Gly Leu Pro Ile Ile Ser Phe Leu Arg Glu Ile Ile
145                 150                 155                 160

Gln Thr Gly Asp Glu Val Glu Lys Ile Glu Gly Ile Phe Ser Gly Thr
                165                 170                 175

Leu Ser Tyr Ile Phe Asn Glu Phe Ser Thr Ser Gln Ala Asn Asp Val
            180                 185                 190

Lys Phe Ser Asp Val Val Lys Val Ala Lys Lys Leu Gly Tyr Thr Glu
        195                 200                 205

Pro Asp Pro Arg Asp Asp Leu Asn Gly Leu Asp Val Ala Arg Lys Val
        210                 215                 220

Thr Ile Val Gly Arg Ile Ser Gly Val Glu Val Glu Ser Pro Thr Ser
225                 230                 235                 240

Phe Pro Val Gln Ser Leu Ile Pro Lys Pro Leu Glu Ser Val Lys Ser
                245                 250                 255

Ala Asp Glu Phe Leu Glu Lys Leu Ser Asp Tyr Asp Lys Asp Leu Thr
            260                 265                 270

Gln Leu Lys Lys Glu Ala Ala Thr Glu Asn Lys Val Leu Arg Phe Ile
        275                 280                 285

Gly Lys Val Asp Val Ala Thr Lys Ser Val Ser Val Gly Ile Glu Lys
290                 295                 300

Tyr Asp Tyr Ser
305
```

<210> SEQ ID NO 20
<211> LENGTH: 1257
<212> TYPE: DNA
<213> ORGANISM: Saccharomyces cerevisiae
<220> FEATURE:
<223> OTHER INFORMATION: ASPARTATE TRANSAMINASE (AAT2)
<220> FEATURE:
<223> OTHER INFORMATION: ASPARTATE TRANSAMINASE (AAT2)

<400> SEQUENCE: 20

```
atgtctgcca ctctgttcaa taacatcgaa ttgctgcccc ctgatgccct ttttggtatt      60
aagcaaaggt acgggcaaga tcaacgtgct accaaggtcg acttgggtat cggggcctac     120
agagacgaca acggtaaacc atgggtcttg ccaagtgtta agccgccga aaagctaatt      180
```

```
cataacgaca gctcctacaa ccatgaatac ctcggtatta ccggtctgcc aagtttgaca    240
tctaacgccg ccaagatcat cttcggtacg caatccgatg cctttcagga agacagagta    300
atctcagtac aatcactgtc tggtacgggt gctcttcata tatctgcgaa gttttttca    360 aaattcttcc cagataaact ggtctatttg tctaagccta cttgggccaa ccacatggcc    420 attttttgaga atcaaggctt gaaaacggcg acttacccct actgggccaa cgaaactaag    480
tctttggacc taaacggctt tctaaatgct attcaaaaag ctccagaggg ctccattttc    540
gttctgcact cttgcgccca taacccaact ggtctggacc tactagtga acaatgggtt     600 caaatcgttg atgctatcgc ctcaaagaac cacatcgcct tatttgacac cgcctaccaa    660
gggtttgcca ctggagattt ggacaaggat gcctatgctg tgcgtctagg tgtggagaag    720 cttcaacgg tctctcccgt ctttgtctgt cagtcctttg ccaagaacgc cggtatgtac     780
ggtgagcgtg taggttgttt ccatctagca cttacaaaac aagctcaaaa caaaactata    840
aagcctgctg ttacatctca attggccaaa atcattcgta gtgaagtgtc caacccaccc    900
gcctacggcg ctaagattgt cgctaaactg ttggaaacgc cagaattaac ggaacagtgg    960
cacaaggata tggttaccat gtcctccaga attacgaaaa tgaggcacgc attaagagac   1020
catttagtca agttgggcac tcctggcaac tgggatcata tagtaaatca atgcgggatg   1080
ttctccttta cagggttgac tcctcaaatg gttaaacgac ttgaagaaac ccacgcagtt   1140
tacttggttg cctcaggtag agcttctatt gctggattga atcaaggaaa cgtggaatac   1200
gtggctaaag ccattgatga agtggtgcgc ttctatacta ttgaagctaa attgtaa      1257
```

<210> SEQ ID NO 21
<211> LENGTH: 418
<212> TYPE: PRT
<213> ORGANISM: Saccharomyces cerevisiae
<220> FEATURE:
<223> OTHER INFORMATION: ASPARTATE TRANSAMINASE (AAT2)
<220> FEATURE:
<223> OTHER INFORMATION: ASPARTATE TRANSAMINASE (AAT2)

<400> SEQUENCE: 21

```
Met Ser Ala Thr Leu Phe Asn Asn Ile Glu Leu Leu Pro Pro Asp Ala
1               5                   10                  15

Leu Phe Gly Ile Lys Gln Arg Tyr Gly Gln Asp Gln Arg Ala Thr Lys
            20                  25                  30

Val Asp Leu Gly Ile Gly Ala Tyr Arg Asp Asp Asn Gly Lys Pro Trp
        35                  40                  45

Val Leu Pro Ser Val Lys Ala Ala Glu Lys Leu Ile His Asn Asp Ser
    50                  55                  60

Ser Tyr Asn His Glu Tyr Leu Gly Ile Thr Gly Leu Pro Ser Leu Thr
65                  70                  75                  80

Ser Asn Ala Ala Lys Ile Ile Phe Gly Thr Gln Ser Asp Ala Phe Gln
                85                  90                  95

Glu Asp Arg Val Ile Ser Val Gln Ser Leu Ser Gly Thr Gly Ala Leu
            100                 105                 110

His Ile Ser Ala Lys Phe Phe Ser Lys Phe Phe Pro Asp Lys Leu Val
        115                 120                 125

Tyr Leu Ser Lys Pro Thr Trp Ala Asn His Met Ala Ile Phe Glu Asn
    130                 135                 140

Gln Gly Leu Lys Thr Ala Thr Tyr Pro Tyr Trp Ala Asn Glu Thr Lys
145                 150                 155                 160

Ser Leu Asp Leu Asn Gly Phe Leu Asn Ala Ile Gln Lys Ala Pro Glu
```

```
                165                 170                 175
Gly Ser Ile Phe Val Leu His Ser Cys Ala His Asn Pro Thr Gly Leu
            180                 185                 190

Asp Pro Thr Ser Glu Gln Trp Val Gln Ile Val Asp Ala Ile Ala Ser
        195                 200                 205

Lys Asn His Ile Ala Leu Phe Asp Thr Ala Tyr Gln Gly Phe Ala Thr
    210                 215                 220

Gly Asp Leu Asp Lys Asp Ala Tyr Ala Val Arg Leu Gly Val Glu Lys
225                 230                 235                 240

Leu Ser Thr Val Ser Pro Val Phe Val Cys Gln Ser Phe Ala Lys Asn
                245                 250                 255

Ala Gly Met Tyr Gly Glu Arg Val Gly Cys Phe His Leu Ala Leu Thr
            260                 265                 270

Lys Gln Ala Gln Asn Lys Thr Ile Lys Pro Ala Val Thr Ser Gln Leu
        275                 280                 285

Ala Lys Ile Ile Arg Ser Glu Val Ser Asn Pro Pro Ala Tyr Gly Ala
    290                 295                 300

Lys Ile Val Ala Lys Leu Leu Glu Thr Pro Glu Leu Thr Glu Gln Trp
305                 310                 315                 320

His Lys Asp Met Val Thr Met Ser Ser Arg Ile Thr Lys Met Arg His
                325                 330                 335

Ala Leu Arg Asp His Leu Val Lys Leu Gly Thr Pro Gly Asn Trp Asp
            340                 345                 350

His Ile Val Asn Gln Cys Gly Met Phe Ser Phe Thr Gly Leu Thr Pro
        355                 360                 365

Gln Met Val Lys Arg Leu Glu Glu Thr His Ala Val Tyr Leu Val Ala
    370                 375                 380

Ser Gly Arg Ala Ser Ile Ala Gly Leu Asn Gln Gly Asn Val Glu Tyr
385                 390                 395                 400

Val Ala Lys Ala Ile Asp Glu Val Val Arg Phe Tyr Thr Ile Glu Ala
                405                 410                 415

Lys Leu
```

<210> SEQ ID NO 22
<211> LENGTH: 1317
<212> TYPE: DNA
<213> ORGANISM: Entodinium caudatum
<220> FEATURE:
<223> OTHER INFORMATION: GLUTAMATE DESHYDROGENASE (GDH)
<220> FEATURE:
<223> OTHER INFORMATION: GLUTAMATE DESHYDROGENASE (GDH)

<400> SEQUENCE: 22

```
atgatagatt tagaagcgag aaaccctgct caacccgaat tcattcaagc cagtagagaa    60
gtaatcgaat cgatcattga tgttgttaat agcaatccga aatacctgga aaacaaaatt   120
ttggagagaa ttacggaacc aaacctaatt cacgaattca agtcgaatg ggagaatgac    180 aagcacgaaa tcatggtgaa caaaggttat cgtattcagt tcaataatgc gataggtccc   240
tataagggag gcctaaggtt tcacagagca gtcactctag gtactctgaa attccttggt   300
tttgaacaga tatttaagaa ttccttgaca ggattaccta tgggaggtgg caaaggtggt   360
tcagattttg atcctagagg taaatcagat gccgagattt taagattctg taggtctttt   420
atgacttcgt tgttcaaata tattgggcca gagatagatg ttcctgctgg agatataggt   480
gtcggaggta gggaaattgg ttacttgttt ggccaataca aaagactgac ccaacaacat   540
```

```
gaaggagttc taactggtaa gggtcttaac tggggtggct ctcttgttag acctgaagcc    600
acaggttttg aacgatgta ttttgctaac gaagtcttac atgcacatgg tgacgacatc    660
aaggggaaaa ccattgccat atccggattt ggtaatgttg cctttggtgc tgtcttaaaa    720
gcgaaacaat taggcgctaa ggtagtcact atatctggcc cagatggtta catttatgac    780
gagaatggga taaacaccga cgagaaaatc aactacatgt ggaattaag agcctcaaat    840
aatgatgtgg ttgcgccatt tgcagagaag tttggtgcaa aattcatacc agggaagaag    900
ccatgggaag ttccagtgga tatggctttt ccctgtgcca ttcagaacga attgaatgcc    960
gaagatgctg ccactttaca taagaatgga gtgaaatatg tgatcgagac atccaatatg   1020
ggctgtacag cagatgctgt gcaatacttc attaagaacc gtattgtttt cgctccgggt   1080
aaagcagcta atgctggtgg tgttgcagta tctgggttgg aaatgagcca aaactcaatg   1140
aagttgaact ggacagctga agaagttgac gctaaattga agaatatcat gaccaatatt   1200
catgcaagtt gcgtaaagga aggaaaagag agtgacgggt atatcaatta cgttaaaggc   1260
gcaaatatag caggcttcaa gaaagtagct gatgcaatgg tagatcttgg ctattaa      1317
```

<210> SEQ ID NO 23
<211> LENGTH: 438
<212> TYPE: PRT
<213> ORGANISM: Entodinium caudatum
<220> FEATURE:
<223> OTHER INFORMATION: GLUTAMATE DESHYDROGENASE (GDH)
<220> FEATURE:
<223> OTHER INFORMATION: GLUTAMATE DESHYDROGENASE (GDH)

<400> SEQUENCE: 23

```
Met Ile Asp Leu Glu Ala Arg Asn Pro Ala Gln Pro Glu Phe Ile Gln
1               5                   10                  15

Ala Ser Arg Glu Val Ile Glu Ser Ile Ile Asp Val Val Asn Ser Asn
            20                  25                  30

Pro Lys Tyr Leu Glu Asn Lys Ile Leu Glu Arg Ile Thr Glu Pro Asn
        35                  40                  45

Leu Ile His Glu Phe Lys Val Glu Trp Glu Asn Asp Lys His Glu Ile
    50                  55                  60

Met Val Asn Lys Gly Tyr Arg Ile Gln Phe Asn Asn Ala Ile Gly Pro
65                  70                  75                  80

Tyr Lys Gly Gly Leu Arg Phe His Arg Ala Val Thr Leu Gly Thr Leu
                85                  90                  95

Lys Phe Leu Gly Phe Glu Gln Ile Phe Lys Asn Ser Leu Thr Gly Leu
            100                 105                 110

Pro Met Gly Gly Gly Lys Gly Gly Ser Asp Phe Asp Pro Arg Gly Lys
        115                 120                 125

Ser Asp Ala Glu Ile Leu Arg Phe Cys Arg Ser Phe Met Thr Ser Leu
    130                 135                 140

Phe Lys Tyr Ile Gly Pro Glu Ile Asp Val Pro Ala Gly Asp Ile Gly
145                 150                 155                 160

Val Gly Gly Arg Glu Ile Gly Tyr Leu Phe Gly Gln Tyr Lys Arg Leu
                165                 170                 175

Thr Gln Gln His Glu Gly Val Leu Thr Gly Lys Gly Leu Asn Trp Gly
            180                 185                 190

Gly Ser Leu Val Arg Pro Glu Ala Thr Gly Phe Gly Thr Met Tyr Phe
        195                 200                 205

Ala Asn Glu Val Leu His Ala His Gly Asp Asp Ile Lys Gly Lys Thr
    210                 215                 220
```

Ile Ala Ile Ser Gly Phe Gly Asn Val Ala Phe Gly Ala Val Leu Lys
225                 230                 235                 240

Ala Lys Gln Leu Gly Ala Lys Val Val Thr Ile Ser Gly Pro Asp Gly
            245                 250                 255

Tyr Ile Tyr Asp Glu Asn Gly Ile Asn Thr Asp Glu Lys Ile Asn Tyr
        260                 265                 270

Met Leu Glu Leu Arg Ala Ser Asn Asn Asp Val Val Ala Pro Phe Ala
    275                 280                 285

Glu Lys Phe Gly Ala Lys Phe Ile Pro Gly Lys Lys Pro Trp Glu Val
290                 295                 300

Pro Val Asp Met Ala Phe Pro Cys Ala Ile Gln Asn Glu Leu Asn Ala
305                 310                 315                 320

Glu Asp Ala Ala Thr Leu His Lys Asn Gly Val Lys Tyr Val Ile Glu
                325                 330                 335

Thr Ser Asn Met Gly Cys Thr Ala Asp Ala Val Gln Tyr Phe Ile Lys
            340                 345                 350

Asn Arg Ile Val Phe Ala Pro Gly Lys Ala Asn Ala Gly Gly Val
        355                 360                 365

Ala Val Ser Gly Leu Glu Met Ser Gln Asn Ser Met Lys Leu Asn Trp
370                 375                 380

Thr Ala Glu Glu Val Asp Ala Lys Leu Lys Asn Ile Met Thr Asn Ile
385                 390                 395                 400

His Ala Ser Cys Val Lys Glu Gly Lys Glu Ser Asp Gly Tyr Ile Asn
                405                 410                 415

Tyr Val Lys Gly Ala Asn Ile Ala Gly Phe Lys Lys Val Ala Asp Ala
        420                 425                 430

Met Val Asp Leu Gly Tyr
        435

<210> SEQ ID NO 24
<211> LENGTH: 554
<212> TYPE: DNA
<213> ORGANISM: Saccharomyces cerevisiae
<220> FEATURE:
<223> OTHER INFORMATION: pTDH3
<220> FEATURE:
<223> OTHER INFORMATION: pTDH3

<400> SEQUENCE: 24
ccaaaatagg gggcgggtta cacagaatat ataacatcgt aggtgtctgg gtgaacagtt      60
tattcctggc atccactaaa tataatggag cccgcttttt aagctggcat ccagaaaaaa    120
aaagaatccc agcaccaaaa tattgttttc ttcaccaacc atcagttcat aggtccattc    180
tcttagcgca actacagaga acaggggcac aaacaggcaa aaacgggca caacctcaat     240 ggagtgatgc aacctgcctg gagtaaatga tgacacaagg caattgaccc acgcatgtat    300
ctatctcatt tcttacacc ttctattacc ttctgctctc tctgatttgg aaaaagctga    360 aaaaaaggt tgaaaccagt tccctgaaat tattccccta cttgactaat aagtatataa    420
agacggtagg tattgattgt aattctgtaa atctatttct taaacttctt aaattctact    480
tttatagtta gtctttttt tagttttaaa acaccaagaa cttagtttcg aataaacaca    540
cataaacaaa caaa                                                      554

<210> SEQ ID NO 25
<211> LENGTH: 550
<212> TYPE: DNA

<213> ORGANISM: Saccharomyces cerevisiae
<220> FEATURE:
<223> OTHER INFORMATION: pENO2
<220> FEATURE:
<223> OTHER INFORMATION: pENO2

<400> SEQUENCE: 25

```
cgctcagcat ctgcttcttc ccaaagatga acgcggcgtt atgtcactaa cgacgtgcac    60
caacttgcgg aaagtggaat cccgttccaa aactggcatc cactaattga tacatctaca   120
caccgcacgc cttttttctg aagcccactt tcgtggactt tgccatatgc aaaattcatg   180
aagtgtgata ccaagtcagc atacacctca ctagggtagt ttctttggtt gtattgatca   240
tttggttcat cgtggttcat taatttttt tctccattgc tttctggctt tgatcttact   300
atcatttgga ttttttgtcga aggttgtaga attgtatgtg acaagtggca ccaagcatat   360
ataaaaaaaa aaagcattat cttcctacca gagttgattg ttaaaaacgt atttatagca   420
aacgcaattg taattaattc ttattttgta tcttttcttc ccttgtctca atcttttatt   480
tttattttat ttttctttttc ttagtttctt tcataacacc aagcaactaa tactataaca   540
tacaataata                                                          550
```

<210> SEQ ID NO 26
<211> LENGTH: 419
<212> TYPE: DNA
<213> ORGANISM: Saccharomyces cerevisiae
<220> FEATURE:
<223> OTHER INFORMATION: pTEF Kl
<220> FEATURE:
<223> OTHER INFORMATION: pTEF Kl

<400> SEQUENCE: 26

```
ctctctcgca ataacaatga acactgggtc aatcatagcc tacacaggtg aacagagtag    60
cgtttataca gggtttatac ggtgattcct acggcaaaaa ttttcattt ctaaaaaaaa    120
aaagaaaaat ttttctttcc aacgctagaa ggaaaagaaa aatctaatta aattgatttg   180
gtgattttct gagagttccc ttttcatat atcgaatttt gaatataaaa ggagatcgaa    240
aaaatttttc tattcaatct gttttctggt tttatttgat agttttttg tgtattatta    300
ttatggatta gtactggttt atatgggttt ttctgtataa cttcttttta ttttagtttg   360
tttaatctta ttttgagtta cattatagtt ccctaactgc aagagaagta acattaaaa    419
```

<210> SEQ ID NO 27
<211> LENGTH: 598
<212> TYPE: DNA
<213> ORGANISM: Saccharomyces cerevisiae
<220> FEATURE:
<223> OTHER INFORMATION: pTEF3
<220> FEATURE:
<223> OTHER INFORMATION: pTEF3

<400> SEQUENCE: 27

```
ggctgataat agcgtataaa caatgcatac tttgtacgtt caaaatacaa tgcagtagat    60
atatttatgc atattacata taatacatat cacataggaa gcaacaggcg cgttggactt   120
ttaattttcg aggaccgcga atccttacat cacacccaat cccccacaag tgatccccca   180
cacaccatag cttcaaaatg tttctactcc ttttttactc ttccagattt tctcggactc   240
cgcgcatcgc cgtaccactt caaaacaccc aagcacagca tactaaattt ccctctcttc   300
ttcctctagg gtgtcgttaa ttacccgtac taaaggtttg gaaaagaaaa aagagaccgc   360
ctcgtttctt tttcttcgtc gaaaaaggca ataaaaattt ttatcacgtt tctttttctt   420
```

```
gaaaattttt tttttttgatt tttttctctt tcgatgacct cccattgata tttaagttaa      480
taaacggtct tcaatttctc aagtttcagt ttcattttc ttgttctatt acaacttttt       540
ttacttcttg ctcattagaa agaaagcata gcaatctaat ctaagtttta attacaaa        598
```

<210> SEQ ID NO 28
<211> LENGTH: 383
<212> TYPE: DNA
<213> ORGANISM: Saccharomyces cerevisiae
<220> FEATURE:
<223> OTHER INFORMATION: pTEF1
<220> FEATURE:
<223> OTHER INFORMATION: pTEF1

<400> SEQUENCE: 28

```
gtttagcttg cctcgtcccc gccgggtcac ccggccagcg acatggaggc ccagaatacc       60
ctccttgaca gtcttgacgt gcgcagctca ggggcatgat gtgactgtcg cccgtacatt      120
tagcccatac atccccatgt ataatcattt gcatccatac attttgatgg ccgcacggcg      180
cgaagcaaaa attacggctc ctcgctgcag acctgcgagc agggaaacgc tcccctcaca      240
gacgcgttga attgtcccca cgccgcgccc ctgtagagaa atataaaagg ttaggatttg      300
ccactgaggt tcttctttca tatacttcct tttaaaatct tgctacgata cagttctcac      360
atcacatccg aacataaaca acc                                              383
```

<210> SEQ ID NO 29
<211> LENGTH: 700
<212> TYPE: DNA
<213> ORGANISM: Saccharomyces cerevisiae
<220> FEATURE:
<223> OTHER INFORMATION: pADH1
<220> FEATURE:
<223> OTHER INFORMATION: pADH1

<400> SEQUENCE: 29

```
gggtgtacaa tatggacttc ctcttttctg gcaaccaaac ccatacatcg ggattcctat       60
aataccttcg ttggtctccc taacatgtag gtggcggagg ggagatatac aatagaacag      120
ataccagaca agacataatg ggctaaacaa gactacacca attacactgc ctcattgatg      180
gtggtacata acgaactaat actgtagccc tagacttgat agccatcatc atatcgaagt      240
ttcactaccc ttttttccatt tgccatctat tgaagtaata ataggcgcat gcaacttctt      300 ttctttttttt ttcttttctc tctccccccgt tgttgtctca ccatatccgc aatgacaaaa      360
aaatgatgga agacactaaa ggaaaaaatt aacgacaaag acagcaccaa cagatgtcgt      420
tgttccagag ctgatgaggg gtatctcgaa gcacacgaaa cttttttcctt ccttcattca      480 cgcacactac tctctaatga gcaacggtat acggccttcc ttccagttac ttgaatttga      540
aataaaaaaa agtttgctgt cttgctatca agtataaata gacctgcaat tattaatctt      600
ttgtttcctc gtcattgttc tcgttccctt tcttccttgt ttcttttttct gcacaatatt      660 tcaagctata ccaagcatac aatcaactat ctctatataca                           700
```

<210> SEQ ID NO 30
<211> LENGTH: 549
<212> TYPE: DNA
<213> ORGANISM: Saccharomyces cerevisiae
<220> FEATURE:
<223> OTHER INFORMATION: pGPM 1
<220> FEATURE:
<223> OTHER INFORMATION: pGPM 1

<400> SEQUENCE: 30

```
gccaaacttt tcggttaaca catgcagtga tgcacgcgcg atggtgctaa gttacatata      60
tatatatata tatatatata tatatatata gccatagtga tgtctaagta acctttatgg     120
tatatttctt aatgtggaaa gatactagcg cgcgcaccca cacacaagct tcgtcttttc     180
ttgaagaaaa gaggaagctc gctaaatggg attccacttt ccgttccctg ccagctgatg     240
gaaaaaggtt agtggaacga tgaagaataa aagagagat ccactgaggt gaaatttcag      300
ctgacagcga gtttcatgat cgtgatgaac aatggtaacg agttgtggct gttgccaggg     360
agggtggttc tcaacttta atgtatggcc aaatcgctac ttgggtttgt tatataacaa      420
agaagaaata atgaactgat tctcttcctc cttcttgtcc tttcttaatt ctgttgtaat     480
taccttcctt tgtaattttt tttgtaatta ttcttcttaa taatccaaac aaacacacat     540
attacaata                                                            549
```

<210> SEQ ID NO 31
<211> LENGTH: 650
<212> TYPE: DNA
<213> ORGANISM: Saccharomyces cerevisiae
<220> FEATURE:
<223> OTHER INFORMATION: pFBA1
<220> FEATURE:
<223> OTHER INFORMATION: pFBA1

<400> SEQUENCE: 31

```
acgcaagccc taagaaatga ataacaaatac tgacagtact aaataattgc ctacttggct     60
tcacatacgt tgcatacgtc gatatagata ataatgataa tgacagcagg attatcgtaa    120
tacgtaatag ttgaaaatct caaaaatgtg tgggtcatta cgtaaataat gataggaatg    180
ggattcttct atttttcctt tttccattct agcagccgtc gggaaaacgt ggcatcctct    240
ctttcgggct caattggagt cacgctgccg tgagcatcct ctctttccat atctaacaac    300
tgagcacgta accaatggaa aagcatgagc ttagcgttgc tccaaaaag tattggatgg    360 ttaataccat ttgtctgttc tcttctgact ttgactcctc aaaaaaaaaa aatctacaat    420
caacagatcg cttcaattac gccctcacaa aaactttttt ccttcttctt cgcccacgtt    480
aaattttatc cctcatgttg tctaacggat ttctgcactt gatttattat aaaaagacaa    540
agacataata cttctctatc aatttcagtt attgttcttc cttgcgttat tcttctgttc    600 ttcttttct tttgtcatat ataaccataa ccaagtaata catattcaaa                650
```

<210> SEQ ID NO 32
<211> LENGTH: 700
<212> TYPE: DNA
<213> ORGANISM: Saccharomyces cerevisiae
<220> FEATURE:
<223> OTHER INFORMATION: pPDC1
<220> FEATURE:
<223> OTHER INFORMATION: pPDC1

<400> SEQUENCE: 32

```
ttatttacct atctctaaac ttcaacacct tatatcataa ctaatatttc ttgagataag      60
cacactgcac ccataccttc cttaaaaacg tagcttccag ttttttggtgg ttccggcttc    120 cttcccgatt ccgcccgcta aacgcatatt tttgttgcct ggtggcattt gcaaaatgca    180
taacctatgc atttaaaaga ttatgtatgc tcttctgact tttcgtgtga tgaggctcgt    240
ggaaaaaatg aataatttat gaatttgaga acaattttgt gttgttacgg tattttacta    300
tggaataatc aatcaattga ggattttatg caaatatcgt ttgaatattt ttccgaccct    360
```

```
ttgagtactt tcttcataa ttgcataata ttgtccgctg ccccttttc tgttagacgg    420 tgtcttgatc tacttgctat cgttcaacac caccttattt tctaactatt ttttttttag    480
ctcatttgaa tcagcttatg gtgatggcac attttgcat aaacctagct gtcctcgttg    540
aacataggaa aaaaaatat ataaacaagg ctctttcact ctccttgcaa tcagatttgg    600
gtttgttccc tttattttca tatttcttgt catattcctt tctcaattat tattttctac    660
tcataacctc acgcaaaata acacagtcaa atcaatcaaa                          700
```

<210> SEQ ID NO 33
<211> LENGTH: 998
<212> TYPE: DNA
<213> ORGANISM: Saccharomyces cerevisiae
<220> FEATURE:
<223> OTHER INFORMATION: pCCW12
<220> FEATURE:
<223> OTHER INFORMATION: pCCW12

<400> SEQUENCE: 33

```
aaccagggca aagcaaaata aaagaaactt aatacgttat gccgtaatga agggctacca     60
aaaacgataa tctcaactgt aaacaggtac aatgcggacc cttttgccac aaaacataca    120
tcattcattg ccggaaaaag aaagaagtga agacagcagt gcagccagcc atgttgcgcc    180
aatctaatta tagatgctgg tgccctgagg atgtatctgg agccagccat ggcatcatgc    240
gctaccgccg gatgtaaaat ccgacacgca aaagaaaacc ttcgaggttg cgcacttcgc    300
ccacccatga accacacggt tagtccaaaa ggggcagttc agattccaga tgcgggaatt    360
agcttgctgc caccctcacc tcactaacgc tgcggtgtgc ggatacttca tgctatttat    420
agacgcgcgt gtcggaatca gcacgcgcaa gaaccaaatg ggaaaatcgg aatgggtcca    480
gaactgcttt gagtgctggc tattggcgtc tgatttccgt tttgggaatc ctttgccgcg    540 cgccctctc aaaactccgc acaagtccca gaaagcggga aagaaataaa acgccaccaa    600 aaaaaaaat aaaagccaat cctcgaagcg tgggtggtag gccctggatt atcccgtaca    660
agtatttctc aggagtaaaa aaaccgtttg ttttggaatt ccccatttcg cggccaccta    720
cgccgctatc tttgcaacaa ctatctgcga taactcagca aattttgcat attcgtgttg    780
cagtattgcg ataatgggag tcttacttcc aacataacgg cagaaagaaa tgtgagaaaa    840
ttttgcatcc tttgcctccg ttcaagtata aaagtcggc atgcttgata atctttcttt    900
ccatcctaca ttgttctaat tattcttatt ctcctttatt ctttcctaac ataccaagaa    960
attaatcttc tgtcattcgc ttaaacacta tatcaata                             998
```

<210> SEQ ID NO 34
<211> LENGTH: 700
<212> TYPE: DNA
<213> ORGANISM: Saccharomyces cerevisiae
<220> FEATURE:
<223> OTHER INFORMATION: pGK1
<220> FEATURE:
<223> OTHER INFORMATION: pGK1

<400> SEQUENCE: 34

```
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa agaacaaaaa ctgaaaaaac ccagacacgc    240
```

```
tcgacttcct gtcttcctat tgattgcagc ttccaatttc gtcacacaac aaggtcctag      300
cgacggctca caggttttgt aacaagcaat cgaaggttct ggaatggcgg gaaagggttt      360
agtaccacat gctatgatgc ccactgtgat ctccagagca aagttcgttc gatcgtactg      420
ttactctctc tcttttcaaac agaattgtcc gaatcgtgtg acaacaacag cctgttctca      480
cacactcttt tcttctaacc aagggggtgg tttagtttag tagaacctcg tgaaacttac      540
atttacatat atataaactt gcataaattg gtcaatgcaa gaaatacata tttggtcttt      600
tctaattcgt agttttcaa gttcttagat gctttctttt tctctttttt acagatcatc      660
aaggaagtaa ttatctactt tttacaacaa atataaaaca                           700
```

<210> SEQ ID NO 35
<211> LENGTH: 913
<212> TYPE: DNA
<213> ORGANISM: Saccharomyces cerevisiae
<220> FEATURE:
<223> OTHER INFORMATION: pMDH2
<220> FEATURE:
<223> OTHER INFORMATION: pMDH2

<400> SEQUENCE: 35

```
ccttcgctaa ataataaacc tgaactgtac ttagcgaagc cttcatagca cctacgtaca       60
cgtatatata gacattttac gtaatggaga aactgaggtt tttgttttca ctttttttct      120 ttcttttca ctattgctcg aaccgcctgc gatgagctaa gaaaaaaaag tgaaagaaat       180
catagaaagc aaaaatgaga ttatatagcc cagagccctc ttctggcgcc tgtcccaagg      240
cggaccaaca acaacacttg cccaaaccta agaaaatccc ctcatacttt tccgtttgta      300
tctcctactt tcttacttcc ttttttttctt ctttatttgc ttggtttacc attgaagtcc      360
atttttacta cagacaatag ctagtcattc gctatcttcc gtttgtcact tttttttcaaa      420 tttctcatct atatagcgaa gtacggaaaa gatgtcactt gccggcatct cggccttccc      480
cggccaaatg gactcatcat ctacgatacg gccccttttaa tccgcaatta ctttgcccat      540
tcggccgtag ccgttctaaa gccgccgtgc cttgccccca atactcccct aatgatccgg      600
gaagttccgg ttttttttcct tgtttagtg gcatttgtg ttgcccaagg ttgggaaggt      660
ccgatttgac tttaaggaac tacggaaggt atctaaggtt tctaaaaaca atatacacgc      720
gcgtgcgtag atatataaag ataaagattt atcgatatga gataaagatt gctgcatgat      780
tctccttctg attctttttc cctgtatata ttttctcccc ttctgtataa atcgtacagt      840
cagaagtagt ccagaatata gtgctgcaga ctattacaaa agttcaatac aatatcataa      900
aagttatagt aac                                                         913
```

<210> SEQ ID NO 36
<211> LENGTH: 406
<212> TYPE: DNA
<213> ORGANISM: Saccharomyces cerevisiae
<220> FEATURE:
<223> OTHER INFORMATION: pURA3
<220> FEATURE:
<223> OTHER INFORMATION: pURA3

<400> SEQUENCE: 36

```
ggtacccaaa ccgaagttat ctgatgtaga aaaggattaa agatgctaag agatagtgat       60
gatatttcat aaataatgta attctatata tgttaattac ctttttttgcg aggcatattt      120 atggtgaagg ataagttttg accatcaaag aaggttaatg tggctgtggt ttcagggtcc      180
ataaagcttt tcaattcatc ttttttttttt ttgttctttt ttttgattcc ggtttctttg      240
```

```
aaattttttt gattcggtaa tctccgagca gaaggaagaa cgaaggaagg agcacagact    300
tagattggta tatatacgca tatgtggtgt tgaagaaaca tgaaattgcc cagtattctt    360
aacccaactg cacagaacaa aaacctgcag gaaacgaaga taaatc                   406
```

```
<210> SEQ ID NO 37
<211> LENGTH: 535
<212> TYPE: DNA
<213> ORGANISM: Saccharomyces cerevisiae
<220> FEATURE:
<223> OTHER INFORMATION: pRPLA1
<220> FEATURE:
<223> OTHER INFORMATION: pRPLA1

<400> SEQUENCE: 37
tcaagttgga tactgatctg atctctccgc cctactacca gggaccctca tgattaccgc    60
tcgaatgcga cgtttcctgc ctcataaaac tggcttgaaa atatttattc gctgaacagt    120
agcctagctt ataaaaattt catttaatta atgtaatatg aaaactcaca tgccttctgt    180
ttctaaaatt gtcacagcaa gaaataacat taccatacgt gatcttatta aactctagta    240
tcttgtctaa tacttcattt aaaagaagcc ttaaccctgt agcctcatct atgtctgcta    300
catatcgtga ggtacgaata tcgtaagatg ataccacgca actttgtaat gatttttttt    360
ttttcatttt ttaaagaatg cctttacatg gtatttgaaa aaaatatctt tataaagttt    420
gcgatctctt ctgttctgaa taattttttag taaaagaaat caaaagaata agaaatagt    480 ccgctttgtc caatacaaca gcttaaaccg attatctcta aaataacaag aagaa          535
```

```
<210> SEQ ID NO 38
<211> LENGTH: 400
<212> TYPE: DNA
<213> ORGANISM: Saccharomyces cerevisiae
<220> FEATURE:
<223> OTHER INFORMATION: pSAM4
<220> FEATURE:
<223> OTHER INFORMATION: pSAM4

<400> SEQUENCE: 38 agatttggt gttagatggt actcttgcat atgtaacctt taataaattt tgcaaatcga    60
attcctttgt aacgtgcaaa gcattttata gcctggcgct cgcattgtta agcaacaggc    120
ggtgcggcaa cgttgaaatg tttcacgcag ggttttttac gtactgcacg gcattctgga    180
gtgaaaaaaa atgaaaagta cagctcgaag ttttttgtcc atcggttgta ctttgcagag    240
tattagtcat ttttgatatc agagtactac tatcgaagca ttttacgct tgaataactt    300 gaatatatt gaaagcttag ttcaaccaag ctgaaaagaa ccattattca acataattgg    360
aaatcatttc gttactaaat cgtccgaaaa ttgcagaaaa                          400
```

```
<210> SEQ ID NO 39
<211> LENGTH: 505
<212> TYPE: DNA
<213> ORGANISM: Saccharomyces cerevisiae
<220> FEATURE:
<223> OTHER INFORMATION: pCUP1-1
<220> FEATURE:
<223> OTHER INFORMATION: pCUP1-1

<400> SEQUENCE: 39
cggcaaactt caacgatttc tatgatgcat tttataatta gtaagccgat cccattaccg    60
acatttgggc gctatacgtg catatgttca tgtatgtatc tgtatttaaa acacttttgt    120
```

```
attattttc ctcatatatg tgtataggtt tatacggatg atttaattat tacttcacca    180 cccttatt   caggctgata tcttagcctt gttactagtt agaaaaagac atttttgctg    240
tcagtcactg tcaagagatt cttttgctgg catttcttcc agaagcaaaa agagcgatgc    300
gtcttttccg ctgaaccgtt ccagcaaaaa agactaccaa cgcaatatgg attgtcagaa    360
tcatataaaa gagaagcaaa taactccttg tcttgtatca attgcattat aatatcttct    420
tgttagtgca atatcatata gaagtcatcg aaatagatat taagaaaaac aaactgtaca    480
atcaatcaat caatcatcac ataaa                                          505
```

```
<210> SEQ ID NO 40
<211> LENGTH: 500
<212> TYPE: DNA
<213> ORGANISM: Candida glabrata
<220> FEATURE:
<223> OTHER INFORMATION: pCUP1.Cgla
<220> FEATURE:
<223> OTHER INFORMATION: pCUP1.Cgla

<400> SEQUENCE: 40
```

```
cacaccacac aaccgtcagc accccggctg tacgtctgtg aaggctgcgg tatagacacg     60
gactgcgata cagaactcat gacttatatc tgtagactcc tctgcttcaa tgcgaactcc    120
aggatcaccg aatagcatgc gatgagctgt tgattcttat atataattat ctattgcatt    180
ttttttttaa tgctgcatgg gggggcctag taaatcaccc gtacaagtca cgcgtgagag    240
aaagagaagg gccctttcgt cgtggaagcg tggatcgtga gcgacctgtt tctaaatata    300
gcttttgggt aggatattat attaagtgaa atttattag   agggtaaatg tatgtgaaag    360
ttatgtataa tatgttgcta aattagcgat cgtgaatgca tagaatctaa tcgttataga    420
aaaccgcaac ttgtgctgtt ttgttgtgtt ttcttgtcgt ttttttatat tatttatcta    480
gtattttgct ttagttgtta                                                500
```

```
<210> SEQ ID NO 41
<211> LENGTH: 425
<212> TYPE: DNA
<213> ORGANISM: Saccharomyces bayanus
<220> FEATURE:
<223> OTHER INFORMATION: pCUP1.Sba
<220> FEATURE:
<223> OTHER INFORMATION: pCUP1.Sba

<400> SEQUENCE: 41
```

```
agaaggaggg gtcctattac caatacttgg acgctatacg tgcatatgta catgtacgta     60
tctgtattta aacactttg   tattatttc   tttatatatg tgtataggtt tacatggttg   120
acttttatca ttgtttgtgc acatttgcaa tggccatttt tttgttttg   agaaaggtat   180 tattgctgtc actattcgag atgcttttgc tgacattcct cctagaagcc aaaaggccga    240 tgcgttttt   ccgctgagag gataccagca aaaaaagcta ccagtacaag atgggacggc   300
aaaagcgtat aaagaagaa   gcaaaatgac cagatatgct ttcaatttca tcaatgtttc   360 tttctcccctg ttatgatcca gaagaataat caaaagcaaa acatctattc aatcaatctc   420
ataaa                                                                425
```

```
<210> SEQ ID NO 42
<211> LENGTH: 741
<212> TYPE: DNA
<213> ORGANISM: Artificial Sequence
<220> FEATURE:
<223> OTHER INFORMATION: Synthetic pACU1
```

<220> FEATURE:
<223> OTHER INFORMATION: Synthetic pACU1

<400> SEQUENCE: 42

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg atttttattc caacactaag aaataaattc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tcgaaaaaga cattttttgct gtcagtcact gtcaagagat tcttttgctg gcatttcttc   420
cagaagcaaa aagagcgatg cgtcttttcc gctgaaccgt tccagcaaaa aagactacca   480
acgaattcta attaagttag tcaaggcgcc atcctcatga aaactgtgta acataataac   540
cgaagtgtcg aaaaggtggc accttgtcca attgaacacg ctcgatgaaa aaataagat   600
atatataagg ttaagtaaag cgtctgttag aaaggaagtt tttccttttt cttgctctct   660
tgtcttttca tctactattt ccttcgtgta atacagggtc gtcagataca tagatacaat   720
tctattaccc ccatccatac a                                              741
```

<210> SEQ ID NO 43
<211> LENGTH: 757
<212> TYPE: DNA
<213> ORGANISM: Artificial Sequence
<220> FEATURE:
<223> OTHER INFORMATION: Synthetic pACU2
<220> FEATURE:
<223> OTHER INFORMATION: Synthetic pACU2

<400> SEQUENCE: 43

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg atttttattc caacactaag aaataaattc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccgaatt cgaaaaagac atttttgctg tcagtcactg   360
tcaagagatt cttttgctgg catttcttcc agaagcaaaa agagcgatgc gtcttttccg   420
ctgaaccgtt ccagcaaaaa agactaccaa cgaattccac gtgaagctgt cgatattggg   480
gaactgtggt ggttggcaaa tgactaatta agttagtcaa ggcgccatcc tcatgaaaac   540
tgtgtaacat aataaccgaa gtgtcgaaaa ggtggcacct tgtccaattg aacacgctcg   600
atgaaaaaaa taagatatat ataaggttaa gtaaagcgtc tgttagaaag gaagtttttc   660
cttttcttg ctctcttgtc ttttcatcta ctatttcctt cgtgtaatac agggtcgtca   720
gatacataga tacaattcta ttaccccat ccataca                              757
```

<210> SEQ ID NO 44
<211> LENGTH: 498
<212> TYPE: DNA
<213> ORGANISM: Artificial Sequence
<220> FEATURE:
<223> OTHER INFORMATION: Synthetic pACU3p
<220> FEATURE:
<223> OTHER INFORMATION: Synthetic pACU3p

<400> SEQUENCE: 44

```
ttatattgaa ttttcaaaaa ttcttacttt ttttttggat ggacgcaaag aagtttaata      60
atcatattac atggcattac caccatatac atatccatat ctaatcttac ttatatgttg     120
tggaaatgta aagagcccga attcgaaaaa gacattttg ctgtcagtca ctgtcaagag      180
attcttttgc tggcatttct tccagaagca aaaagagcga tgcgtctttt ccgctgaacc     240
gttccagcaa aaagactac caacgaattc ggatgataat gcgattagtt ttttagcctt      300
atttctgggg taattaatca gcgaagcgat gattttgat ctattaacag atatataaat      360
ggaaaagctg cataaccact ttaactaata cttcaacat tttcagtttg tattacttct      420
tattcaaatg tcataaaagt atcaacaaaa aattgttaat atacctctat actttaacgt     480
caaggagaaa aaactata                                                   498
```

<210> SEQ ID NO 45
<211> LENGTH: 498
<212> TYPE: DNA
<213> ORGANISM: Artificial Sequence
<220> FEATURE:
<223> OTHER INFORMATION: Synthetic pACU4p
<220> FEATURE:
<223> OTHER INFORMATION: Synthetic pACU4p

<400> SEQUENCE: 45

```
ttatattgaa ttttcaaaaa ttcttacttt ttttttggat ggacgcaaag aagtttaata      60
atcatattac atggcattac caccatatac atatccatat ctaatcttac ttatatgttg     120
tggaaatgta aagagcccga attcgttggt agtcttttt gctggaacgg ttcagcggaa      180
aagacgcatc gctcttttg cttctggaag aaatgccagc aaaagaatct cttgacagtg      240
actgacagca aaaatgtctt tttcgaattc ggatgataat gcgattagtt ttttagcctt     300
atttctgggg taattaatca gcgaagcgat gattttgat ctattaacag atatataaat      360
ggaaaagctg cataaccact ttaactaata cttcaacat tttcagtttg tattacttct      420
tattcaaatg tcataaaagt atcaacaaaa aattgttaat atacctctat actttaacgt     480
caaggagaaa aaactata                                                   498
```

<210> SEQ ID NO 46
<211> LENGTH: 530
<212> TYPE: DNA
<213> ORGANISM: Artificial Sequence
<220> FEATURE:
<223> OTHER INFORMATION: Synthetic pACU5
<220> FEATURE:
<223> OTHER INFORMATION: Synthetic pACU5

<400> SEQUENCE: 46

```
ggaggacgaa acaaaaaagt gaaaaaaaat gaaaattttt ttggaaaacc aagaaatgaa      60
ttatatttcc gtgtgagacg acatcgtcga atatgattca gggtaacagt attgatgtaa     120
tcaatttcct acctgaatct aaaattcccg gaattcgaaa aagacatttt tgctgtcagt     180
cactgtcaag agattctttt gctggcattt cttccagaag caaaaagagc gatgcgtctt     240
ttccgctgaa ccgttccagc aaaaaagact accaacgaat tccgagcaga tccgccaggc     300
gtgtatatat agcgtggatg gccaggcaac tttagtgctg acacatacag gcatatatat     360
atgtgtgcga cgacacatga tcatatggca tgcatgtgct ctgtatgtat ataaaactct     420
tgttttcttc ttttctctaa atattctttc cttatacatt aggacctttg cagcataaat     480
tactatactt ctatagacac acaaacacaa atacacacac taaattaata               530
```

<210> SEQ ID NO 47
<211> LENGTH: 867
<212> TYPE: DNA
<213> ORGANISM: Artificial Sequence
<220> FEATURE:
<223> OTHER INFORMATION: Synthetic pACU6
<220> FEATURE:
<223> OTHER INFORMATION: Synthetic pACU6

<400> SEQUENCE: 47

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg atttttattc caacactaag aaataaattc gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tcgaaaaaga cattttttgct gtcagtcact gtcaagagat tcttttgctg gcatttcttc     420
cagaagcaaa aagagcgatg cgtcttttcc gctgaaccgt tccagcaaaa aagactacca     480
acgaattcga aaagacatt tttgctgtca gtcactgtca agagattctt ttgctggcat     540
ttcttccaga gcaaaaaga gcgatgcgtc ttttccgctg aaccgttcca gcaaaaaga     600
ctaccaacga attctaatta agttagtcaa ggcgccatcc tcatgaaaac tgtgtaacat     660
aataaccgaa gtgtcgaaaa ggtggcacct tgtccaattg aacacgctcg atgaaaaaaa     720
taagatatat ataaggttaa gtaaagcgtc tgttagaaag gaagttttc cttttttcttg     780
ctctcttgtc ttttcatcta ctatttcctt cgtgtaatac agggtcgtca gatacataga     840
tacaattcta ttaccccat ccataca                                          867
```

<210> SEQ ID NO 48
<211> LENGTH: 867
<212> TYPE: DNA
<213> ORGANISM: Artificial Sequence
<220> FEATURE:
<223> OTHER INFORMATION: Synthetic pACU7
<220> FEATURE:
<223> OTHER INFORMATION: Synthetic pACU7

<400> SEQUENCE: 48

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg atttttattc caacactaag aaataaattc gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tcgttggtag tcttttttgc tggaacggtt cagcggaaaa gacgcatcgc tcttttttgct     420
tctggaagaa atgccagcaa aagaatctct tgacagtgac tgacagcaaa aatgtctttt     480
tcgaattcgt tggtagtctt ttttgctgga acgttcagc ggaaaagacg catcgctctt     540
tttgcttctg gaagaaatgc cagcaaaaga atctcttgac agtgactgac agcaaaaatg     600
tcttttttcga attctaatta agttagtcaa ggcgccatcc tcatgaaaac tgtgtaacat     660
aataaccgaa gtgtcgaaaa ggtggcacct tgtccaattg aacacgctcg atgaaaaaaa     720
```

| | |
|---|---|
| taagatatat ataaggttaa gtaaagcgtc tgttagaaag gaagttttc cttttcttg | 780 |
| ctctcttgtc ttttcatcta ctatttcctt cgtgtaatac agggtcgtca gatacataga | 840 |
| tacaattcta ttaccccat ccataca | 867 |

<210> SEQ ID NO 49
<211> LENGTH: 1119
<212> TYPE: DNA
<213> ORGANISM: Artificial Sequence
<220> FEATURE:
<223> OTHER INFORMATION: Synthetic pACU8
<220> FEATURE:
<223> OTHER INFORMATION: Synthetic pACU8

<400> SEQUENCE: 49

| | |
|---|---|
| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg attttattc caacactaag aaataattc gccatttctt gaatgtattt | 180 |
| aaagatattt aatgctataa tagacattta atccaattc ttccaacata caatgggagt | 240 |
| ttggccgagt ggtttaaggc gtcagattta ggtggattta acctctaaaa tctctgatat | 300 |
| cttcggatgc aagggttcga atcccttagc tctcattatt ttttgctttt tctcttgaat | 360 |
| tcgaaaaaga cattttgct gtcagtcact gtcaagagat tctttgctg gcatttcttc | 420 |
| cagagcaaa aagagcgatg cgtcttttcc gctgaaccgt tccagcaaaa aagactacca | 480 |
| acgaattcga aaagacatt tttgctgtca gtcactgtca agagattct tgctggcat | 540 |
| ttcttccaga agcaaaaaga gcgatgcgtc tttccgctg aaccgttcca gcaaaaaaga | 600 |
| ctaccaacga attcgaaaaa gacattttg ctgtcagtca ctgtcaagag attctttgc | 660 |
| tggcatttct tccagaagca aaaagagcga tgcgtctttt ccgctgaacc gttccagcaa | 720 |
| aaaagactac caacgaattc gaaaaagaca ttttgctgt cagtcactgt caagagattc | 780 |
| ttttgctggc atttcttcca gaagcaaaaa gagcgatgcg tcttttccgc tgaaccgttc | 840 |
| cagcaaaaaa gactaccaac gaattctaat taagttagtc aaggcgccat cctcatgaaa | 900 |
| actgtgtaac ataataaccg aagtgtcgaa aaggtggcac cttgtccaat tgaacacgct | 960 |
| cgatgaaaaa aataagatat atataaggtt aagtaaagcg tctgttagaa aggaagtttt | 1020 |
| tccttttct tgctctcttg tcttttcatc tactatttcc ttcgtgtaat acagggtcgt | 1080 |
| cagatacata gatacaattc tattaccccc atccataca | 1119 |

<210> SEQ ID NO 50
<211> LENGTH: 624
<212> TYPE: DNA
<213> ORGANISM: Artificial Sequence
<220> FEATURE:
<223> OTHER INFORMATION: Synthetic pACU9
<220> FEATURE:
<223> OTHER INFORMATION: Synthetic pACU9

<400> SEQUENCE: 50

| | |
|---|---|
| tatagttttt tctccttgac gttaaagtat agaggtatat taacaattttt tgttgatac | 60 |
| ttttatgaca tttgaataag aagtaataca aactgaaaat gttgaaagta ttagttaaag | 120 |
| tggttatgca gcttttccat ttatatatct gttaatagat caaaaatcat cgcttcgctg | 180 |
| attaattacc ccagaaataa ggctaaaaaa ctaatcgcat tatcatccga attcgaaaaa | 240 |
| gacattttg ctgtcagtca ctgtcaagag attctttgc tggcatttct tccagaagca | 300 |
| aaaagagcga tgcgtcttt ccgctgaacc gttccagcaa aaagactac caacgaattc | 360 |

```
gaaaaagaca ttttgctgt cagtcactgt caagagattc ttttgctggc atttcttcca    420
gaagcaaaaa gagcgatgcg tcttttccgc tgaaccgttc cagcaaaaaa gactaccaac    480
gaattcgggc tctttacatt tccacaacat ataagtaaga ttagatatgg atatgtatat    540
ggtggtaatg ccatgtaata tgattattaa acttctttgc gtccatccaa aaaaaagta     600 agaatttttg aaaattcaat ataa                                           624
```

<210> SEQ ID NO 51
<211> LENGTH: 876
<212> TYPE: DNA
<213> ORGANISM: Artificial Sequence
<220> FEATURE:
<223> OTHER INFORMATION: Synthetic pACU10p
<220> FEATURE:
<223> OTHER INFORMATION: Synthetic pACU10p

<400> SEQUENCE: 51

```
ttatattgaa tttcaaaaa ttcttacttt tttttggat ggacgcaaag aagtttaata      60
atcatattac atggcattac caccatatac atatccatat ctaatcttac ttatatgttg   120
tggaaatgta aagagcccga attggttggt agtctttttt gctggaacgg ttcagcggaa   180
aagacgcatc gctctttttg cttctggaag aaatgccagc aaaagaatct cttgacagtg   240
actgacagca aaaatgtctt tttcgaattc gttggtagtc ttttttgctg gaacggttca   300
gcggaaaaga cgcatcgctc ttttttgcttc tggaagaaat gccagcaaaa gaatctcttg   360
acagtgactg acagcaaaaa tgtcttttc gaattcgttg gtagtctttt ttgctggaac    420
ggttcagcgg aaaagacgca tcgctctttt tgcttctgga gaaatgcca gcaaaagaat   480 ctcttgacag tgactgacag caaaaatgtc ttttcgaat cgttggtag tcttttttgc    540 tggaacggtt cagcggaaaa gacgcatcgc tctttttgct tctggaagaa atgccagcaa   600
aagaatctct tgacagtgac tgacagcaaa aatgtcttt tccaattcgg atgataatgc   660
gattagtttt ttagccttat ttctggggta attaatcagc gaagcgatga ttttgatct    720 attaacagat atataaatgg aaaagctgca taaccacttt aactaatact ttcaacattt   780
tcagtttgta ttacttctta ttcaaatgtc ataaaagtat caacaaaaaa ttgttaatat   840
acctctatac tttaacgtca aggagaaaaa actata                              876
```

<210> SEQ ID NO 52
<211> LENGTH: 633
<212> TYPE: DNA
<213> ORGANISM: Artificial Sequence
<220> FEATURE:
<223> OTHER INFORMATION: Synthetic pACU11
<220> FEATURE:
<223> OTHER INFORMATION: Synthetic pACU11

<400> SEQUENCE: 52

```
gctcagcatc tgcttcttcc caaagatgaa cgcggcgtta tgtcactaac gacgtgcacc     60
aacttgcggg aattcgaaaa agacattttt gctgtcagtc actgtcaaga gattcttttg   120
ctggcatttc ttccagaagc aaaaagagcg atgcgtcttt tccgctgaac cgttccagca   180
aaaaagacta ccaacgaatt ccaccgcacg ccttttttct gaagcccact ttcgtggact   240
ttgccatata tgcaaaattc atgaagtgtg ataccaagtc agcatacacc tcactagggt   300
agtttctttg gttgtattga tcatttggtt catcgtggtt cattaatttt ttttctccat   360
tgctttctgg ctttgatctt actatcattt ggattttgt cgaaggttgt agaattgtat   420
```

```
gtgacaagtg gcaccaagca tatataaaaa aaaaaagcat tatcttccta ccagagttga      480
ttgttaaaaa cgtatttata gcaaacgcaa ttgtaattaa ttcttatttt gtatcttttc      540
ttcccttgtc tcaatctttt atttttattt tattttttctt ttcttagttt ctttcataac    600
accaagcaac taatactata acatacaata ata                                   633

<210> SEQ ID NO 53
<211> LENGTH: 1119
<212> TYPE: DNA
<213> ORGANISM: Artificial Sequence
<220> FEATURE:
<223> OTHER INFORMATION: Synthetic pACU12
<220> FEATURE:
<223> OTHER INFORMATION: Synthetic pACU12

<400> SEQUENCE: 53
ttacattatc aatccttgcg tttcagcttc cactaattta gatgactatt tctcatcatt       60
tgcgtcatct tctaacaccg tatatgataa tatactagta acgtaaatac tagttagtag      120
atgatagttg atttttattc caacactaag aaataaattt gccatttctt gaatgtattt      180
aaagatattt aatgctataa tagacattta aatccaattc ttccaacata caatgggagt      240
ttggccgagt ggtttaaggc gtcagattta ggtggattta acctctaaaa tctctgatat      300
cttcggatgc aagggttcga atcccttagc tctcattatt ttttgctttt tctcttgaat      360
tggttggtag tcttttttgc tggaacggtt cagcggaaaa gacgcatcgc tcttttttgct    420 tctggaagaa atgccagcaa aagaatctct tgacagtgac tgacagcaaa aatgtctttt      480
tcgaattcgt tggtagtctt ttttgctgga acggttcagc ggaaaagacg catcgctctt      540
tttgcttctg gaagaaatgc cagcaaaaga atctcttgac agtgactgac agcaaaaatg      600 tcttttttcga attcgttggt agtcttttttt gctggaacgg ttcagcggaa aagacgcatc    660 gctcttttttg cttctggaag aaatgccagc aaaagaatct cttgacagtg actgacagca    720
aaaatgtctt tttcgaattc gttggtagtc ttttttgctg gaacggttca gcggaaaaga      780
cgcatcgctc ttttttgcttc tggaagaaat gccagcaaaa gaatctcttg acagtgactg    840
acagcaaaaa tgtcttttttc caattctaat taagttagtc aaggcgccat cctcatgaaa    900
actgtgtaac ataataaccg aagtgtcgaa aaggtggcac cttgtccaat gaacacgct       960 cgatgaaaaa aataagatat atataaggtt aagtaaagcg tctgttagaa aggaagtttt    1020 tccttttttct tgctctcttg tcttttcatc tactatttcc ttcgtgtaat acagggtcgt    1080
cagatacata gatacaattc tattaccccc atccataca                            1119

<210> SEQ ID NO 54
<211> LENGTH: 1497
<212> TYPE: DNA
<213> ORGANISM: Artificial Sequence
<220> FEATURE:
<223> OTHER INFORMATION: Synthetic pACU13
<220> FEATURE:
<223> OTHER INFORMATION: Synthetic pACU13

<400> SEQUENCE: 54
ttacattatc aatccttgcg tttcagcttc cactaattta gatgactatt tctcatcatt       60
tgcgtcatct tctaacaccg tatatgataa tatactagta acgtaaatac tagttagtag      120
atgatagttg atttttattc caacactaag aaataaattt gccatttctt gaatgtattt      180
aaagatattt aatgctataa tagacattta aatccaattc ttccaacata caatgggagt      240
ttggccgagt ggtttaaggc gtcagattta ggtggattta acctctaaaa tctctgatat      300
```

```
cttcggatgc aagggttcga atcccttagc tctcattatt ttttgctttt tctcttgaat    360
tggttggtag tcttttttgc tggaacggtt cagcggaaaa gacgcatcgc tcttttttgct   420 tctggaagaa atgccagcaa aagaatctct tgacagtgac tgacagcaaa aatgtctttt    480
tcgaattcgt tggtagtctt ttttgctgga acggttcagc ggaaaagacg catcgctctt    540
tttgcttctg gaagaaatgc cagcaaaaga atctcttgac agtgactgac agcaaaaatg   600 tcttttcga attcgttggt agtctttttt gctggaacgg ttcagcggaa aagacgcatc    660 gctcttttg cttctggaag aaatgccagc aaaagaatct cttgacagtg actgacagca    720
aaaatgtctt tttcgaattc gttggtagtc ttttttgctg gaacggttca gcggaaaaga   780
cgcatcgctc ttttgcttc tggaagaaat gccagcaaaa gaatctcttg acagtgactg    840
acagcaaaaa tgtctttttc gaattcgttg gtagtctttt ttgctggaac ggttcagcgg    900
aaaagacgca tcgctctttt gcttctgga agaaatgcca gcaaaagaat ctcttgacag    960
tgactgacag caaaaatgtc tttttcgaat tcgttggtag tcttttttgc tggaacggtt   1020
cagcggaaaa gacgcatcgc tcttttgct tctggaagaa atgccagcaa aagaatctct   1080
tgacagtgac tgacagcaaa aatgtctttt tcgaattcgt tggtagtctt ttttgctgga   1140
acggttcagc ggaaaagacg catcgctctt tttgcttctg gaagaaatgc cagcaaaaga   1200
atctcttgac agtgactgac agcaaaaatg tcttttccca attctaatta agttagtcaa    1260
ggcgccatcc tcatgaaaac tgtgtaacat aataaccgaa gtgtcgaaaa ggtggcacct    1320
tgtccaattg aacacgctcg atgaaaaaaa taagatatat ataaggttaa gtaaagcgtc    1380
tgttagaaag gaagtttttc cttttcttg ctctcttgtc ttttcatcta ctatttcctt     1440
cgtgtaatac agggtcgtca gatacataga tacaattcta ttaccccat ccataca       1497

<210> SEQ ID NO 55
<211> LENGTH: 1011
<212> TYPE: DNA
<213> ORGANISM: Artificial Sequence
<220> FEATURE:
<223> OTHER INFORMATION: Synthetic pACU14
<220> FEATURE:
<223> OTHER INFORMATION: Synthetic pACU14

<400> SEQUENCE: 55
gctcagcatc tgcttcttcc caagatgaa cgcggcgtta tgtcactaac gacgtgcacc     60
aacttgcggg aattggaaaa agacattttt gctgtcagtc actgtcaaga gattcttttg   120
ctggcatttc ttccagaagc aaaaagagcg atgcgtcttt ccgctgaac cgttccagca    180 aaaaagacta ccaacgaatt cgaaaaagac attttgctg tcagtcactg tcaagagatt   240
cttttgctgg catttcttcc agaagcaaaa agagcgatgc gtcttttccg ctgaaccgtt    300
ccagcaaaaa agactaccaa cgaattcgaa aaagacattt tgctgtcag tcactgtcaa    360 gagattcttt tgctggcatt tcttccagaa gcaaaagag cgatgcgtct tttccgctga    420
accgttccag caaaaaagac taccaacgaa ttcgaaaaag acattttgc tgtcagtcac    480 tgtcaagaga ttcttttgct ggcatttctt ccagaagcaa aaagagcgat gcgtcttttc    540
cgctgaaccg ttcagcaaa aaagactacc aaccaattcc accgcacgcc ttttttctga    600
agcccacttt cgtggacttt gccatatatg caaaattcat gaagtgtgat accaagtcag   660
catacacctc actagggtag tttctttggt tgtattgatc atttggttca tcgtggttca    720 ttaattttt ttctccattg ctttctggct ttgatcttac tatcatttgg attttgtcg    780
```

```
aaggttgtag aattgtatgt gacaagtggc accaagcata tataaaaaaa aaaagcatta    840
tcttcctacc agagttgatt gttaaaaacg tatttatagc aaacgcaatt gtaattaatt    900
cttattttgt atcttttctt cccttgtctc aatcttttat ttttatttta tttttctttt    960
cttagtttct ttcataacac caagcaacta atactataac atacaataat a           1011
```

<210> SEQ ID NO 56
<211> LENGTH: 398
<212> TYPE: DNA
<213> ORGANISM: Artificial Sequence
<220> FEATURE:
<223> OTHER INFORMATION: Synthetic pACU15
<220> FEATURE:
<223> OTHER INFORMATION: Synthetic pACU15

<400> SEQUENCE: 56

```
tatagttttt tctccttgac gttaaagtat agaggtatat taacaatttt ttgttgatac     60
ttttatgaca tttgaataag aagtaataca aactgaaaat gttgaaagta ttagttaaag    120
tggttatgca gcttttccat ttatatatct gttaatagat caaaaatcat cgcttcgctg    180
attaattacc ccagaaataa ggctaaaaaa ctaatcgcat tatcatccga attcgttggt    240 agtcttttt gctggaacgg ttcagcggaa aagacgcatc gctctttttg cttctggaag    300
aaatgccagc aaaagaatct cttgacagtg actgacagca aaaatgtctt tttcgaattc    360
gggctcttta catttccaca acatataagt aagattag                             398
```

<210> SEQ ID NO 57
<211> LENGTH: 428
<212> TYPE: DNA
<213> ORGANISM: Artificial Sequence
<220> FEATURE:
<223> OTHER INFORMATION: Synthetic pGAL/CUP1p
<220> FEATURE:
<223> OTHER INFORMATION: Synthetic pGAL/CUP1p

<400> SEQUENCE: 57

```
ttatattgaa ttttcaaaaa ttcttacttt ttttttggat ggacgcaaag aagtttaata     60
atcatattac atggcattac caccatatac atatccatat ctaatcttac ttatatgttg    120
tggaaatgta aagagcccga attcgaaaaa gacattttg ctgtcagtca ctgtcaagag    180
attcttttgc tggcatttct tccagaagca aaaagagcga tgcgtctttt ccgctgaacc    240
gttccagcaa aaaagactac caacgcaata tggattgtca gaatcatata aaagagaagc    300
aaataactcc ttgtcttgta tcaattgcat tataatatct tcttgttagt gcaatatcat    360
atagaagtca tcgaaataga tattaagaaa aacaaactgt acaatcaatc aatcaatcat    420
cacataaa                                                             428
```

<210> SEQ ID NO 58
<211> LENGTH: 518
<212> TYPE: DNA
<213> ORGANISM: Saccharomyces cerevisiae
<220> FEATURE:
<223> OTHER INFORMATION: pCRS5
<220> FEATURE:
<223> OTHER INFORMATION: pCRS5

<400> SEQUENCE: 58

```
gtggacgaaa agacataact gcagaagtac agctgccttt atttcttgtg gtcatttatt     60
gcttttattt tcaagtcaga tatacaagaa atcaaatcc catcgtcaac gtcacgtata    120
aacgattaat ttacagtaat accatactct accaacatta ttttagtccg acgttcagtc    180
```

```
ctgtaggtgt tccaaatcct tctggcattg acttctgtgc agaaacccct caaaatgagt    240
tccactttac gtcagatcgc ataacaaccg gtcatatatt ttttctttt gctaaacccc     300 ctactgcaag cacttttaag aaaaagaaca ataaatgcgt ctttattgct gtgtggaagt    360
gatttttgtc tttcggacaa aaaaggata gggatgcgag agggctgtga agtagtgatc     420
aagcggggcc tatataagaa gggcgcacat cgtcccccct aagaatagcg aagcgatatt    480
acactgaaca ctacaatgtc aaatagtact caataaat                            518
```

<210> SEQ ID NO 59
<211> LENGTH: 510
<212> TYPE: DNA
<213> ORGANISM: Saccharomyces cerevisiae
<220> FEATURE:
<223> OTHER INFORMATION: pCHA1
<220> FEATURE:
<223> OTHER INFORMATION: pCHA1

<400> SEQUENCE: 59

```
gatctctgct gacgttgtat ccacagatct aattgcaaga tagcctcttg cgaccttatt    60
aaaagcctct ccgtgatatc ctctagggct tgggttgcca ttaatcgatg tgtccttgtt    120
tccttatgcg agctgtttct tatctatctt atggtcccat tctttactgc actgtttaca    180
ttttgatcaa ttgcgaaatg ttcctactat ttttctttt ctcttttcgc gagtactaat     240
caccgcgaac ggaaactaat gagtcctctg cgcggagaca tgattccgca tgggcggctc    300
ctgttaagcc ccagcggaaa tgtaattcca ctgagtgtca ttaaatagtg ccaaagcttt    360
atcaaattgt ttgcgatgag ataagataaa agggacaata tgaggaggaa cacaggtata    420
taaatatcgc caaataaaag gaaatgtttt atacagtttt ctcttttta agtgctggat     480 agacaagaga caggaaaatt aaccagcgag                                     510
```

<210> SEQ ID NO 60
<211> LENGTH: 601
<212> TYPE: DNA
<213> ORGANISM: Saccharomyces cerevisiae
<220> FEATURE:
<223> OTHER INFORMATION: pCTR1
<220> FEATURE:
<223> OTHER INFORMATION: pCTR1

<400> SEQUENCE: 60

```
caagtccgat tgttcctctt caggagcttc ctgaaccaaa cttttccgc aaggccgcat     60 tttgaaccgt attttgctcg ttccagcctt tccacgtttt tgttatctaa gcaacttggc    120
acatttccct actatactac aaaccgatac gtaaatactt ccctaaatag catatgaatt    180
attcagtaat ttttaaggat cgaaactgca cctcaactat tcgttactgt ggttatgttc    240
tcatgtattg atgcaaatca tgggatattt gctcaagacg acggtaaaat gagcaaaaat    300
ggcacgatcc tgaaaagagc acttttcaag attcgggcta caaatgcaa cataaaaaat    360 gttgtattgt catctcgaca gggtcttgta tgttttattc ctcttatgat tagttcacat    420
tagtaaaaca gatacgcagt gtgctcttaa taaacaacta ctccatagct ttatttgcat    480
aacaaaactt ttaagcacaa acttaaacag gtggagtaat agttcggcgg cgactcaaat    540
tacatttgtt ggaagaatcg aatagaaaat aaaaaaaagt gtattatatt tgacattcaa    600
a                                                                    601
```

<210> SEQ ID NO 61

<211> LENGTH: 522
<212> TYPE: DNA
<213> ORGANISM: Saccharomyces cerevisiae
<220> FEATURE:
<223> OTHER INFORMATION: pCTR3
<220> FEATURE:
<223> OTHER INFORMATION: pCTR3

<400> SEQUENCE: 61

```
gatgtgatga caaaacctct tccgataaaa acatttaaac tattaacaaa caaatggatt    60
cattagatct attacattat gggtggtatg ttggaataaa aatcaactat catctactaa   120
ctagtattta cgttactagt atattatcat atacggtgtt agaagatgac gcaaatgatg   180
agaaatagtc atctaaatta gtggaagctg aaacgcaagg attgataatg taataggatc   240
aatgaatatt aacatataaa acgatgataa taatatttat agaattgtgt agaattgcag   300
attccctttt atggattcct aaatcctcca ggagaacttc tagtatatct acatacctaa   360
tattattgcc ttattaaaaa tggaatccca acaattacat caaaatccac attctcttca   420
cttctccgat agacttgtaa tttatcttat ttcatttcct aacactttga tcgaagaaga   480
gggataacaa cagacgaaaa cacatttaag ggctatacaa ag                      522
```

<210> SEQ ID NO 62
<211> LENGTH: 675
<212> TYPE: DNA
<213> ORGANISM: Artificial Sequence
<220> FEATURE:
<223> OTHER INFORMATION: Synthetic pCUR1
<220> FEATURE:
<223> OTHER INFORMATION: Synthetic pCUR1

<400> SEQUENCE: 62

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tgtcatggga tatttgctca agacgacggt aaaatgagca aatatggcac gatcctcaat   420
tctaattaag ttagtcaagg cgccatcctc atgaaaactg tgtaacataa taaccgaagt   480
gtcgaaaagg tggcaccttg tccaattgaa cacgctcgat gaaaaaaata agatatatat   540
aaggttaagt aaagcgtctg ttagaaagga agttttttcct ttttcttgct ctcttgtctt   600
ttcatctact atttccttcg tgtaatacag ggtcgtcaga tacatagata caattctatt   660
accccccatcc ataca                                                   675
```

<210> SEQ ID NO 63
<211> LENGTH: 674
<212> TYPE: DNA
<213> ORGANISM: Artificial Sequence
<220> FEATURE:
<223> OTHER INFORMATION: Synthetic pCUR2
<220> FEATURE:
<223> OTHER INFORMATION: Synthetic pCUR2

<400> SEQUENCE: 63

```
ttacattatc aatccttgcg tttcagcttc cactaattta gatgactatt tctcatcatt    60
tgcgtcatct tctaacaccg tatatgataa tatactagta acgtaaatac tagttagtag   120
```

```
atgatagttg attttttattc caacactaag aaataatttc gccatttctt gaatgtatttt    180 aaagatatttt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgatt    360
gaggatcgtg ccatatttgc tcattttacc gtcgtcttga gcaaatatcc catgacaatt    420
ctaattaagt tagtcaaggc gccatcctca tgaaaactgt gtaacataat aaccgaagtg    480
tcgaaaaggt ggcaccttgt ccaattgaac acgctcgatg aaaaaaataa gatatatata    540
aggttaagta aagcgtctgt tagaaaggaa gttttttcctt tttcttgctc tcttgtctttt    600 tcatctacta tttccttcgt gtaatacagg gtcgtcagat acatagatac aattctatta    660
cccccatcca taca                                                       674

<210> SEQ ID NO 64
<211> LENGTH: 794
<212> TYPE: DNA
<213> ORGANISM: Artificial Sequence
<220> FEATURE:
<223> OTHER INFORMATION: Synthetic pCUR3
<220> FEATURE:
<223> OTHER INFORMATION: Synthetic pCUR3

<400> SEQUENCE: 64
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttttattc caacactaag aaataatttc gccatttctt gaatgtatttt   180 aaagatatttt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
taggatcgtg ccatatttgc tcattttacc gtcgtcttga gcaaatatcc catgacaatt    420
gaggatcgtg ccatatttgc tcattttacc gtcgtcttga gcaaatatcc catgacaatt    480
gaggatcgtg ccatatttgc tcattttacc gtcgtcttga gcaaatatcc catgacaatt    540
ctaattaagt tagtcaaggc gccatcctca tgaaaactgt gtaacataat aaccgaagtg    600
tcgaaaaggt ggcaccttgt ccaattgaac acgctcgatg aaaaaaataa gatatatata    660
aggttaagta aagcgtctgt tagaaaggaa gttttttcctt tttcttgctc tcttgtctttt    720 tcatctacta tttccttcgt gtaatacagg gtcgtcagat acatagatac aattctatta    780
cccccatcca taca                                                       794

<210> SEQ ID NO 65
<211> LENGTH: 850
<212> TYPE: DNA
<213> ORGANISM: Artificial Sequence
<220> FEATURE:
<223> OTHER INFORMATION: Synthetic pCUR4
<220> FEATURE:
<223> OTHER INFORMATION: Synthetic pCUR4

<400> SEQUENCE: 65
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttttattc caacactaag aaataatttc gccatttctt gaatgtatttt   180
```

-continued

| | |
|---|---|
| aaagatattt aatgctataa tagacattta aatccaattc ttccaacata caatgggagt | 240 |
| ttggccgagt ggtttaaggc gtcagattta ggtggattta acctctaaaa tctctgatat | 300 |
| cttcggatgc aagggttcga atcccttagc tctcattatt ttttgctttt tctcttgaat | 360 |
| tgtcatggga tatttgctca agacgacggt aaaatgagca atatggcac gatcctcaat | 420 |
| tgtcatggga tatttgctca agacgacggt aaaatgagca atatggcac gatcctcaat | 480 |
| gtcatgggat atttgctcaa gacgacggta aatgagcaa atatggcacg atcctcaatt | 540 |
| gtcatgggat atttgctcaa gacgacggta aatgagcaa atatcccatg acaattctaa | 600 |
| ttaagttagt caaggcgcca tcctcatgaa aactgtgtaa cataataacc gaagtgtcga | 660 |
| aaaggtggca ccttgtccaa ttgaacacgc tcgatgaaaa aaataagata tatataaggt | 720 |
| taagtaaagc gtctgttaga aaggaagttt ttccttttc ttgctctctt gtcttttcat | 780 |
| ctactatttc cttcgtgtaa tacagggtcg tcagatacat agatacaatt ctattacccc | 840 |
| catccataca | 850 |

<210> SEQ ID NO 66
<211> LENGTH: 491
<212> TYPE: DNA
<213> ORGANISM: Artificial Sequence
<220> FEATURE:
<223> OTHER INFORMATION: Synthetic pCUR5p
<220> FEATURE:
<223> OTHER INFORMATION: Synthetic pCUR5p

<400> SEQUENCE: 66

| | |
|---|---|
| ttatattgaa ttttcaaaaa ttcttacttt ttttttggat ggacgcaaag aagtttaata | 60 |
| atcatattac atggcattac caccatatac atatccatat ctaatcttac ttatatgttg | 120 |
| tggaaatgta aagagcccga attgtcatgg gatatttgct caagacgacg gtaaaatgag | 180 |
| caaatatggc acgatcctca attgtcatgg gatatttgct caagacgacg gtaaaatgag | 240 |
| caaatatggc acgatcccaa ttcggatgat aatgcgatta gttttttagc cttatttctg | 300 |
| gggtaattaa tcagcgaagc gatgattttt gatctattaa cagatatata aatggaaaag | 360 |
| ctgcataacc actttaacta atactttcaa cattttcagt ttgtattact tcttattcaa | 420 |
| atgtcataaa agtatcaaca aaaaattgtt aatataccctc tatactttaa cgtcaaggag | 480 |
| aaaaaactat a | 491 |

<210> SEQ ID NO 67
<211> LENGTH: 833
<212> TYPE: DNA
<213> ORGANISM: Artificial Sequence
<220> FEATURE:
<223> OTHER INFORMATION: Synthetic pCUR6
<220> FEATURE:
<223> OTHER INFORMATION: Synthetic pCUR6

<400> SEQUENCE: 67

| | |
|---|---|
| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg attttattc caacactaag aaataaattc gccatttctt gaatgtattt | 180 |
| aaagatattt aatgctataa tagacattta aatccaattc ttccaacata caatgggagt | 240 |
| ttggccgagt ggtttaaggc gtcagattta ggtggattta acctctaaaa tctctgatat | 300 |
| cttcggatgc aagggttcga atcccgaatt gaggatcgtg ccatatttgc tcatttttacc | 360 |
| gtcgtcttga gcaaatatcc catgacaatt gaggatcgtg ccatatttgc tcatttttacc | 420 |

```
gtcgtcttga gcaaatatcc catgacaatt gaggatcgtg ccatatttgc tcattttacc    480
gtcgtcttga gcaaatatcc catgacaatt catgatcgca aaatggcaaa tggcacgtga    540
agctgtcgat attggggaac tgtggtggtt ggcaaatgac taattaagtt agtcaaggcg    600
ccatcctcat gaaaactgtg taacataata accgaagtgt cgaaaggtg gcaccttgtc     660 caattgaaca cgctcgatga aaaaaataag atatatataa ggttaagtaa agcgtctgtt    720
agaaaggaag ttttccttt tcttgctct cttgtctttt catctactat ttccttcgtg      780
taatacaggg tcgtcagata catagataca attctattac ccccatccat aca           833
```

<210> SEQ ID NO 68
<211> LENGTH: 803
<212> TYPE: DNA
<213> ORGANISM: Artificial Sequence
<220> FEATURE:
<223> OTHER INFORMATION: Synthetic pCUR7
<220> FEATURE:
<223> OTHER INFORMATION: Synthetic pCUR7

<400> SEQUENCE: 68

```
gtgagtaagg aaagagtgag gaactatcgc atacctgcat ttaaagatgc cgatttgggc    60
gcgaatcctt tattttggct tcaccctcat actattatca gggccagaaa aaggaagtgt    120
ttccctcctt cttgaattga tgttaccctc ataaagcacg tggcctctta tcgagaaaga   180
aattaccgtc gctcgtgatt tgtttgcaaa aagaacaaaa ctgaattcag gatcgtgcca   240
tatttgctca ttttaccgtc gtcttgagca aatatcccat gacaattgag gatcgtgcca   300
tatttgctca ttttaccgtc gtcttgagca aatatcccat gagaattctt cctgtcttcc   360
tattgattgc agcttccaat ttcgtcacac aacaaggtcc tagcgacggc tcacaggttt   420
tgtaacaagc aatcgaaggt tctggaatgg cgggaaaggg tttagtacca catgctatga   480
tgcccactgt gatctccaga gcaaagttcg ttcgatcgta ctgttactct ctctctttca   540
aacagaattg tccgaatcgt gtgacaacaa cagcctgttc tcacacactc ttttcttcta   600
accaaggggg tggtttagtt tagtagaacc tcgtgaaact tacatttaca tatatataaa   660
cttgcataaa ttggtcaatg caagaaatac atatttggtc ttttctaatt cgtagttttt   720
caagttctta gatgctttct ttttctcttt tttacagatc atcaaggaag taattatcta   780 cttttttacaa caaatataaa aca                                         803
```

<210> SEQ ID NO 69
<211> LENGTH: 863
<212> TYPE: DNA
<213> ORGANISM: Artificial Sequence
<220> FEATURE:
<223> OTHER INFORMATION: Synthetic pCUR8
<220> FEATURE:
<223> OTHER INFORMATION: Synthetic pCUR8

<400> SEQUENCE: 69

```
gtgagtaagg aaagagtgag gaactatcgc atacctgcat ttaaagatgc cgatttgggc    60
gcgaatcctt tattttggct tcaccctcat actattatca gggccagaaa aaggaagtgt    120
ttccctcctt cttgaattga tgttaccctc ataaagcacg tggcctctta tcgagaaaga   180
aattaccgtc gctcgtgatt tgtttgcaaa aagaacaaaa ctgaattcag gatcgtgcca   240
tatttgctca ttttaccgtc gtcttgagca aatatcccat gacaattgag gatcgtgcca   300
tatttgctca ttttaccgtc gtcttgagca aatatcccat gacaattgag gatcgtgcca   360
```

```
tatttgctca ttttaccgtc gtcttgagca aatatcccat gagaattctt cctgtcttcc    420
tattgattgc agcttccaat ttcgtcacac aacaaggtcc tagcgacggc tcacaggttt    480
tgtaacaagc aatcgaaggt tctggaatgg cgggaaaggg tttagtacca catgctatga    540
tgcccactgt gatctccaga gcaaagttcg ttcgatcgta ctgttactct ctctctttca    600
aacagaattg tccgaatcgt gtgacaacaa cagcctgttc tcacacactc ttttcttcta    660
accaaggggg tggtttagtt tagtagaacc tcgtgaaact tacatttaca tatatataaa    720
cttgcataaa ttggtcaatg caagaaatac atatttggtc ttttctaatt cgtagttttt    780
caagttctta gatgctttct ttttctcttt tttacagatc atcaaggaag taattatcta    840 cttttttacaa caaatataaa aca                                           863

<210> SEQ ID NO 70
<211> LENGTH: 863
<212> TYPE: DNA
<213> ORGANISM: Artificial Sequence
<220> FEATURE:
<223> OTHER INFORMATION: Synthetic pCUR9
<220> FEATURE:
<223> OTHER INFORMATION: Synthetic pCUR9

<400> SEQUENCE: 70
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctgaattctt cctgtcttcc    420
tattgattgc agcttccaat ttcgtcacac aacaaggtcc tagcgacggc tcacaggttt    480
tgtaacaagc aatcgaaggt tctggaatgg cgggaaaggg tttagtacca catgctatga    540
tgcccactgt gatctccaga gcaaagttcg ttcgatcgta ctgttactct ctctctttca    600
aacagaattg tccgaatcgt gtgacaacaa cagcctgttc tcacacactc ttttcttcta    660
accaaggggg tggtttagtt tagtagaacc tcgtgaaact tacatttaca tatatataaa    720
cttgcataaa ttggtcaatg caagaaatac atatttggtc ttttctaatt cgtagttttt    780
caagttctta gatgctttct ttttctcttt tttacagatc atcaaggaag taattatcta    840 cttttttacaa caaatataaa aca                                           863

<210> SEQ ID NO 71
<211> LENGTH: 923
<212> TYPE: DNA
<213> ORGANISM: Artificial Sequence
<220> FEATURE:
<223> OTHER INFORMATION: Synthetic pCUR10
<220> FEATURE:
<223> OTHER INFORMATION: Synthetic pCUR10

<400> SEQUENCE: 71
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
```

```
tgctcaagac gacggtaaaa tgagcaaata tggcacgatc ctcaattgtc atgggatatt        300
tgctcaagac gacggtaaaa tgagcaaata tggcacgatc ctcaattgtc atgggatatt        360
tgctcaagac gacggtaaaa tgagcaaata tggcacgatc ctcaattgtc atgggatatt        420
tgctcaagac gacggtaaaa tgagcaaata tggcacgatc ctgaattctt cctgtcttcc        480
tattgattgc agcttccaat ttcgtcacac aacaaggtcc tagcgacggc tcacaggttt        540
tgtaacaagc aatcgaaggt tctggaatgg cgggaaaggg tttagtacca catgctatga        600
tgcccactgt gatctccaga gcaaagttcg ttcgatcgta ctgttactct ctctctttca        660
aacagaattg tccgaatcgt gtgacaacaa cagcctgttc tcacacactc ttttcttcta        720
accaaggggg tggtttagtt tagtagaacc tcgtgaaact tacatttaca tatatataaa        780
cttgcataaa ttggtcaatg caagaaatac atatttggtc ttttctaatt cgtagttttt        840
caagttctta gatgctttct ttttctcttt tttacagatc atcaaggaag taattatcta        900 cttttttacaa caaatataaa aca        923

<210> SEQ ID NO 72
<211> LENGTH: 983
<212> TYPE: DNA
<213> ORGANISM: Artificial Sequence
<220> FEATURE:
<223> OTHER INFORMATION: Synthetic pCUR11
<220> FEATURE:
<223> OTHER INFORMATION: Synthetic pCUR11

<400> SEQUENCE: 72
gtgagtaagg aaagagtgag gaactatcgc atacctgcat ttaaagatgc cgatttgggc         60
gcgaatcctt tattttggct tcaccctcat actattatca gggccagaaa aaggaagtgt        120
ttccctcctt cttgaattga tgttaccctc ataaagcacg tggcctctta tcgagaaaga        180
aattaccgtc gctcgtgatt tgtttgcaaa aagaacaaaa ctgaattctc atgggatatt        240
tgctcaagac gacggtaaaa tgagcaaata tggcacgatc ctcaattgtc atgggatatt        300
tgctcaagac gacggtaaaa tgagcaaata tggcacgatc ctcaattgtc atgggatatt        360
tgctcaagac gacggtaaaa tgagcaaata tggcacgatc ctcaattgtc atgggatatt        420
tgctcaagac gacggtaaaa tgagcaaata tggcacgatc ctcaattgtc atgggatatt        480
tgctcaagac gacggtaaaa tgagcaaata tggcacgatc ctgaattctt cctgtcttcc        540
tattgattgc agcttccaat ttcgtcacac aacaaggtcc tagcgacggc tcacaggttt        600
tgtaacaagc aatcgaaggt tctggaatgg cgggaaaggg tttagtacca catgctatga        660
tgcccactgt gatctccaga gcaaagttcg ttcgatcgta ctgttactct ctctctttca        720
aacagaattg tccgaatcgt gtgacaacaa cagcctgttc tcacacactc ttttcttcta        780
accaaggggg tggtttagtt tagtagaacc tcgtgaaact tacatttaca tatatataaa        840
cttgcataaa ttggtcaatg caagaaatac atatttggtc ttttctaatt cgtagttttt        900
caagttctta gatgctttct ttttctcttt tttacagatc atcaaggaag taattatcta        960 cttttttacaa caaatataaa aca        983

<210> SEQ ID NO 73
<211> LENGTH: 1043
<212> TYPE: DNA
<213> ORGANISM: Artificial Sequence
<220> FEATURE:
<223> OTHER INFORMATION: Synthetic pCUR12
<220> FEATURE:
```

<223> OTHER INFORMATION: Synthetic pCUR12

<400> SEQUENCE: 73

| | |
|---|---|
| gtgagtaagg aaagagtgag gaactatcgc atacctgcat ttaaagatgc cgatttgggc | 60 |
| gcgaatcctt tattttggct tcaccctcat actattatca gggccagaaa aaggaagtgt | 120 |
| ttccctcctt cttgaattga tgttaccctc ataaagcacg tggcctctta tcgagaaaga | 180 |
| aattaccgtc gctcgtgatt tgtttgcaaa aagaacaaaa ctgaattcag gatcgtgcca | 240 |
| tatttgctca ttttaccgtc gtcttgagca aatatcccat gacaattgag gatcgtgcca | 300 |
| tatttgctca ttttaccgtc gtcttgagca aatatcccat gacaattgag gatcgtgcca | 360 |
| tatttgctca ttttaccgtc gtcttgagca aatatcccat gagaattcag gatcgtgcca | 420 |
| tatttgctca ttttaccgtc gtcttgagca aatatcccat gacaattgag gatcgtgcca | 480 |
| tatttgctca ttttaccgtc gtcttgagca aatatcccat gacaattgag gatcgtgcca | 540 |
| tatttgctca ttttaccgtc gtcttgagca aatatcccat gagaattctt cctgtcttcc | 600 |
| tattgattgc agcttccaat ttcgtcacac aacaaggtcc tagcgacggc tcacaggttt | 660 |
| tgtaacaagc aatcgaaggt tctggaatgg cgggaaaggg tttagtacca catgctatga | 720 |
| tgcccactgt gatctccaga gcaaagttcg ttcgatcgta ctgttactct ctctctttca | 780 |
| aacagaattg tccgaatcgt gtgacaacaa cagcctgttc tcacacactc ttttcttcta | 840 |
| accaggggg tggtttagtt tagtagaacc tcgtgaaact tacatttaca tatatataaa | 900 |
| cttgcataaa ttggtcaatg caagaaatac atatttggtc ttttctaatt cgtagttttt | 960 |
| caagttctta gatgctttct ttttctcttt tttacagatc atcaaggaag taattatcta | 1020 |
| cttttttacaa caaatataaa aca | 1043 |

<210> SEQ ID NO 74
<211> LENGTH: 1043
<212> TYPE: DNA
<213> ORGANISM: Artificial Sequence
<220> FEATURE:
<223> OTHER INFORMATION: Synthetic pCUR13
<220> FEATURE:
<223> OTHER INFORMATION: Synthetic pCUR13

<400> SEQUENCE: 74

| | |
|---|---|
| gtgagtaagg aaagagtgag gaactatcgc atacctgcat ttaaagatgc cgatttgggc | 60 |
| gcgaatcctt tattttggct tcaccctcat actattatca gggccagaaa aaggaagtgt | 120 |
| ttccctcctt cttgaattga tgttaccctc ataaagcacg tggcctctta tcgagaaaga | 180 |
| aattaccgtc gctcgtgatt tgtttgcaaa aagaacaaaa ctgaattctc atgggatatt | 240 |
| tgctcaagac gacggtaaaa tgagcaaata tggcacgatc ctcaattgtc atgggatatt | 300 |
| tgctcaagac gacggtaaaa tgagcaaata tggcacgatc ctcaattgtc atgggatatt | 360 |
| tgctcaagac gacggtaaaa tgagcaaata tggcacgatc ctgaattctc atgggatatt | 420 |
| tgctcaagac gacggtaaaa tgagcaaata tggcacgatc ctcaattgtc atgggatatt | 480 |
| tgctcaagac gacggtaaaa tgagcaaata tggcacgatc ctcaattgtc atgggatatt | 540 |
| tgctcaagac gacggtaaaa tgagcaaata tggcacgatc ctgaattctt cctgtcttcc | 600 |
| tattgattgc agcttccaat ttcgtcacac aacaaggtcc tagcgacggc tcacaggttt | 660 |
| tgtaacaagc aatcgaaggt tctggaatgg cgggaaaggg tttagtacca catgctatga | 720 |
| tgcccactgt gatctccaga gcaaagttcg ttcgatcgta ctgttactct ctctctttca | 780 |
| aacagaattg tccgaatcgt gtgacaacaa cagcctgttc tcacacactc ttttcttcta | 840 |

```
accaagggggg tggtttagtt tagtagaacc tcgtgaaact tacatttaca tatatataaa    900
cttgcataaa ttggtcaatg caagaaatac atatttggtc ttttctaatt cgtagttttt    960
caagttctta gatgctttct ttttctcttt tttacagatc atcaaggaag taattatcta   1020 cttttttacaa caaatataaa aca                                           1043
```

<210> SEQ ID NO 75
<211> LENGTH: 1223
<212> TYPE: DNA
<213> ORGANISM: Artificial Sequence
<220> FEATURE:
<223> OTHER INFORMATION: Synthetic pCUR14
<220> FEATURE:
<223> OTHER INFORMATION: Synthetic pCUR14

<400> SEQUENCE: 75

```
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctgaattctc atgggatatt    420
tgctcaagac gacggtaaaa tgagcaaata tggcacgatc ctcaattgtc atgggatatt    480
tgctcaagac gacggtaaaa tgagcaaata tggcacgatc ctcaattgtc atgggatatt    540
tgctcaagac gacggtaaaa tgagcaaata tggcacgatc ctgaattctc atgggatatt    600
tgctcaagac gacggtaaaa tgagcaaata tggcacgatc ctcaattgtc atgggatatt    660
tgctcaagac gacggtaaaa tgagcaaata tggcacgatc ctcaattgtc atgggatatt    720
tgctcaagac gacggtaaaa tgagcaaata tggcacgatc ctgaattctt cctgtcttcc    780
tattgattgc agcttccaat ttcgtcacac aacaaggtcc tagcgacggc tcacaggttt    840
tgtaacaagc aatcgaaggt tctggaatgg cgggaaaggg tttagtacca catgctatga    900
tgcccactgt gatctccaga gcaaagttcg ttcgatcgta ctgttactct ctctctttca    960
aacagaattg tccgaatcgt gtgacaacaa cagcctgttc tcacacactc ttttcttcta   1020 accaagggg tggtttagtt tagtagaacc tcgtgaaact tacatttaca tatatataaa   1080
cttgcataaa ttggtcaatg caagaaatac atatttggtc ttttctaatt cgtagttttt   1140
caagttctta gatgctttct ttttctcttt tttacagatc atcaaggaag taattatcta   1200 cttttttacaa caaatataaa aca                                          1223
```

<210> SEQ ID NO 76
<211> LENGTH: 1283
<212> TYPE: DNA
<213> ORGANISM: Artificial Sequence
<220> FEATURE:
<223> OTHER INFORMATION: Synthetic pCUR15
<220> FEATURE:
<223> OTHER INFORMATION: Synthetic pCUR15

<400> SEQUENCE: 76

```
gtgagtaagg aaagagtgag gaactatcgc atacctgcat ttaaagatgc cgatttgggc     60
gcgaatcctt tattttggct tcaccctcat actattatca gggccagaaa aaggaagtgt    120
```

-continued

| | |
|---|---|
| ttccctcctt cttgaattga tgttaccctc ataaagcacg tggcctctta tcgagaaaga | 180 |
| aattaccgtc gctcgtgatt tgtttgcaaa aagaacaaaa ctgaattcag gatcgtgcca | 240 |
| tatttgctca ttttaccgtc gtcttgagca aatatcccat gacaattgag gatcgtgcca | 300 |
| tatttgctca ttttaccgtc gtcttgagca aatatcccat gacaattgag gatcgtgcca | 360 |
| tatttgctca ttttaccgtc gtcttgagca aatatcccat gacaattgag gatcgtgcca | 420 |
| tatttgctca ttttaccgtc gtcttgagca aatatcccat gagaattcag gatcgtgcca | 480 |
| tatttgctca ttttaccgtc gtcttgagca aatatcccat gacaattgag gatcgtgcca | 540 |
| tatttgctca ttttaccgtc gtcttgagca aatatcccat gacaattgag gatcgtgcca | 600 |
| tatttgctca ttttaccgtc gtcttgagca aatatcccat gagaattcag gatcgtgcca | 660 |
| tatttgctca ttttaccgtc gtcttgagca aatatcccat gacaattgag gatcgtgcca | 720 |
| tatttgctca ttttaccgtc gtcttgagca aatatcccat gacaattgag gatcgtgcca | 780 |
| tatttgctca ttttaccgtc gtcttgagca aatatcccat gagaattctt cctgtcttcc | 840 |
| tattgattgc agcttccaat ttcgtcacac aacaaggtcc tagcgacggc tcacaggttt | 900 |
| tgtaacaagc aatcgaaggt tctggaatgg cgggaaaggg tttagtacca catgctatga | 960 |
| tgcccactgt gatctccaga gcaaagttcg ttcgatcgta ctgttactct ctctctttca | 1020 |
| aacagaattg tccgaatcgt gtgacaacaa cagcctgttc tcacacactc ttttcttcta | 1080 |
| accaaggggg tggtttagtt tagtagaacc tcgtgaaact tacatttaca tatatataaa | 1140 |
| cttgcataaa ttggtcaatg caagaaatac atatttggtc ttttctaatt cgtagttttt | 1200 |
| caagttctta gatgctttct ttttctcttt tttacagatc atcaaggaag taattatcta | 1260 |
| cttttttacaa caaatataaa aca | 1283 |

<210> SEQ ID NO 77
<211> LENGTH: 686
<212> TYPE: DNA
<213> ORGANISM: Artificial Sequence
<220> FEATURE:
<223> OTHER INFORMATION: Synthetic pCUR16
<220> FEATURE:
<223> OTHER INFORMATION: Synthetic pCUR16

<400> SEQUENCE: 77

| | |
|---|---|
| gctcagcatc tgcttcttcc caaagatgaa cgcggcgtta tgtcactaac gacgtgcacc | 60 |
| aacttgcggg aattctcatg ggatatttgc tcaagacgac ggtaaaatga gcaaatatgg | 120 |
| cacgatcctc aattgtcatg ggatatttgc tcaagacgac ggtaaaatga gcaaatatgg | 180 |
| cacgatcctc aatgtcatgg gatatttgct caagacgacg gtaaaatgag caaatatggc | 240 |
| acgatcctga attccaccgc acgccttttt tctgaagccc actttcgtgg actttgccat | 300 |
| atatgcaaaa ttcatgaagt gtgataccaa gtcagcatac acctcactag ggtagtttct | 360 |
| ttggttgtat tgatcatttg gttcatcgtg gttcattaat tttttttctc cattgctttc | 420 |
| tggctttgat cttactatca tttggatttt tgtcgaaggt tgtagaattg tatgtgacaa | 480 |
| gtggcaccaa gcatatataa aaaaaaaaag cattatcttc ctaccagagt tgattgttaa | 540 |
| aaacgtattt atagcaaacg caattgtaat taattcttat tttgtatctt tcttcccctt | 600 |
| gtctcaatct tttatttta ttttattttt cttttcttag tttctttcat aacaccaagc | 660 |
| aactaatact ataacataca ataata | 686 |

<210> SEQ ID NO 78
<211> LENGTH: 747

<212> TYPE: DNA
<213> ORGANISM: Artificial Sequence
<220> FEATURE:
<223> OTHER INFORMATION: Synthetic pCUR17
<220> FEATURE:
<223> OTHER INFORMATION: Synthetic pCUR17

<400> SEQUENCE: 78

```
gctcagcatc tgcttcttcc caaagatgaa cgcggcgtta tgtcactaac gacgtgcacc      60
aacttgcggg aattctcatg ggatatttgc tcaagacgac ggtaaaatga gcaaatatgg     120
cacgatcctc aattgtcatg ggatatttgc tcaagacgac ggtaaaatga gcaaatatgg     180
cacgatcctc aattctcatg ggatatttgc tcaagacgac ggtaaaatga gcaaatatgg     240
cacgatcctc aattctcatg ggatatttgc tcaagacgac ggtaaaatga gcaaatatgg     300
cacgatcctg aattccaccg cacgcctttt ttctgaagcc cactttcgtg gactttgcca     360
tatatgcaaa attcatgaag tgtgatacca agtcagcata cacctcacta gggtagtttc     420
tttggttgta ttgatcattt ggttcatcgt ggttcattaa ttttttttct ccattgcttt     480
ctggctttga tcttactatc atttggattt ttgtcgaagg ttgtagaatt gtatgtgaca     540
agtggcacca agcatatata aaaaaaaaaa gcattatctt cctaccagag ttgattgtta     600
aaaacgtatt tatagcaaac gcaattgtaa ttaattctta ttttgtatct tttcttccct     660
tgtctcaatc ttttattttt attttatttt tcttttctta gtttctttca taacaccaag     720
caactaatac tataacatac aataata                                         747
```

<210> SEQ ID NO 79
<211> LENGTH: 500
<212> TYPE: DNA
<213> ORGANISM: Saccharomyces cerevisiae
<220> FEATURE:
<223> OTHER INFORMATION: pLYS1
<220> FEATURE:
<223> OTHER INFORMATION: pLYS1

<400> SEQUENCE: 79

```
gcaagttaac attagggaga acgtggggcc ttcctccatg agtgcagagc aattgaagat      60
gtttagaggt ttaaaggaga ataaccagtt gctggatagc tctgtgccag ctacagttta     120
tgccaaattg gcccttcatg gtattcctga cggtgttaat ggacagtact tgagctataa     180
tgaccctgcc ttggcggact ttatgccttg aggatagcag gtacatataa attgttacat     240
actaagtcga tgagtcaaaa aagactctta tacatttata cattttgcat tattatttt      300
ttttttcagc ggaatttgga attccgctct caaccgccaa aattcccctg cgatttcagc     360
gacaaagagt cataaagtca tcctcgagaa accacgatga aatatataaa agcccatct     420
tccctgacgg aaactggtat tttaggaggc ataccataag ataacaacga aaacgcttta     480
tttttcacac aaccgcaaaa                                                 500
```

<210> SEQ ID NO 80
<211> LENGTH: 650
<212> TYPE: DNA
<213> ORGANISM: Saccharomyces cerevisiae
<220> FEATURE:
<223> OTHER INFORMATION: pLYS4
<220> FEATURE:
<223> OTHER INFORMATION: pLYS4

<400> SEQUENCE: 80

```
ttgaaaaatg cgaagttgaa gtgccataga agagaaacag cccacacagg ggagaagccc      60
```

```
actggaaagg gggcactgac caactttaaa taggaaacag aagataccac aagccagcga    120
tacaacagca ccaaacaccg aaaagaatag ccaaagctgt cctctggtgt tggaaaaact    180
ggaaaaaacg caactgcgtt ggctgctacg gtgaaaaatt ttcctatgac ttttttcact    240
gcttgttcgt gcgaaattac cgcaaacccg gtaaaatgta cacgtatcaa gtgataaaca    300
atttcgtgtc aagtgagcag aatggagcga tttggaaaaa aaaattttt attgttttt    360 cccccgggat tttgctcgag atgactgaaa ttttgtaatc gatgagtcta taccagaggc    420
agcaaatatc accaacatac acaggtatac acaatctcat gtccacacac acgtacagac    480
acgcacatat atatatatat atatatatcc ccataggtat ttatatatac aaaagaatcc    540
tcgtgtgttt gtgtgtgcaa tagctagttt tgcgctgcct cttatagtag acaatatcac    600
tttttcaata aaatagaact tgcaaggaaa caaaattgta tcgcttcaag                650

<210> SEQ ID NO 81
<211> LENGTH: 500
<212> TYPE: DNA
<213> ORGANISM: Saccharomyces cerevisiae
<220> FEATURE:
<223> OTHER INFORMATION: pLYS9
<220> FEATURE:
<223> OTHER INFORMATION: pLYS9

<400> SEQUENCE: 81
acatatgcaa gagtcttatg tatcgtatct aagtgccacg taggggattc ccatcatttg     60
atgatttcca aatataatac ctgtagagag cggtggagca aaagtcaaat tttaatcgca    120
actgcagaca agtcaagctg aggaaattgt ggatgatctc ttgtttcttt tgatattcac    180
cacaacagaa gtgaagagtg tgattgcggt tactactgac cacgaagcaa tgcgtttagt    240
agtgaaaaga attactcata ctctggaatc gaaattccgt tggaaaaatt cgctttgtag    300
tgaaaaataa agatgtcaat aaagggtatt gagaatttcc aatggaatta tcagcaatag    360
atgatagaaa gtagcacaga atttggctta atggtatata accgtaggg tcctggtaaa    420 attacatggg aaggatcctt aggcagtagg gaaaacttat caggacaatt gagttatatt    480
aacgtattat atatttaat                                                  500

<210> SEQ ID NO 82
<211> LENGTH: 494
<212> TYPE: DNA
<213> ORGANISM: Artificial Sequence
<220> FEATURE:
<223> OTHER INFORMATION: Synthetic pLYR1p
<220> FEATURE:
<223> OTHER INFORMATION: Synthetic LYR1p

<400> SEQUENCE: 82
ttatattgaa ttttcaaaaa ttcttacttt tttttggat ggacgcaaag aagtttaata     60
atcatattac atggcattac caccatatac atatccatat ctaatcttac ttatatgttg    120
tggaaatgta aagagcccga attcctcata ctctggaatc gaaattccgt tggaaaaatt    180
cgctttgtag tgaaaaataa agatgtcaat aaagggtatt gagaatttcc aatggaatta    240
tcagcaatag atgatagaaa gaattcggat gataatgcga ttagtttttt agccttattt    300
ctggggtaat taatcagcga agcgatgatt tttgatctat taacagatat ataaatggaa    360
aagctgcata accactttaa ctaatacttt caacattttc agtttgtatt acttcttatt    420
caaatgtcat aaaagtatca acaaaaaatt gttaatatac ctctatactt taacgtcaag    480
gagaaaaaac tata                                                       494
```

<210> SEQ ID NO 83
<211> LENGTH: 494
<212> TYPE: DNA
<213> ORGANISM: Artificial Sequence
<220> FEATURE:
<223> OTHER INFORMATION: Synthetic pLYR2p
<220> FEATURE:
<223> OTHER INFORMATION: Synthetic pLYR2p

<400> SEQUENCE: 83

```
ttatattgaa ttttcaaaaa ttcttacttt tttttggat ggacgcaaag aagtttaata      60
atcatattac atggcattac caccatatac atatccatat ctaatcttac ttatatgttg     120
tggaaatgta aagagcccga attctttcta tcatctattg ctgataattc cattggaaat    180
tctcaatacc ctttattgac atctttattt ttcactacaa agcgaatttt tccaacggaa    240
tttcgattcc agagtatgag gaattcggat gataatgcga ttagtttttt agccttattt    300
ctggggtaat taatcagcga agcgatgatt tttgatctat taacagatat ataaatggaa    360
aagctgcata accactttaa ctaatacttt caacattttc agtttgtatt acttcttatt    420
caaatgtcat aaaagtatca acaaaaaatt gttaatatac ctctatactt taacgtcaag    480
gagaaaaaac tata                                                      494
```

<210> SEQ ID NO 84
<211> LENGTH: 616
<212> TYPE: DNA
<213> ORGANISM: Artificial Sequence
<220> FEATURE:
<223> OTHER INFORMATION: Synthetic pLYR3p
<220> FEATURE:
<223> OTHER INFORMATION: Synthetic pLYR3p

<400> SEQUENCE: 84

```
ttatattgaa ttttcaaaaa ttcttacttt tttttggat ggacgcaaag aagtttaata      60
atcatattac atggcattac caccatatac atatccatat ctaatcttac ttatatgttg    120
tggaaatgta aagagcccga attcctcata ctctggaatc gaaattccgt tggaaaaatt    180
cgctttgtag tgaaaataa agatgtcaat aaagggtatt gagaatttcc aatggaatta    240
tcagcaatag atgatagaaa gaattcctca tactctggaa tcgaaattcc gttggaaaaa    300
ttcgctttgt agtgaaaaat aaagatgtca ataagggta ttgagaattt ccaatggaat    360
tatcagcaat agatgataga agaattcgg atgataatgc gattagtttt ttagccttat    420
ttctggggta attaatcagc gaagcgatga ttttgatct attaacagat ataaaatgg    480
aaaagctgca taaccacttt aactaatact ttcaacattt tcagtttgta ttacttctta    540
ttcaaatgtc ataaaagtat caacaaaaaa ttgttaatat acctctatac tttaacgtca    600
aggagaaaaa actata                                                   616
```

<210> SEQ ID NO 85
<211> LENGTH: 616
<212> TYPE: DNA
<213> ORGANISM: Artificial Sequence
<220> FEATURE:
<223> OTHER INFORMATION: Synthetic pLYR4p
<220> FEATURE:
<223> OTHER INFORMATION: Synthetic LYR4p

<400> SEQUENCE: 85

```
ttatattgaa ttttcaaaaa ttcttacttt tttttggat ggacgcaaag aagtttaata      60
```

```
atcatattac atggcattac caccatatac atatccatat ctaatcttac ttatatgttg    120
tggaaatgta aagagcccga attctttcta tcatctattg ctgataattc cattggaaat    180
tctcaatacc ctttattgac atctttattt ttcactacaa agcgaatttt tccaacggaa    240
tttcgattcc agagtatgag gaattctttc tatcatctat tgctgataat tccattggaa    300
attctcaata ccctttattg acatctttat ttttcactac aaagcgaatt tttccaacgg    360
aatttcgatt ccagagtatg aggaattcgg atgataatgc gattagtttt ttagccttat    420
ttctggggta attaatcagc gaagcgatga ttttgatct attaacagat atataaatgg    480
aaaagctgca taaccacttt aactaatact ttcaacattt tcagtttgta ttacttctta    540
ttcaaatgtc ataaaagtat caacaaaaaa ttgttaatat acctctatac tttaacgtca    600
aggagaaaaa actata    616

<210> SEQ ID NO 86
<211> LENGTH: 738
<212> TYPE: DNA
<213> ORGANISM: Artificial Sequence
<220> FEATURE:
<223> OTHER INFORMATION: Synthetic pLYR5p
<220> FEATURE:
<223> OTHER INFORMATION: Synthetic pLYR5p

<400> SEQUENCE: 86
ttatattgaa ttttcaaaaa ttcttacttt tttttttggat ggacgcaaag aagtttaata     60
atcatattac atggcattac caccatatac atatccatat ctaatcttac ttatatgttg    120
tggaaatgta aagagcccga attctttcta tcatctattg ctgataattc cattggaaat    180
tctcaatacc ctttattgac atctttattt ttcactacaa agcgaatttt tccaacggaa    240
tttcgattcc agagtatgag gaattctttc tatcatctat tgctgataat tccattggaa    300
attctcaata ccctttattg acatctttat ttttcactac aaagcgaatt tttccaacgg    360
aatttcgatt ccagagtatg aggaattctt tctatcatct attgctgata attccattgg    420
aaattctcaa tacccttttat tgacatcttt attttttcact acaaagcgaa ttttttccaac    480 ggaatttcga ttccagagta tgaggaattc ggatgataat gcgattagtt ttttagcctt    540
atttctgggg taattaatca gcgaagcgat gattttttgat ctattaacag atatataaat    600
ggaaaagctg cataaccact ttaactaata ctttcaacat tttcagtttg tattacttct    660
tattcaaatg tcataaaagt atcaacaaaa aattgttaat atacctctat actttaacgt    720
caaggagaaa aaactata    738

<210> SEQ ID NO 87
<211> LENGTH: 1104
<212> TYPE: DNA
<213> ORGANISM: Artificial Sequence
<220> FEATURE:
<223> OTHER INFORMATION: Synthetic pLYR6p
<220> FEATURE:
<223> OTHER INFORMATION: Synthetic pLYR6p

<400> SEQUENCE: 87
ttatattgaa ttttcaaaaa ttcttacttt tttttttggat ggacgcaaag aagtttaata     60
atcatattac atggcattac caccatatac atatccatat ctaatcttac ttatatgttg    120
tggaaatgta aagagcccga attgctcata ctctggaatc gaaattccgt tggaaaaatt    180
cgctttgtag tgaaaaataa agatgtcaat aaagggtatt gagaatttcc aatggaatta    240
tcagcaatag atgatagaaa gaattcctca tactctggaa tcgaaattcc gttggaaaaa    300
```

```
ttcgctttgt agtgaaaaat aaagatgtca ataaagggta ttgagaattt ccaatggaat      360
tatcagcaat agatgataga aagaattcct catactctgg aatcgaaatt ccgttggaaa      420
aattcgcttt gtagtgaaaa ataaagatgt caataaaggg tattgagaat tccaatgga      480 attatcagca atagatgata gaaacaattg ctcatactct ggaatcgaaa ttccgttgga      540
aaaattcgct ttgtagtgaa aataaagat gtcaataaag ggtattgaga atttccaatg       600
gaattatcag caatagatga tagaaagaat tcctcatact ctggaatcga aattccgttg      660
gaaaaattcg ctttgtagtg aaaataaag atgtcaataa agggtattga gaatttccaa      720
tggaattatc agcaatagat gatagaaaga attcctcata ctctggaatc gaaattccgt      780
tggaaaaatt cgctttgtag tgaaaaataa agatgtcaat aaagggtatt gagaatttcc      840
aatggaatta tcagcaatag atgatagaaa caattcggat gataatgcga ttagtttttt      900 agccttatt ctggggtaat taatcagcga agcgatgatt tttgatctat aacagatat       960 ataaatggaa aagctgcata accactttaa ctaatacttt caacatttc agtttgtatt      1020 acttcttatt caaatgtcat aaaagtatca acaaaaaatt gttaatatac ctctatactt     1080
taacgtcaag gagaaaaaac tata                                            1104
```

<210> SEQ ID NO 88
<211> LENGTH: 1836
<212> TYPE: DNA
<213> ORGANISM: Artificial Sequence
<220> FEATURE:
<223> OTHER INFORMATION: Synthetic pLYR7p
<220> FEATURE:
<223> OTHER INFORMATION: Synthetic pLYR7p

<400> SEQUENCE: 88

```
ttatattgaa ttttcaaaaa ttcttacttt tttttggat ggacgcaaag aagtttaata      60
atcatattac atggcattac caccatatac atatccatat ctaatcttac ttatatgttg     120
tggaaatgta aagagcccga attgtttcta tcatctattg ctgataattc cattggaaat     180
tctcaatacc ctttattgac atctttattt ttcactacaa agcgaatttt tccaacggaa     240
tttcgattcc agagtatgag gaattctttc tatcatctat tgctgataat tccattggaa     300
attctcaata ccctttattg acatcttat ttttcactac aaagcgaatt ttccaacgg       360 aatttcgatt ccagagtatg aggaattctt tctatcatct attgctgata attccattgg     420
aaattctcaa tacccttat tgacatcttt attttcact acaaagcgaa ttttccaac        480 ggaattcga ttccagagta tgagcaattg tttctatcat ctattgctga taattccatt      540
ggaaattctc aatacccttt attgacatct ttattttca ctacaaagcg aattttccca      600 acggaattc gattccagag tatgaggaat tctttctatc atctattgct gataattcca      660
ttggaaattc tcaatacct ttattgacat ctttatttt cactacaaag cgaattttc        720 caacggaatt cgattccag agtatgagga attcttctct atcatctattg ctgataattc     780 cattggaaat tctcaatacc ctttattgac atctttattt ttcactacaa agcgaatttt     840
tccaacggaa tttcgattcc agagtatgag caattgtttc tatcatctat tgctgataat     900
tccattggaa attctcaata cccttattg acatcttat ttttcactac aaagcgaatt      960
tttccaacgg aatttcgatt ccagagtatg aggaattctt tctatcatct attgctgata    1020
attccattgg aaattctcaa tacccttat tgacatcttt attttcact acaaagcgaa     1080 ttttccaac ggaatttcga ttccagagta tgaggaattc tttctatcat ctattgctga    1140
```

```
taattccatt ggaaattctc aatacccttt attgacatct ttattttca ctacaaagcg      1200 aattttccca acggaatttc gattccagag tatgagcaat tgtttctatc atctattgct      1260
gataattcca ttggaaattc tcaatacct ttattgacat ctttatttt cactacaaag       1320 cgaatttttc aacggaatt tcgattccag agtatgagga attctttcta tcatctattg      1380
ctgataattc cattggaaat tctcaatacc ctttattgac atctttattt ttcactacaa      1440
agcgaatttt ccaacggaa tttcgattcc agagtatgag gaattcttcc tatcatctat      1500
tgctgataat tccattggaa attctcaata cctttattg acatctttat ttttcactac      1560
aaagcgaatt tttccaacgg aatttcgatt ccagagtatg agcaattcgg atgataatgc      1620
gattagtttt ttagccttat ttctggggta attaatcagc gaagcgatga ttttgatct      1680 attaacagat atataaatgg aaaagctgca taaccacttt aactaatact ttcaacattt      1740
tcagtttgta ttacttctta ttcaaatgtc ataaaagtat caacaaaaaa ttgttaatat      1800
acctctatac tttaacgtca aggagaaaaa actata                                1836

<210> SEQ ID NO 89
<211> LENGTH: 981
<212> TYPE: DNA
<213> ORGANISM: Artificial Sequence
<220> FEATURE:
<223> OTHER INFORMATION: Synthetic pLYR8
<220> FEATURE:
<223> OTHER INFORMATION: Synthetic pLYR8

<400> SEQUENCE: 89
ttacattatc aatccttgcg tttcagcttc cactaattta gatgactatt tctcatcatt       60
tgcgtcatct tctaacaccg tatatgataa tatactagta acgtaaatac tagttagtag      120
atgatagttg atttttattc caacactaag aaataaattc gccatttctt gaatgtattt      180
aaagatattt aatgctataa tagacattta aatccaattc ttccaacata caatgggagt      240
ttggccgagt ggtttaaggc gtcagattta ggtggattta acctctaaaa tctctgatat      300
cttcggatgc aagggttcga atcccttagc tctcattatt ttttgctttt tctcttgaat      360
tgctcatact ctggaatcga aattccgttg gaaaaattcg ctttgtagtg aaaaataaag      420
atgtcaataa agggtattga gaatttccaa tggaattatc agcaatagat gatagaaaga      480
attcctcata ctctggaatc gaaattccgt tggaaaaatt cgctttgtag tgaaaaataa      540
agatgtcaat aaagggtatt gagaatttcc aatggaatta tcagcaatag atgatagaaa      600
gaattcctca tactctggaa tcgaaattcc gttggaaaaa ttcgctttgt agtgaaaaat      660
aaagatgtca taaagggta ttgagaattt ccaatggaat tatcagcaat agatgataga      720
aacaattcta attaagttag tcaaggcgcc atcctcatga aaactgtgta acataataac      780
cgaagtgtcg aaaaggtggc accttgtcca attgaacacg ctcgatgaaa aaaataagat      840
atatataagg ttaagtaaag cgtctgttag aaaggaagtt tttcctttt cttgctctct      900 tgtcttttca tctactattt ccttcgtgta atacagggtc gtcagataca tagatacaat      960
tctattaccc ccatccatac a                                                981

<210> SEQ ID NO 90
<211> LENGTH: 981
<212> TYPE: DNA
<213> ORGANISM: Artificial Sequence
<220> FEATURE:
<223> OTHER INFORMATION: Synthetic pLYR9
<220> FEATURE:
<223> OTHER INFORMATION: Synthetic pLYR9
```

<400> SEQUENCE: 90

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt    180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tgtttctatc atctattgct gataattcca ttggaaattc tcaataccct ttattgacat   420
ctttatttt cactacaaag cgaattttc caacggaatt tcgattccag agtatgagga    480
attcttcta tcatctattg ctgataattc cattggaaat tctcaatacc ctttattgac   540
atctttattt ttcactacaa agcgaatttt tccaacgaa tttcgattcc agagtatgag   600
gaattctttc tatcatctat tgctgataat tccattggaa attctcaata cccttattg    660
acatctttat ttttcactac aaagcgaatt tttccaacgg aatttcgatt ccagagtatg   720
agcaattcta attaagttag tcaaggcgcc atcctcatga aaactgtgta acataataac   780
cgaagtgtcg aaaaggtggc accttgtcca attgaacacg ctcgatgaaa aaataagat    840
atatataagg ttaagtaaag cgtctgttag aaaggaagtt tttcctttt cttgctctct    900
tgtcttttca tctactattt ccttcgtgta atacagggtc gtcagataca tagatacaat   960
tctattaccc ccatccatac a                                            981
```

<210> SEQ ID NO 91
<211> LENGTH: 1225
<212> TYPE: DNA
<213> ORGANISM: Artificial Sequence
<220> FEATURE:
<223> OTHER INFORMATION: Synthetic pLYR10
<220> FEATURE:
<223> OTHER INFORMATION: Synthetic pLYR10

<400> SEQUENCE: 91

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataaattc gccatttctt gaatgtattt    180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tgtttctatc atctattgct gataattcca ttggaaattc tcaataccct ttattgacat   420
ctttatttt cactacaaag cgaattttc caacggaatt tcgattccag agtatgagga    480
attcttcta tcatctattg ctgataattc cattggaaat tctcaatacc ctttattgac   540
atctttattt ttcactacaa agcgaatttt tccaacgaa tttcgattcc agagtatgag   600
gaattctttc tatcatctat tgctgataat tccattggaa attctcaata cccttattg    660
acatctttat ttttcactac aaagcgaatt tttccaacgg aatttcgatt ccagagtatg   720
aggaattctt tctatcatct attgctgata attccattgg aaattctcaa tacccttat    780
tgacatcttt atttttcact acaaagcgaa ttttccaac ggaatttcga ttccagagta   840
tgaggaattc tttctatcat ctattgctga taattccatt ggaaattctc aatacccttt   900
```

```
attgacatct ttattttca ctacaaagcg aatttttcca acggaatttc gattccagag      960
tatgagcaat tctaattaag ttagtcaagg cgccatcctc atgaaaactg tgtaacataa     1020
taaccgaagt gtcgaaaagg tggcaccttg tccaattgaa cacgctcgat gaaaaaaata    1080
agatatatat aaggttaagt aaagcgtctg ttagaaagga agttttcct ttttcttgct     1140 ctcttgtctt ttcatctact atttccttcg tgtaatacag ggtcgtcaga tacatagata    1200
caattctatt accccatcc ataca                                          1225
```

<210> SEQ ID NO 92
<211> LENGTH: 1347
<212> TYPE: DNA
<213> ORGANISM: Artificial Sequence
<220> FEATURE:
<223> OTHER INFORMATION: Synthetic pLYR11
<220> FEATURE:
<223> OTHER INFORMATION: Synthetic pLYR11

<400> SEQUENCE: 92

```
ttacattatc aatccttgcg tttcagcttc cactaattta gatgactatt tctcatcatt       60
tgcgtcatct tctaacaccg tatatgataa tatactagta acgtaaatac tagttagtag     120
atgatagttg atttttattc caacactaag aaataaattt gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tgctcatact ctggaatcga aattccgttg gaaaaattcg ctttgtagtg aaaaataaag    420
atgtcaataa agggtattga gaatttccaa tggaattatc agcaatagat gatagaaaga    480
attcctcata ctctggaatc gaaattccgt tggaaaaatt cgctttgtag tgaaaaataa    540
agatgtcaat aaagggtatt gagaatttcc aatggaatta tcagcaatag atgatagaaa    600
gaattcctca tactctggaa tcgaaattcc gttggaaaaa ttcgctttgt agtgaaaaat    660
aaagatgtca ataaagggta ttgagaattt ccaatggaat tatcagcaat agatgataga    720 agaattcct catactctgg aatcgaaatt ccgttggaaa aattcgcttt gtagtgaaaa     780
ataaagatgt caataaaggg tattgagaat ttccaatgga attatcagca atagatgata    840
gaaagaattc ctcatactct ggaatcgaaa ttccgttgga aaaattcgct ttgtagtgaa    900
aaataaagat gtcaataaag ggtattgaga atttccaatg gaattatcag caatagatga    960
tagaaagaat tcctcatact ctggaatcga aattccgttg gaaaaattcg ctttgtagtg   1020
aaaaataaag atgtcaataa agggtattga gaatttccaa tggaattatc agcaatagat   1080
gatagaaaca attctaatta agttagtcaa ggcgccatcc tcatgaaaac tgtgtaacat    1140
aataaccgaa gtgtcgaaaa ggtggcacct tgtccaattg aacacgctcg atgaaaaaaa   1200
taagatatat ataaggttaa gtaaagcgtc tgttagaaag gaagttttc cttttcttg     1260 ctctcttgtc ttttcatcta ctatttcctt cgtgtaatac agggtcgtca gatacataga    1320
tacaattcta ttaccccat ccataca                                         1347
```

<210> SEQ ID NO 93
<211> LENGTH: 686
<212> TYPE: DNA
<213> ORGANISM: Saccharomyces cerevisiae
<220> FEATURE:
<223> OTHER INFORMATION: pMET17
<220> FEATURE:
<223> OTHER INFORMATION: pMET17

<400> SEQUENCE: 93

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg atttttattc caacactaag aaataaattc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgagg   360
tcacatgatc gcaaaatggc aaatggcacg tgaagctgtc gatattgggg aactgtggtg   420
gttggcaaat gactaattaa gttagtcaag gcgccatcct catgaaaact gtgtaacata   480
ataaccgaag tgtcgaaaag gtggcacctt gtccaattga acacgctcga tgaaaaaaat   540
aagatatata taaggttaag taaagcgtct gttagaaagg aagttttttcc tttttcttgc   600
tctcttgtct tttcatctac tatttccttc gtgtaataca gggtcgtcag atacatagat   660
acaattctat taccccccatc cataca                                       686
```

<210> SEQ ID NO 94
<211> LENGTH: 510
<212> TYPE: DNA
<213> ORGANISM: Saccharomyces cerevisiae
<220> FEATURE:
<223> OTHER INFORMATION: pMET6
<220> FEATURE:
<223> OTHER INFORMATION: pMET6

<400> SEQUENCE: 94

```
ccacaggaaa tatttcacgt gacttacaaa cagagtcgta cgtcaggacc ggagtcaggt    60
gaaaaaatgt gggccggtaa agggaaaaaa ccagaaacgg gactactatc gaactcgttt   120
agtcgcgaac gtgcaaaagg ccaatatttt tcgctagagt catcgcagtc atggcagctc   180
tttcgctcta tctcccggtc gcaaaactgt ggtagtcata gctcgttctg ctcaattgag   240
aactgtgaat gtgaatatgg aacaaatgcg atagatgcac taatttaagg gaagctagct   300
agttttccca actgcgaaag aaaaaaagga aagaaaaaaa aattctatat aagtgataga   360
tatttccatc tttactagca ttagtttctc ttttacgtat tcaatatttt tgttaaactc   420
ttcctttatc ataaaaaagc aagcatctaa gagcattgac aacactctaa gaaacaaaat   480
accaatataa tttcaaagta catatcaaaa                                    510
```

<210> SEQ ID NO 95
<211> LENGTH: 508
<212> TYPE: DNA
<213> ORGANISM: Saccharomyces cerevisiae
<220> FEATURE:
<223> OTHER INFORMATION: pMET14
<220> FEATURE:
<223> OTHER INFORMATION: pMET14

<400> SEQUENCE: 95

```
cctatgcatg tttagagcaa gcgcctttgt gagccctccc ggttacgacg ccttggcaat    60
gtagcagata actctgcact tctagaatca ttccactacg acatttggct catcaccagc   120
tcgcgagaaa tgtaaataag ccaacaacca agaatgcgta acattaaaga atacagttgc   180
tttcatttcg gcgtgatggt acggcaccca cggttcctta cattattctc gaaaatagc    240
tgcacgcttt tccaggaata aaagaccgtg ccactaattt cacgtgatca atatatttac   300
```

| | |
|---|---|
| aagccacctc aaaaaatgtg gcaatggaga agaggatgaa cgactcaata tgacttcaac | 360 |
| ttcatgaatt tgtcaaaata tctatataag atgcaaaatt tctatacaac atcagttgcg | 420 |
| tatccgttaa tgtcgttcat tttctctctt tgttcgaact tgacatcaag aaaagttgga | 480 |
| attatttctc caagcacact gtacacca | 508 |

<210> SEQ ID NO 96
<211> LENGTH: 552
<212> TYPE: DNA
<213> ORGANISM: Saccharomyces cerevisiae
<220> FEATURE:
<223> OTHER INFORMATION: pMET3
<220> FEATURE:
<223> OTHER INFORMATION: pMET3

<400> SEQUENCE: 96

| | |
|---|---|
| aacgatatgt acgtagtggt ataaggtgag ggggtccaca gatataacat cgtttaattt | 60 |
| agtactaaca gagacttttg tcacaactac atataagtgt acaaatatag tacagatatg | 120 |
| acacacttgt agcgccaacg cgcatcctac ggattgctga cagaaaaaaa ggtcacgtga | 180 |
| ccagaaaagt cacgtgtaat tttgtaactc accgcattct agcggtccct gtcgtgcaca | 240 |
| ctgcactcaa caccataaac cttagcaacc tccaaaggaa atcaccgtat aacaaagcca | 300 |
| cagttttaca acttagtctc ttatgaagtt acttaccaat gagaaataga ggctctttct | 360 |
| cgacaaatat gaatatggat atatatatat atatatatat atatatatat atatatatgt | 420 |
| aaacttggtt cttttttagc ttgtgatctc tagcttgggt ctctctctgt cgtaacagtt | 480 |
| gtgatatcgt ttcttaacaa ttgaaaagga actaagaaag tataataata acaagaataa | 540 |
| agtataatta ac | 552 |

<210> SEQ ID NO 97
<211> LENGTH: 363
<212> TYPE: DNA
<213> ORGANISM: Saccharomyces cerevisiae
<220> FEATURE:
<223> OTHER INFORMATION: pSAM1
<220> FEATURE:
<223> OTHER INFORMATION: pSAM1

<400> SEQUENCE: 97

| | |
|---|---|
| gaaacggacg taagacggaa atagaatttg aagataaagt tatatatcac tacacacgaa | 60 |
| tactttcttt ttttttttc acaggaaaac tgtggtggcg cccttgccta ctagtgcatt | 120 |
| tcttttttcg ggttcttgtc tcgacgaaat tttagcctca tcgtagtttt tcactctggt | 180 |
| atcgatgaaa aagggaagag taaaaagttt tccgtttagt acttaatggg attggtttgg | 240 |
| gacgtatata tcgactggtg ttgtctgtta ttcatcgttg tttttcggtt agcttcgaaa | 300 |
| aaaaaataga gtaaaaacca ggaatttacc ctaaaaacaa gaaaaaataa gataaacgaa | 360 |
| aat | 363 |

<210> SEQ ID NO 98
<211> LENGTH: 500
<212> TYPE: DNA
<213> ORGANISM: Saccharomyces cerevisiae
<220> FEATURE:
<223> OTHER INFORMATION: pSAM2
<220> FEATURE:
<223> OTHER INFORMATION: pSAM2

<400> SEQUENCE: 98

| | |
|---|---|
| gagctttgct ctattatata agataaaata tgcactaaaa gtttgcattt ctttacataa | 60 |

```
ctaaaactaa gacattatgc atagcttacc tgatcaaaaa gtatgtaaac ttgttaacat    120
cttcacatgt gattcatctg gtcgtacttt cttgcggtgc agtgtaatat ttctacccac    180
gtgactataa ttgagcttga aaactgtggc gttttccac cgatgggtcc acgccagata    240
ttaaccgaag ccaaaatacc gatgaaattt ctgagatagc tcttgtaaac gacgtcaaat    300
cttcatatgc aaggagatct tgatttcttt ttggtagtca tctgtcgtct tgaggcgtat    360
aagaaggagg ttatatctgt cctttctaca aagtattttc gagaatcttg cttctgcccc    420
ttttttcttt tttttaaaagg tttaaaaaac ataactgtct tcaatatatc cagtatttac    480
gacaatatac aaacataatc                                                500

<210> SEQ ID NO 99
<211> LENGTH: 300
<212> TYPE: DNA
<213> ORGANISM: Saccharomyces cerevisiae
<220> FEATURE:
<223> OTHER INFORMATION: tTDH2
<220> FEATURE:
<223> OTHER INFORMATION: tTHD2

<400> SEQUENCE: 99
atttaactcc ttaagttact ttaatgattt agttttttatt attaataatt catgctcatg     60
acatctcata tacacgttta taaaacttaa atagattgaa aatgtattaa agattcctca    120
gggattcgat ttttttggaa gttttttgttt tttttttcctt gagatgctgt agtatttggg    180
aacaattata caatcgaaag atatatgctt acattcgacc gttttagccg tgatcattat    240
cctatagtaa cataacctga agcataactg acactactat catcaatact tgtcacatga    300

<210> SEQ ID NO 100
<211> LENGTH: 300
<212> TYPE: DNA
<213> ORGANISM: Saccharomyces cerevisiae
<220> FEATURE:
<223> OTHER INFORMATION: tCYC1
<220> FEATURE:
<223> OTHER INFORMATION: tCYC1

<400> SEQUENCE: 100
acaggcccct tttcctttgt cgatatcatg taattagtta tgtcacgctt acattcacgc     60
cctcctccca catccgctct aaccgaaaag gaaggagtta gacaacctga agtctaggtc    120
cctatttatt tttttttaata gttatgttag tattaagaac gttatttata tttcaaattt    180 ttctttttttt tctgtacaaa cgcgtgtacg catgtaacat tatactgaaa accttgcttg    240
agaaggtttt gggacgctcg aaggctttaa tttgcaagct tcgcagttta cactctcatc    300

<210> SEQ ID NO 101
<211> LENGTH: 300
<212> TYPE: DNA
<213> ORGANISM: Saccharomyces cerevisiae
<220> FEATURE:
<223> OTHER INFORMATION: tTDH3
<220> FEATURE:
<223> OTHER INFORMATION: tTDH3

<400> SEQUENCE: 101
gtgaatttac tttaaatctt gcatttaaat aaattttctt tttatagctt tatgacttag     60
tttcaattta tatactattt taatgacatt ttcgattcat tgattgaaag ctttgtgttt    120
tttcttgatg cgctattgca ttgttcttgt ctttttcgcc acatgtaaata tctgtagtag    180
```
atacctgata cattgtggat gctgagtgaa attttagtta ataatggagg cgctcttaat    240
aattttgggg atattggctt ttttttttaa agtttacaaa tgaatttttt ccgccaggat    300

<210> SEQ ID NO 102
<211> LENGTH: 354
<212> TYPE: DNA
<213> ORGANISM: Saccharomyces cerevisiae
<220> FEATURE:
<223> OTHER INFORMATION: tADH1
<220> FEATURE:
<223> OTHER INFORMATION: tADH1

<400> SEQUENCE: 102
actagttcta gagcggccgc caccgcggtg gcgaatttc ttatgattta tgattttat     60 tattaaataa gttataaaaa aaataagtgt atacaaattt taaagtgact cttaggtttt    120
aaaacgaaaa ttcttattct tgagtaactc tttcctgtag gtcaggttgc tttctcaggt    180
atagcatgag gtcgctctta ttgaccacac ctctaccggc atgccagca aatgcctgca     240 aatcgctccc catttcaccc aattgtagat atgctaactc cagcaatgag ttgatgaatc    300
tcggtgtgta ttttatgtcc tcagaggaca cacctgttg taatcgttct tcca           354

<210> SEQ ID NO 103
<211> LENGTH: 301
<212> TYPE: DNA
<213> ORGANISM: Saccharomyces cerevisiae
<220> FEATURE:
<223> OTHER INFORMATION: tADH2
<220> FEATURE:
<223> OTHER INFORMATION: tADH2

<400> SEQUENCE: 103
gcggatctct tatgtcttta cgatttatag ttttcattat caagtatgcc tatattagta     60
tatagcatct ttagatgaca gtgttcgaag tttcacgaat aaagataat attctacttt    120 ttgctcccac cgcgtttgct agcacgagtg aacaccatcc ctcgcctgtg agttgtaccc    180
attcctctaa actgtagaca tggtagcttc agcagtgttc gttatgtacg gcatcctcca    240
acaaacagtc ggttatagtt tgtcctgctc ctctgaatcg tctccctcga tatttctcat    300
t                                                                    301

<210> SEQ ID NO 104
<211> LENGTH: 299
<212> TYPE: DNA
<213> ORGANISM: Saccharomyces cerevisiae
<220> FEATURE:
<223> OTHER INFORMATION: tTPI1
<220> FEATURE:
<223> OTHER INFORMATION: tTPI1

<400> SEQUENCE: 104
gattaatata attatataaa aatattatct tcttttcttt atatctagtg ttatgtaaaa     60
taaattgatg actacggaaa gcttttttat attgttctt tttcattctg agccacttaa    120
atttcgtgaa tgttcttgta agggacggta gatttacaag tgatacaaca aaaagcaagg    180 cgcttttttct aataaaaaga agaaaagcat ttaacaattg aacacctcta tatcaacgaa    240
gaatattact ttgtctctaa atccttgtaa aatgtgtacg atctctatat gggttactc    299

<210> SEQ ID NO 105
<211> LENGTH: 299
<212> TYPE: DNA
<213> ORGANISM: Saccharomyces cerevisiae

```
<220> FEATURE:
<223> OTHER INFORMATION: tMET17
<220> FEATURE:
<223> OTHER INFORMATION: tMET17

<400> SEQUENCE: 105
gtgtgcgtaa tgagttgtaa aattatgtat aaacctactt tctctcacaa gtactatact      60
tttataaaac gaactttatt gaaatgaata tccttttttt cccttgttac atgtcgtgac     120
tcgtactttg aacctaaatt gttctaacat caaagaacag tgttaattcg cagtcgagaa     180
gaaaaatatg gtgaacaaga ctcatctact tcatgagact actttacgcc tcctataaag     240
ctgtcacact ggataaattt attgtaggac caagttacaa agaggatga tggaggttt      299

<210> SEQ ID NO 106
<211> LENGTH: 305
<212> TYPE: DNA
<213> ORGANISM: Saccharomyces cerevisiae
<220> FEATURE:
<223> OTHER INFORMATION: tENO2
<220> FEATURE:
<223> OTHER INFORMATION: tENO2

<400> SEQUENCE: 106
ggatcctaaa gtgcttttaa ctaagaatta ttagtctttt ctgcttattt tttcatcata      60
gtttagaaca cttatatta acgaatagtt tatgaatcta tttaggttta aaaattgata     120
cagttttata agttactttt tcaaagactc gtgctgtcta ttgcataatg cactggaagg     180
ggaaaaaaaa ggtgcacacg cgtggctttt tcttgaattt gcagtttgaa aaataactac     240
atggatgata agaaaacatg gagtacagtc actttgagaa ccttcaatca gctggtaacg     300
tcttc                                                                305

<210> SEQ ID NO 107
<211> LENGTH: 300
<212> TYPE: DNA
<213> ORGANISM: Saccharomyces cerevisiae
<220> FEATURE:
<223> OTHER INFORMATION: tMET3
<220> FEATURE:
<223> OTHER INFORMATION: tMET3

<400> SEQUENCE: 107
tcgtcataaa atgctcccat ctcaaaagta gggcaaaatt catgatcgac cgcgcaaaat      60
aaatagattt gcaaataagt tttgtatgta catttattaa tatatataat atatcaaaag     120
aaaaaaatca aaaaaaaaaa aaaaaaaaaa ttgcactctt attcagtcat caattacaaa     180
acctagagat agcgatggtg catattcaat aaaaaactcc ttatactgtc gagaaagctt     240
attattggta cttctcgaag atactaaaaa aggttaattt ttggagacgg aggcaatagc     300

<210> SEQ ID NO 108
<211> LENGTH: 301
<212> TYPE: DNA
<213> ORGANISM: Saccharomyces cerevisiae
<220> FEATURE:
<223> OTHER INFORMATION: tPGK1
<220> FEATURE:
<223> OTHER INFORMATION: tPGK1

<400> SEQUENCE: 108
attgaattga attgaaatcg atagatcaat ttttttcttt tctctttccc catcctttac      60
gctaaaataa tagtttattt tattttttga atattttta tttatatacg tatatataga     120
```

```
ctattattta tcttttaatg attattaaga ttttattaa aaaaaaattc gctcctcttt      180
taatgccttt atgcagtttt ttttccccat tcgatatttc tatgttcggg ttcagcgtat      240
tttaagttta ataactcgaa aattctgcgt tcgttaaagc tttcgagaag gatattattt      300
a                                                                      301

<210> SEQ ID NO 109
<211> LENGTH: 300
<212> TYPE: DNA
<213> ORGANISM: Saccharomyces cerevisiae
<220> FEATURE:
<223> OTHER INFORMATION: tDIT1
<220> FEATURE:
<223> OTHER INFORMATION: tDIT1

<400> SEQUENCE: 109
taaagtaaga gcgctacatt ggtctaccct tttgttcttt tacttaaaca ttagttagtt       60
cgttttcttt ttctcatttt tttatgtttc cccccccaaag ttctgatttt ataatatttt     120
atttcacaca attccattta acagaggggg aatagattct ttagcttaga aaattagtga     180
tcaatatata tttgcctttc ttttcatctt ttcagtgata ttaatggttt cgagacactg     240
caatggccct agttgtctaa gaggatagat gttactgtca aagtgatat tttgaattc      300

<210> SEQ ID NO 110
<211> LENGTH: 300
<212> TYPE: DNA
<213> ORGANISM: Saccharomyces cerevisiae
<220> FEATURE:
<223> OTHER INFORMATION: tRPL3
<220> FEATURE:
<223> OTHER INFORMATION: tRPL3

<400> SEQUENCE: 110
gaagttttgt tagaaaataa atcatttttt aattgagcat tcttattcct atttttattta      60 aatagtttta tgtattgtta gctacataca acagtttaaa tcaaattttc ttttttcccaa    120 gtccaaaatg gaggtttatt ttgatgaccc gcatgcgatt atgttttgaa agtataagac     180
tacatacatg tacatatatt taaacatgta aacccgtcca ttatattgct tacttcttc     240 ttttttgccg ttttgacttg gacctctggt ttgctatttc cttacaatct tgctacaat    300

<210> SEQ ID NO 111
<211> LENGTH: 300
<212> TYPE: DNA
<213> ORGANISM: Saccharomyces cerevisiae
<220> FEATURE:
<223> OTHER INFORMATION: tRPL41B
<220> FEATURE:
<223> OTHER INFORMATION: tRPL41B

<400> SEQUENCE: 111
gcggattgag agcaaatcgt taagttcagg tcaagtaaaa attgatttcg aaaactaatt      60
tctcttatac aatcctttga ttggaccgtc atcctttcga atataagatt ttgttaagaa    120
tattttagac agagatctac tttatattta atatctagat attacataat ttcctctcta    180 ataaatatc attaataaaa taaaaatgaa gcgatttgat tttgtgttgt caacttagtt     240
tgccgctatg cctcttgggt aatgctatta ttgaatcgaa gggctttatt atattaccct    300

<210> SEQ ID NO 112
<211> LENGTH: 300
<212> TYPE: DNA
<213> ORGANISM: Saccharomyces cerevisiae
```

```
<220> FEATURE:
<223> OTHER INFORMATION: tRPL15A
<220> FEATURE:
<223> OTHER INFORMATION: tRPL15A

<400> SEQUENCE: 112
gctggttgat ggaaaatata attttattgg gcaaactttt gttatctga tgtgttttat       60 actattatct ttttaattaa tgattctata tacaaacctg tatattttt ctttaaccaa      120 tttttttttt tatagaccta gagctgtact tttattctgc tatcaagcaa accctaccc      180 cctcttctca atcctcccct caggcagaac ttatctacct gtatcaagga gcggacgagg    240
gagtcctaat tgttctacgt ataccaatgc tagcagctta cataggtggt ggcactacca    300

<210> SEQ ID NO 113
<211> LENGTH: 300
<212> TYPE: DNA
<213> ORGANISM: Saccharomyces cerevisiae
<220> FEATURE:
<223> OTHER INFORMATION: tIDP1
<220> FEATURE:
<223> OTHER INFORMATION: tIDP1

<400> SEQUENCE: 113
tcgaatttac gtagcccaat ctaccacttt ttttttttcat tttttaaagt gttatactta    60
gttatgctct aggataatga actacttttt ttttttttt tttactgtta tcataaatat    120 atataccttta ttgttgttttg caaccgtcgg ttaattcctt atcaaggttc cccaagttcg   180
gatcattacc atcaatttcc aacattttca tgagttcttc ttcttcatta ccgtgtttta   240
gggggctgtt cgcacttcta atagggctat caccaagctg ttctaattcg tccaaaagtt   300

<210> SEQ ID NO 114
<211> LENGTH: 1089
<212> TYPE: DNA
<213> ORGANISM: Kluveromyces lactis
<220> FEATURE:
<223> OTHER INFORMATION: Leu2
<220> FEATURE:
<223> OTHER INFORMATION: Leu2

<400> SEQUENCE: 114
atgtctaaga atatcgttgt cctaccgggt gatcacgtcg gtaaagaagt tactgacgaa      60
gctattaagg tcttgaatgc cattgctgaa gtccgtccag aaattaagtt caatttccaa    120
catcacttga tcgggggtgc tgccatcgat gccactggca ctcctttacc agatgaagct    180
ctagaagcct ctaagaaagc cgatgctgtc ttactaggtg ctgttggtgg tccaaaatgg    240
ggtacgggcg cagttagacc agaacaaggt ctattgaaga tcagaaagga attgggtcta    300
tacgccaact tgagaccatg taactttgct tctgattctt tactagatct ttctcctttg    360
aagcctgaat atgcaaaggg taccgatttc gtcgtcgtta gagaattggt tggtggtatc    420
tactttggtg aaagaaaaga agatgaaggt gacgagttg cttgggactc tgagaaatac    480
agtgttcctg aagttcaaag aattacaaga atggctgctt tcttggcatt gcaacaaaac    540
ccaccattac caatctggtc tcttgacaag gctaacgtgc ttgcctcttc cagattgtgg    600
agaaagactg ttgaagaaac catcaagact gagttcccac aattaactgt tcagcaccaa    660
ttgatcgact ctgctgctat gattttggtt aaatcaccaa ctaagctaaa cggtgttgtt    720
attaccaaca acatgtttgg tgatattatc tccgatgaag cctctgttat tccaggttct    780
ttgggtttat taccttctgc atctctagct tccctacctg acactaacaa ggcattcggt    840
```

-continued

```
ttgtacgaac catgtcatgg ttctgcccca gatttaccag caaacaaggt taacccaatt        900
gctaccatct tatctgcagc tatgatgttg aagttatcct tggatttggt tgaagaaggt        960
agggctcttg aagaagctgt tagaaatgtc ttggatgcag gtgtcagaac cggtgacctt       1020
ggtggttcta actctaccac tgaggttggc gatgctatcg ccaaggctgt caaggaaatc       1080
ttggcttaa                                                              1089
```

<210> SEQ ID NO 115
<211> LENGTH: 362
<212> TYPE: PRT
<213> ORGANISM: Kluveromyces lactis
<220> FEATURE:
<223> OTHER INFORMATION: Leu2
<220> FEATURE:
<223> OTHER INFORMATION: Leu2

<400> SEQUENCE: 115

```
Met Ser Lys Asn Ile Val Val Leu Pro Gly Asp His Val Gly Lys Glu
 1               5                  10                  15

Val Thr Asp Glu Ala Ile Lys Val Leu Asn Ala Ile Ala Glu Val Arg
            20                  25                  30

Pro Glu Ile Lys Phe Asn Phe Gln His His Leu Ile Gly Gly Ala Ala
        35                  40                  45

Ile Asp Ala Thr Gly Thr Pro Leu Pro Asp Glu Ala Leu Glu Ala Ser
    50                  55                  60

Lys Lys Ala Asp Ala Val Leu Leu Gly Ala Val Gly Gly Pro Lys Trp
65                  70                  75                  80

Gly Thr Gly Ala Val Arg Pro Glu Gln Gly Leu Leu Lys Ile Arg Lys
                85                  90                  95

Glu Leu Gly Leu Tyr Ala Asn Leu Arg Pro Cys Asn Phe Ala Ser Asp
            100                 105                 110

Ser Leu Leu Asp Leu Ser Pro Leu Lys Pro Glu Tyr Ala Lys Gly Thr
        115                 120                 125

Asp Phe Val Val Arg Glu Leu Val Gly Gly Ile Tyr Phe Gly Glu
    130                 135                 140

Arg Lys Glu Asp Glu Gly Asp Gly Val Ala Trp Asp Ser Glu Lys Tyr
145                 150                 155                 160

Ser Val Pro Glu Val Gln Arg Ile Thr Arg Met Ala Ala Phe Leu Ala
                165                 170                 175

Leu Gln Gln Asn Pro Pro Leu Pro Ile Trp Ser Leu Asp Lys Ala Asn
            180                 185                 190

Val Leu Ala Ser Ser Arg Leu Trp Arg Lys Thr Val Glu Glu Thr Ile
        195                 200                 205

Lys Thr Glu Phe Pro Gln Leu Thr Val Gln His Gln Leu Ile Asp Ser
    210                 215                 220

Ala Ala Met Ile Leu Val Lys Ser Pro Thr Lys Leu Asn Gly Val Val
225                 230                 235                 240

Ile Thr Asn Asn Met Phe Gly Asp Ile Ile Ser Asp Glu Ala Ser Val
                245                 250                 255

Ile Pro Gly Ser Leu Gly Leu Leu Pro Ser Ala Ser Leu Ala Ser Leu
            260                 265                 270

Pro Asp Thr Asn Lys Ala Phe Gly Leu Tyr Glu Pro Cys His Gly Ser
        275                 280                 285

Ala Pro Asp Leu Pro Ala Asn Lys Val Asn Pro Ile Ala Thr Ile Leu
    290                 295                 300
```

Ser Ala Ala Met Met Leu Lys Leu Ser Leu Asp Leu Val Glu Glu Gly
305                 310                 315                 320

Arg Ala Leu Glu Glu Ala Val Arg Asn Val Leu Asp Ala Gly Val Arg
                325                 330                 335

Thr Gly Asp Leu Gly Gly Ser Asn Ser Thr Thr Glu Val Gly Asp Ala
                340                 345                 350

Ile Ala Lys Ala Val Lys Glu Ile Leu Ala
            355                 360

<210> SEQ ID NO 116
<211> LENGTH: 499
<212> TYPE: DNA
<213> ORGANISM: Saccharomyces cerevisiae
<220> FEATURE:
<223> OTHER INFORMATION: pNUP57
<220> FEATURE:
<223> OTHER INFORMATION: pNUP57

<400> SEQUENCE: 116
tcatctgcgc aatgactatc aagaccttct gcaagaattt caaatctcac tgaaaatctt     60
gaccgaaaag tgtcttgaaa acccatcaag cctgcaaaac ctatctttga cattagtctc    120
cattataaaa acggcatagt tgggagaaaa cttttcatac ttcaattgtg gactgatata    180
agtattttgg ttttgcccgc atgatcatcc cacatggcta cagcagttct ctcataggaa    240
atagtacaat agctacgtga tataatctaa ataattgttg ccaatgtgta attatatcat    300
tttgaacgtt cgcgaaatgg attattttca aaattttgt ttcttgaaat gagtaaaagc     360
aaaagtccaa ctctccaagt cgatgtaaac aacttttgc caagggact gaaagactaa      420 atcgaggatt atcccgttca aactattcca gaaacgctcg ttagtaacaa agacatacc     480 ttgttgacca attgatcac                                                499

<210> SEQ ID NO 117
<211> LENGTH: 451
<212> TYPE: DNA
<213> ORGANISM: Saccharomyces cerevisiae
<220> FEATURE:
<223> OTHER INFORMATION: pGAP1
<220> FEATURE:
<223> OTHER INFORMATION: pGAP1

<400> SEQUENCE: 117
cactttcacc agatcccaaa tgtcccgccc ctattcccgt gttccatcac gtaccataac     60
ttaccatttc atcacgttct ctatggcaca ctggtactgc ttcgactgct ttgcttcatc    120
ttctctatgg gccaatgagc taatgagcac aatgtgctgc gaaataaagg gatatctaat    180
ttatattatt acattataat atgtactagt gtggttattg gtaattgtac ttaattttga    240
tatataaagg gtggatcttt tcatttga atcagaattg gaattgcaac ttgtctcttg      300
tcactattac ttaatagtaa ttatatttct tattaacctt tttttaagt caaaacacca     360 aggacaagaa ctactcttca aaggtatttc aagttatcat acgtctcaca cacgcttcac    420
agtttcaagt aaaaaaaaag aatattacac a                                  451

<210> SEQ ID NO 118
<211> LENGTH: 998
<212> TYPE: DNA
<213> ORGANISM: Saccharomyces cerevisiae
<220> FEATURE:
<223> OTHER INFORMATION: pJEN1
<220> FEATURE:
<223> OTHER INFORMATION: pJEN1

<400> SEQUENCE: 118

```
aatgtgttta taaattattt tttttgctgg tagcaaaatc aactcattgt cttccattca    60
gagtctaatc gaacgttatc gcaatgcttg cacactttta aacaatacga tttagtttaa   120
gtggatggac ccccacgctt agtgttccac aggtttgtcc ccactgtttt tacattccac   180
tgtacatttt tgcaatagaa ggtcattgta tgctaccttg ggcggctaag aatacctgta   240
aaaatttgga gaaattagat tcgtaaagaa tgactcgcaa cgactccaat gatttcttct   300
tttcacccct tgaacggccg atatccgcgc gggatcctga ccccgcaatt tactccacta   360
gaccggcgtg tttctctttt tccttttcct ggggttagag cccaagagct aatagccgac   420
aaacggactc caaaaaaaaa aggaggcaca ggacaaacgc agcacctgcg tcattcacgc   480
tgaagcggca gcaagcattt tcgatcagct ccaattaaat gaagactatt cgccgtaccg   540
ttcccagatg ggtgcgaaag tcagtgatcg aggaagttat tgagcgcgcg gcttgaaact   600
atttctccat ctcagagccg ccaagcctac cattattctc caccaggaag ttagtttgta   660
agcttctgca caccatccgg acgtccataa ttcttcactt aacggtcttt tgccccccct   720
tctactataa tgcattagaa cgttacctgg tcatttggat ggagatctaa gtaacactta   780
ctatctccta tggtactatc ctttaccaaa aaaaaaaaa aaaaaaaaa aaaaaatcag     840
caaagtgaag taccctcttg atgtataaat acattgcaca tcattgttga gaaatagttt   900
tggaagttgt ctagtccttc tcccttagat ctaaaggaa gaagagtaac agtttcaaaa    960
gttttttcctc aaagagatta aatactgcta ctgaaaat                          998
```

<210> SEQ ID NO 119
<211> LENGTH: 450
<212> TYPE: DNA
<213> ORGANISM: Saccharomyces cerevisiae
<220> FEATURE:
<223> OTHER INFORMATION: pICL1
<220> FEATURE:
<223> OTHER INFORMATION: pICL1

<400> SEQUENCE: 119

```
ttttgctact cgtcatccga tgagaaaaac tgttcccttt tgccccaggt ttccattcat    60
ccgagcgatc acttatctga cttcgtcact ttttcatttc atccgaaaca atcaaaactg   120
aagccaatca ccacaaaatt aacactcaac gtcatctttc actacccttt acagaagaaa   180
atatccatag tccggactag catcccagta tgtgactcaa tattggtgca aaagagaaaa   240
gcataagtca gtccaaagtc cgcccttaac caggcacatc ggaattcaca aaacgtttct   300
ttattatata aaggagctgc ttcactggca aaattcttat tatttgtctt ggcttgctaa   360
tttcatctta tccttttttt cttttcacac ccaaatacct aacaattgag agaaaactct   420
tagcataaca taacaaaaag tcaacgaaaa                                    450
```

<210> SEQ ID NO 120
<211> LENGTH: 598
<212> TYPE: DNA
<213> ORGANISM: Saccharomyces cerevisiae
<220> FEATURE:
<223> OTHER INFORMATION: pADH2
<220> FEATURE:
<223> OTHER INFORMATION: pADH2

<400> SEQUENCE: 120

```
tatcttaact gatagtttga tcaaaggggc aaaacgtagg ggcaaacaaa cggaaaaatc    60
```

-continued

```
gtttctcaaa ttttctgatg ccaagaactc taaccagtct tatctaaaaa ttgccttatg      120
atccgtctct ccggttacag cctgtgtaac tgattaatcc tgcctttcta atcaccattc      180
taatgtttta attaagggat tttgtcttca ttaacggctt tcgctcataa aaatgttatg      240
acgttttgcc cgcaggcggg aaaccatcca cttcacgaga ctgatctcct ctgccggaac      300
accgggcatc tccaacttat aagttggaga aataagagaa tttcagattg agagaatgaa      360
aaaaaaaaaa aaaaaaggca gaggagagca tagaaatggg gttcactttt tggtaaagct      420
atagcatgcc tatcacatat aaatagagtg ccagtagcga cttttttcac actcgaaata      480
ctcttactac tgctctcttg ttgtttttat cacttcttgt ttcttcttgg taaatagaat      540
atcaagctac aaaaagcata caatcaacta tcaactatta actatatcgt aatacaca      598

<210> SEQ ID NO 121
<211> LENGTH: 793
<212> TYPE: DNA
<213> ORGANISM: Saccharomyces cerevisiae
<220> FEATURE:
<223> OTHER INFORMATION: pMLS1
<220> FEATURE:
<223> OTHER INFORMATION: pMLS1

<400> SEQUENCE: 121
tgtctaatgc gaaggtactt ttattttttt cagattcaaa gcaatattat ttagacaatt       60
gatactaagt gagcttaagg aggattaaac aactgtggaa tccttcacaa ggattcaata      120
tttgtttttc ctggttattt tgccatcatt caactttcct cagacgtaaa attcgtgctt      180
agtgatgtct caatattccc gcagggtaat aaaattcaat aactatcact atatacgcaa      240
cagtattacc ctacattgct atcggctcaa tggaaatccc catatcatag cttccattgg      300
gccgatgaag ttagtcgacg gatagaagcg gttgtcccct ttcccggcga gccggcagtc      360
gggccgaggt tcggataaat tttgtattgt gttttgattc tgtcatgagt attacttatg      420
ttctctttag gtaaccccag gttaatcaat cacagtttca taccggctag tattcaaatt      480
atgacttttc ttctgcagtg tcagccttac gacgattatc tatgagcttt gaatatagtt      540
tgccgtgatt cgtatcttta attggataat aaaatgcgaa ggatcgatga cccttattat      600
tatttttcta cactggctac cgatttaact catcttcttg aaagtatata agtaacagta      660
aaatataccg tacttctgct aatgttattt gtcccttatt tttcttttct tgtcttatgc      720
tatagtacct aagaataacg actattgttt tgaactaaac aaagtagtaa aagcacataa      780
aagaattaag aaa                                                       793
```

ECTOINE-PRODUCING YEAST

SEQUENCE LISTING

This application includes a sequence listing which has been submitted in ST.25 format and is hereby incorporated by reference in its entirety. Said sequence listing, created on Dec. 21, 2020, is in a file named 2021-02-11_CorrectedSequenceListing.txt and is 159,266 bytes in size.

FIELD OF THE INVENTION

The present invention relates to the field of bio-production of ectoine.

BACKGROUND OF THE INVENTION

Ectoine (1, 4, 5, 6-tetrahydro-2-methyl-4-pyrimidinecarboxylic acid) is an heterocyclic amino acid naturally produced by halophilic organisms in nature. Indeed, in order to survive in salty environments, these organisms produce ectoine as compatible solute which serves as osmotic counterweights.

Ectoine is indeed also capable of protecting nucleic acids, proteins, cell membranes as well as whole cells against denaturation caused by numerous aggressions from the external environment, such as UV radiations, heating, freezing or chemical agents, but also against denaturation due to drying (see for example Lentzen G et al. Appl Microbiol Biot. 2006; 72:623-34, and Graf R et al. Clin Dermatol. 2008; 26:326-33). As such it is used in cosmetic for skincare.

Ectoine has moreover been found to be interesting as proteins stabilizer, cosmetic additive, PCR enhancer and drying protective agent for microorganisms.

Due to these advantageous properties, ectoine is increasingly produced through bacterial processes using in particular halophilic bacteria such as *Halomonas elongata*. However, these methods necessitate a high salt concentration which complexifies the process and leads to an increase of the costs involved considering the important corrosion of the equipment.

Furthermore, the production of essential amino acids such as ectoine through the biosynthetic pathways of bacteria and yeasts requires an important amount of reducing power in the form of NADPH. However, the main pathway for the metabolisation of glucose in these microorganisms, and in particular in yeasts, is glycolysis followed by fermentation which only produces NADH. Maintaining an acceptable NADPH/NADH balance within the microorganism, albeit complex, is therefore essential to optimize bio-production of ectoine while maintaining a viable recombinant microorganism.

Accordingly, there is still a need in the art for further ectoine production methods allowing its highly efficient synthesis and secretion.

SUMMARY OF THE INVENTION

The present invention accordingly relates to an ectoine-producing recombinant yeast, in the genome of which:
  (A) (i) at least one nucleic acid encoding an aspartokinase is overexpressed and/or is under the control of an inducible or repressible promoter; and/or
  (ii) at least one nucleic acid encoding an aspartate kinase is overexpressed and/or is under the control of an inducible or repressible promoter;
  (B) at least one nucleic acid encoding an aspartate semi-aldehyde dehydrogenase and/or at least one nucleic acid encoding an aspartate semi-aldehyde dehydrogenase that can use as coenzyme both NAD and NADP is overexpressed and/or is under the control of an inducible or repressible promoter;
  (C) at least one nucleic acid encoding a diaminobutyrate aminotransferase is overexpressed and/or is under the control of an inducible or repressible promoter;
  (D) (i) at least one nucleic acid encoding an homoserine-O-acetyltransferase MET2 is overexpressed and/or is under the control of an inducible or repressible promoter;
  (ii) at least one nucleic acid encoding an homoserine-O-acetyltransferase METX is overexpressed and/or is under the control of an inducible or repressible promoter, and/or
  (iii) at least one nucleic acid encoding a diaminobutyric acid acetyltransferase is overexpressed and/or is under the control of an inducible or repressible promoter;
  (E) at least one nucleic acid encoding an ectoine synthase is overexpressed and/or is under the control of an inducible or repressible promoter;
  (F) (i) at least one, preferably all, endogenous nucleic acid encoding an homoserine dehydrogenase has been deleted and/or interrupted, and/or
  (ii) at least one, preferably all, nucleic acid encoding an homoserine dehydrogenase is independently:
  under the control of an inducible or repressible promoter;
  under the control of a weak promoter; and/or
  in a destabilized form.

As illustrated in the enclosed examples, the recombinant yeasts of the invention have an increased ectoine production.

Said advantageous property can be further increased by also recombining the yeast with additional modifications described here-after.

An ectoine-producing recombinant yeast can consequently advantageously be used in a method for producing ectoine as described here-after or be used for the production of ectoine.

The present invention further relates to a method for producing ectoine, said method comprising the steps of:
  (a) culturing a recombinant yeast of the invention in a culture medium; and
  (b) recovering the ectoine from said culture medium.

Preferably, the culture medium comprises at least a carbon source, preferably a carbon source selected from the group consisting of glucose and sucrose.

The invention also relates to the use of a recombinant yeast according to the invention for the production of ectoine.

DETAILED DESCRIPTION OF THE INVENTION

The inventors have conceived genetically modified microorganisms, and especially genetically modified yeasts, having an increased ability to produce ectoine, as compared to the parent microorganisms, and especially as compared to the parent yeasts.

These genetically modified microorganisms, including these genetically modified yeasts, are described throughout the present specification.

Definitions

The term "microorganism", as used herein, refers to a yeast which is not modified artificially. The microorganism may be "donor" if it provides genetic element to be integrated in the microorganism "acceptor" which will express this foreign genetic element or if it used as tool for genetic constructions or protein expressions. The microorganism of the invention is chosen among yeast which expresses genes for the biosynthesis of ectoine.

The term "recombinant microorganism" or "genetically modified microorganism" or "recombinant yeast" or "genetically modified yeast", as used herein, refers to a yeast genetically modified or genetically engineered. It means, according to the usual meaning of these terms, that the microorganism of the invention is not found in nature and is modified either by introduction or by deletion or by modification of genetic elements from equivalent microorganism found in nature. It can also be modified by forcing the development and evolution of new metabolic pathways by combining directed mutagenesis and evolution under specific selection pressure (see for instance WO 2004/076659).

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganism, like yeast, with exogenous DNA is a routine task for those skilled in the art. In particular, a genetic modification of a microorganism according to the invention, more particularly the genetic modification(s) herein defined, may be carried out by using CRISPR-Cas systems, as described in DiCarlo et al. (Nucl. Acids Res., vol. 41, No. 7, 2013: 4336-4343).

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, in the down-regulation and/or attenuation of the activity of the endogenous gene product. Another way to enhance expression of endogenous genes is to introduce one or more supplementary copies of the gene onto the chromosome or a plasmid.

The term "exogenous gene" means that the gene was introduced into a microorganism, by means well known by the man skilled in the art, whereas this gene is not naturally occurring in the wild-type microorganism. Microorganism can express exogenous genes if these genes are introduced into the microorganism with all the elements allowing their expression in the host microorganism. Transforming microorganisms with exogenous DNA is a routine task for the man skilled in the art. Exogenous genes may be integrated into the host chromosome, or be expressed extra-chromosomally from plasmids or vectors. A variety of plasmids, which differ with respect to their origin of replication and their copy number in the cell, are all known in the art. The sequence of exogenous genes may be adapted for its expression in the host microorganism. Indeed, the man skilled in the art knows the notion of codon usage bias and how to adapt nucleic sequences for a particular codon usage bias without modifying the deduced protein.

The term "heterologous gene" means that the gene is derived from a species of microorganism different from the recipient microorganism that expresses it. It refers to a gene which is not naturally occurring in the microorganism.

In the present application, all genes are referenced with their common names and with references to their nucleotide sequences and, the case arising, to their amino acid sequences. Using the references given in accession number for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerated probes to clone the corresponding gene in another organism.

The man skilled in the art knows different means to modulate, and in particular up-regulate or down-regulate, the expression of endogenous genes. For example, a way to enhance expression of, or over express, endogenous genes is to introduce one or more supplementary copies of the gene onto the chromosome or a plasmid.

Another way is to replace the endogenous promoter of a gene with a stronger promoter. These promoters may be homologous or heterologous. Promoters particularly interesting in the present invention are described in more detail elsewhere in the present specification.

The nucleic acid expression construct may further comprise 5' and/or 3' recognition sequences and/or selection markers.

The term "overexpression" means that the expression of a gene or of an enzyme is increased as compared to the non-modified microorganism. Increasing the expression of an enzyme is obtained by increasing the expression of a gene encoding said enzyme. Increasing the expression of a gene may be carried out by all techniques known by the one skilled in the art. In this regard, it may be notably cited the implementation of a strong promoter upstream the nucleic acid intended to be overexpressed or the introduction of a plurality of copies of the said nucleic acid between a promoter, especially a strong promoter, and a terminator.

The term "underexpression" means that the expression of a gene or of an enzyme is decreased as compared to the non-modified microorganism. Decreasing the expression of an enzyme is obtained by decreasing the expression of a gene encoding said enzyme. Decreasing the expression of a gene may be carried out by all techniques known by the one skilled in the art. In this regard, it may be notably cited the implementation of a weak promoter upstream the nucleic acid intended to be underexpressed. It may be also cited the implementation of a nucleic acid encoding a variant of the said enzyme that is less active than the parent enzyme or a variant of the said enzyme that is more rapidly degraded in the cell than the parent enzyme. Variants of a parent enzyme that is more rapidly degraded that the said parent enzyme encompass degron-tagged enzymes. It may also be cited the decrease of the expression of a transcription activator of the gene of interest.

The term "inducible promoter" is used to qualify a promoter whose activity is induced, i.e. increased:
  in the presence of one or more particular metabolite(s).
    The higher the metabolite concentration in the medium, the stronger the promoter activity; or
  in the presence of a low concentration, or in the absence, of one or more metabolite(s). These metabolites are different from those whose increasing presence induces the activity of the promoter. The lower the metabolite concentration in the medium, the stronger the promoter activity.

The term "repressible promoter" is used to qualify a promoter whose activity is repressed, i.e. reduced:
- in the presence of one or more particular metabolite(s). The higher the metabolite concentration in the medium, the weaker the promoter activity; or
- in the presence of a low concentration, or in the absence, of one or more metabolite(s). These metabolites are different from those whose increasing presence represses the activity of the promoter. The lower the metabolite concentration in the medium, the weaker the promoter activity.

A used herein, a "degron-tagged" enzyme means an enzyme comprising an added protein-degradation signal amino acid sequence that serves as a destruction signal that will cause the said enzyme to be the subject of a degradation, which may be either (i) a ubiquitin-independent degradation or (ii) an ubiquitin-dependent degradation. The said added protein-degradation signal, that is also termed "degron" in the art, encompasses an amino acid sequence that serves as a destruction signal, the said amino acid sequence consisting of a transferrable degradation signal causing a targeted protein degradation. Degrons encompass "N-degrons", which are transferrable N-terminal amino acids that cause the target protein degradation following the well-known N-end rule (Bachmair et al., 1986, Science, Vol. 234 (4773): 179-186). The unstable nature of the N-degron is attributed to its first amino acids, which are prone to acetylation or arginylation modifications and ultimately lead to ubiquitination and degradation. Generally, a degron requires at least two components to ensure targeted protein degradation: (i) a target degradation recognition tag, such as a poly-ubiquitin tag and (ii) an unstructured amino acid sequence in close proximity to the degradation recognition tag. For degron-tagging a protein, and especially herein for degron-tagging an enzyme, the one skilled in the art may refer to Yu et al. (2015, Current Opinion in Biotechnology, Vol. 36: 199-204), Cho et al. (2010, Genes & Development, Vol. 24: 438-442), or to Fortmann et al. (2015, J Mol Biol, Vol. 427 (17): 2748-2756), Ravid et al. (2008, Nat Rev Mol Cell Biol, Vol. 9(9): 679-690) and Hochstrasser (1996, Annu Rev Genet, Vol. 30: 405-439).

The "activity" of an enzyme is used interchangeably with the term "function" and designates, in the context of the invention, the capacity of an enzyme to catalyze a desired reaction.

The terms "reduced activity" or "attenuated activity" of an enzyme mean either a reduced specific catalytic activity of the protein obtained by mutation in the amino acids sequence and/or decreased concentrations of the protein in the cell obtained by mutation of the nucleotide sequence or by deletion of the cognate corresponding gene or also by degron-tagging of the protein.

The term "enhanced activity" of an enzyme designates either an increased specific catalytic activity of the enzyme, and/or an increased quantity/availability of the enzyme in the cell, obtained for example by overexpression of the gene encoding the enzyme.

The terms "encoding" or "coding" refer to the process by which a polynucleotide, through the mechanisms of transcription and translation, produces an amino-acid sequence.

The gene(s) encoding the enzyme(s) considered in the present invention can be exogenous or endogenous.

"Attenuation" of genes means that genes are expressed at an inferior rate than in the non-modified microorganism. The attenuation may be achieved by means and methods known to the man skilled in the art and contains gene deletion obtained by homologous recombination, gene attenuation by insertion of an external element into the gene or gene expression under a weak promoter. The man skilled in the art knows a variety of promoters which exhibit different strengths and which promoter to use for a weak genetic expression.

The methods implemented in the present invention preferably require the use of one or more chromosomal integration constructs for the stable introduction of a heterologous nucleotide sequence into a specific location on a chromosome or for the functional disruption of one or more target genes in a genetically modified microbial cell. In some embodiments, disruption of the target gene prevents the expression of the related functional protein. In some embodiments, disruption of the target gene results in the expression of a non-functional protein from the disrupted gene.

Parameters of chromosomal integration constructs that may be varied in the practice of the present invention include, but are not limited to, the lengths of the homologous sequences; the nucleotide sequence of the homologous sequences; the length of the integrating sequence; the nucleotide sequence of the integrating sequence; and the nucleotide sequence of the target locus. In some embodiments, an effective range for the length of each homologous sequence is 20 to 5,000 base pairs, preferentially 50 to 100 base pairs. In particular embodiments, the length of each homologous sequence is about 50 base pairs. For more information on the length of homology required for gene targeting, see D. Burke et al., Methods in yeast Genetics—A cold spring harbor laboratory course Manual (2000).

In some embodiments, (a) disrupted gene(s) in which the above-mentioned DNA construct(s) is/are intended to be inserted may advantageously comprises one or more selectable markers useful for the selection of transformed microbial cells. Preferably, said selectable marker(s) are comprised in the DNA construct(s) according to the present invention.

In some embodiments, the selectable marker is an antibiotic resistance marker. Illustrative examples of antibiotic resistance markers include, but are not limited to the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Auerobasidin A (AbA); the HPH gene product of *Klebsiella pneumonia* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin).

In some embodiments, the antibiotic resistance marker is deleted after the genetically modified microbial cell of the invention is isolated. The man skilled in the art is able to choose suitable marker in specific genetic context.

In some embodiments, the selectable marker rescues an auxotrophy (e.g., a nutritional auxotrophy) in the genetically modified microbial cell. In such embodiments, a parent microbial cell comprises a functional disruption in one or more gene products that function in an amino acid or nucleotide biosynthetic pathway, such as, for example, the HIS3, LEU2, LYS1, LYS2, MET 15, TRP1, ADE2, and URA3 gene products in yeast, which renders the parent microbial cell incapable of growing in media without supplementation with one or more nutrients (auxotrophic phenotype). The auxotrophic phenotype can then be rescued by transforming the parent microbial cell with a chromosomal integration encoding a functional copy of the disrupted gene product (NB: the functional copy of the gene can originate from close species, such as *Kluveromyces*, *Candida* etc.), and the genetically modified microbial cell generated can be selected for based on the loss of the auxotrophic phenotype of the parent microbial cell.

For each of the nucleic acid sequences comprising a promoter sequence, a coding sequence (e.g. an enzyme coding sequence), or a terminator sequence, reference sequences are described herein. The present description also encompasses nucleic acid sequences having specific percentages of nucleic acid identity, with a reference nucleic acid sequence.

For each or the amino acid sequences of interest, reference sequences are described herein. The present description also encompasses amino acid sequences (e.g. enzyme amino acid sequences), having specific percentages of amino acid identity, with a reference amino acid sequence.

For obvious reasons, in all the present description, a specific nucleic acid sequence or a specific amino acid sequence which complies with, respectively, the considered nucleotide or amino acid identity, should further lead to obtaining a protein (or enzyme) which displays the desired biological activity. As used herein, the "percentage of identity" between two nucleic acid sequences or between two amino acid sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The identity percentage is calculated by determining the number of positions at which an identical nucleic base, or an identical amino-acid residue, can be noted for both compared sequences, then by dividing the number of positions at which identity can be observed between both nucleic bases, or between both amino-acid residues, by the total number of positions in the comparison window, then by multiplying the result by hundred to obtain the percentage of nucleotide identity between the two sequences or the percentage of amino acid identity between the two sequences.

The comparison of the sequence optimal alignment may be performed by a computer using known algorithms.

Most preferably, the sequence identity percentage is determined using the CLUSTAL W software (version 1.82) the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

The "fermentation" or "culture" is generally conducted in fermenters with an appropriate culture medium adapted to the microorganism being cultivated, containing at least one simple carbon source, and if necessary co-substrates.

Microorganisms disclosed herein may be grown in fermentation media for the production of a product from oxaloacetate. For maximal production of ectoine, the microorganism strains used as production hosts preferably have a high rate of carbohydrate utilization. These characteristics may be conferred by mutagenesis and selection, genetic engineering, or may be natural. Fermentation media, or "culture medium", for the present cells may contain at least about 10 g/L of glucose. Additional carbon substrates may include but are not limited to monosaccharides such as fructose, mannose, xylose and arabinose; oligosaccharides such as lactose maltose, galactose, or sucrose; polysaccharides such as starch or cellulose or mixtures thereof and unpurified mixtures from renewable feedstocks such as cheese whey permeate cornsteep liquor, sugar beet molasses, and barley malt. Other carbon substrates may include glycerol.

Hence, it is contemplated that the source of carbon utilized in the present invention may encompass a wide variety of carbon containing substrates and will only be limited by the choice of organism.

Although it is contemplated that all of the above-mentioned carbon substrates and mixtures thereof are suitable in the present invention, preferred carbon substrates are glucose, fructose, and sucrose, or mixtures of these with C5 sugars such as xylose and/or arabinose for microorganisms modified to use C5 sugars, and more particularly glucose.

A preferred carbon substrate is glucose.

In addition to an appropriate carbon source, fermentation media may contain suitable minerals, salts, cofactors, buffers and other components, known to those skilled in the art, suitable for the growth of the cultures and promotion of the enzymatic pathway necessary for the production of the desired product.

Besides, additional genetic modifications suitable for the growth of recombinant microorganisms according to the invention may be considered.

The terms "Aerobic conditions" refers to concentrations of oxygen in the culture medium that are sufficient for an aerobic or facultative anaerobic microorganism to use dioxygene as a terminal electron acceptor.

"Microaerobic condition" refers to a culture medium in which the concentration of oxygen is less than that in air, i.e. oxygen concentration up to 6% $O_2$.

An "appropriate culture medium" designates a medium (e.g. a sterile, liquid medium) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like. The term "carbon source" or "carbon substrate" or "source of carbon" according to the present invention denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

General features of genetic modifications introduced according to the invention

Genes are over expressed by two kinds of non mutually exclusive modifications:

Placing them under the control of a strong promoter; and/or

Inserting a plurality of copies of the considered gene.

All the genome modifications are inserted in yeast according to known genetic engineering techniques:

The successive genes included in a gene construct that is introduced in the yeast genome according to the invention are of the following structure:

Prom$_1$-ORF$_1$-term$_1$-ORF$_2$-gene$_2$-term$_2$- . . . / . . . -Prom$_n$-ORF$_n$-term$_n$, wherein:

Prom1 is a sequence regulating the expression of the coding sequence ORF1,

ORF1 is a nucleic acid sequence encoding a desired protein PROT1, and especially a desired enzyme PROT1, Term1 is a transcription terminator sequence that mediates transcriptional termination by providing signals in the newly synthesized mRNA that trigger processes which release the mRNA from the transcriptional complex, and "1", "2", . . . / . . . "n" may or may not describe the same ORF (Open Reading Frame), promoter or terminator. The order of the genes does not matter. "n" is an integer usually ranging from 5 and 20. These constructs are inserted in one of the yeast chromosome at a controlled location. In some embodiments, the insertion site is not essential for the functionality of the inserted construct, nor for the viability of the resulting genetically modified yeast.

When the yeast is for example *Saccharomyces cerevisiae*, genes introduced in the yeast genome and originating from other organisms than *Saccharomyces cerevisiae* are generally "transcoded" (generally codon-optimized"), meaning that these genes are synthesized with an optimal codon usage for expression in *S. cerevisiae*. The nucleotide sequence (and not the protein sequence) of some genes from *S. cerevisiae* has also been modified ("transcoded") to minimize recombination with an endogenous copy of the said gene.

Genes may be deleted through standard procedures used in yeast genetic engineering. In some embodiments, the genes targeted for deletion may be interrupted by insertion of one of the above described gene constructs, or alternatively the genes targeted for deletion are replaced by a short stretch of nucleotide.

Down regulating gene expression may be obtained by disrupting the endogenous copy of the gene and replacing it with a copy of the ORF under the control of a weak promoter. A list and sequences of weak promoters is described elsewhere in the present specification.

A gene may be rendered "inducible or repressible" by deleting the endogenous copy of the gene (if necessary) and placing a new copy of the ORF under the control of an inducible or repressible promoter. An inducible or repressible promoter is a promoter which activity is modulated or controlled, i.e. either increased or decreased upon a change in the environmental conditions or external stimuli. Induction or repression may be artificially controlled, which encompasses induction or repression by abiotic factors such as chemical compounds not found naturally in the organism of interest, light, oxygen levels, heat or cold. A list and sequence of inducible or repressible promoters is described elsewhere in the present specification.

As already specified elsewhere herein, a protein may be underexpressed by destabilization by using "the degron" technology which is described in Yu et al. 2015, (Current Opinion in Biotechnology, Vol. 36: 199-204). In brief this technology consists in introducing in the protein sequence a modification that targets it for degradation. It can consist only in the two first amino acids following the principle known as the N-end rule, or a larger sequence targeting the whole protein to the ubiquitin-preoteasome degradation pathway.

Recombinant Yeast According to the Invention

The inventors have conceived recombinant microorganisms, and especially recombinant yeasts, having an increased ability of producing ectoine.

The present invention relates to recombinant yeasts having an increased ectoine production, and wherein the increased ectoine production is obtained through a plurality of alterations that have been introduced in the genome thereof, by genetic engineering methods.

This invention pertains to an ectoine-producing recombinant yeast, in the genome of which:

(A) (i) at least one nucleic acid encoding an aspartokinase HOM3 is overexpressed and/or is under the control of an inducible or repressible promoter; and/or (ii) at least one nucleic acid encoding an aspartate kinase AK is overexpressed and/or is under the control of an inducible or repressible promoter;

(B) at least one nucleic acid encoding an aspartate semialdehyde dehydrogenase HOM2 and/or at least one nucleic acid encoding an aspartate semi-aldehyde dehydrogenase HOM2 that can use as coenzyme both NAD and NADP is overexpressed and/or is under the control of an inducible or repressible promoter;

(C) at least one nucleic acid encoding a diaminobutyrate aminotransferase EctB is overexpressed and/or is under the control of an inducible or repressible promoter;

(D) (i) at least one nucleic acid encoding an homoserine-O-acetyltransferase MET2 is overexpressed and/or is under the control of an inducible or repressible promoter;

(ii) at least one nucleic acid encoding an homoserine-O-acetyltransferase METX is overexpressed and/or is under the control of an inducible or repressible promoter, and/or (iii) at least one nucleic acid encoding a diaminobutyric acid acetyltransferase EctA is overexpressed and/or is under the control of an inducible or repressible promoter;

(E) at least one nucleic acid encoding an ectoine synthase EctC is overexpressed and/or is under the control of an inducible or repressible promoter;

(F) (i) at least one, preferably all, endogenous nucleic acid encoding an homoserine dehydrogenase HOM6 has been deleted, and/or (ii) at least one, preferably all, nucleic acid encoding an homoserine dehydrogenase HOM6 is independently:

under the control of an inducible or repressible promoter;

under the control of a weak promoter; and/or in a destabilized form.

The inventors have found that an increased production of ectoine by yeast cells may be reached by introducing in the genome of these yeast cells a plurality of genetic alterations. As it is fully described herein, the said plurality of genetic alterations encompass an overexpression of certain genes, a controlled expression of certain other genes, as well as repression or deletion of further other genes.

The increased ectoine production by yeast cells has been reached by the inventors by optimizing the metabolism of oxaloacetate and acetyl-CoA, so as to direct the subsequent artificially modified metabolic pathway mainly towards ectoine production whereas in the same time maintaining an optimal viability of the resulting genetically modified yeast cells.

After a lengthy research time period, the present inventors have determined that a high ectoine production by yeast cells is obtained by increasing the conversion of oxaloacetate into the successive intermediate metabolites phospho-aspartyl and aspartyl-semialdehyde, and additionally enhancing the conversion of aspartyl-semialdehyde into ectoine, while, notably, maintaining a redox status and more specifically an adapted NADH/NADPH balance allowing a good viability of the resulting recombinant yeast cells. This last point is essential and represented a significant challenge for the inventors throughout their research work.

The proposed solution according to the invention unexpectedly allows maintaining a viable NADH/NADPH equilibrium in the yeast cells throughout the ectoine-production pathway through the consumption of less reducing power, the comsumption of reducing power in the form of NADH rather than NADPH, and/or the production of NADH instead of NADPH.

As disclosed in detail in the present specification, the resulting recombinant yeast cells are genetically modified so as to effect an over expression and/or a controlled expression of (i) an aspartokinase-encoding gene (HOM3) and/or of (ii) an aspartate kinase-encoding gene (AK), in particular of an aspartate kinase-encoding gene (AK), preferably an over expression of an aspartate kinase gene (AK).

Further, a recombinant yeast according to the invention comprises further genetic modifications for an optimal use of the intermediate metabolite phospho-aspartyl for aspartyl-semialdehyde production, the said further genetic modifications comprising an over expression and/or the controlled expression of an aspartate semi-aldehyde dehydrogenase-encoding gene (HOM2) and/or of a gene encoding an aspartate semi-aldehyde dehydrogenase that can use as coenzyme both NADH and NADPH.

Moreover, a recombinant yeast according to the invention comprises further genetic modifications for an optimal use of the intermediate metabolite aspartyl-semialdehyde for ectoine production, the said further genetic modifications comprising (i) an over expression and/or the controlled expression of a diaminobutyrate aminotransferase gene (EctB), (ii) an over expression and/or the controlled expression of a homoserine O-acetyltransferase-encoding gene (MET2; METX) and/or of a diaminobutyric acid acetyltransferase gene (EctA), (iii) an over expression and/or the controlled expression of an ectoine synthase gene (EctC) and (iv) the under expression and/or the controlled expression of an homoserine dehydrogenase gene (HOME).

In some embodiments of a recombinant yeast according to the invention, the said yeast comprises further genetic modifications for an optimal use of the intermediate metabolite oxaloacetate for aspartate production, the said further genetic modifications comprising (i) an over expression and/or the controlled expression of an aspartate transaminase gene (AAT2) and/or (ii) an over expression and/or the controlled expression of a glutamate dehydrogenase that converts oxo-glutarate to glutamate gene (GDH).

In some embodiments of a recombinant yeast according to the invention, the said yeast comprises further genetic modifications for an optimal secretion of the produced ectoine, the said further genetic modifications comprising (i) the under expression and/or the controlled expression of a general amino acid permease gene (AGP3), (ii) the under expression and/or the controlled expression of a branched-chain amino-acid permease 3 gene (BAP3), (iii) the under expression and/or the controlled expression of a branched-chain amino-acid permease 2 gene (BAP2), (iv) the under expression and/or the controlled expression of a general amino acid permease gene (GAP1), (v) the under expression and/or the controlled expression of a high-affinity glutamine permease gene (GNP1), (vi) the under expression and/or the controlled expression of a general amino acid permease gene (AGP1), (vii) the under expression and/or the controlled expression of a low-affinity methionine permease gene (MUP3; MUP1), (viii) the over expression and/or the controlled expression of a probable transporter gene (AQR1) and/or (ix) the over expression and/or the controlled expression of a polyamine transporter 1 gene (TPO1).

In a particular embodiment, the at least one nucleic acid encoding a general amino acid permease, a branched-chain amino-acid permease 3, a branched-chain amino-acid permease 2, a general amino acid permease GAP1, a high-affinity glutamine permease GNP1, a general amino acid permease AGP1, a low-affinity methionine permease MUP3 and a high-affinity methionine permease MUP1 are, independently, nucleic acid from a yeast, preferably from *Saccharomyces cerevisiae*.

A recombinant yeast according to the invention produces ectoine with a higher yield than the parent yeast which does not contain the genetic modifications described above.

A recombinant yeast according to the invention has been genetically engineered so as to promote the expression of enzymes utilizing NADH rather than NADPH, such as an appropriate glutamate dehydrogenase or an appropriate aspartate semialdehyde dehydrogenase.

In some embodiments of a recombinant yeast according to the invention, the aspartate-semialdehyde dehydrogenase that are over expressed consist of the *S. cerevisiae* endogenous gene that is placed under the control of strong promoters and/or of inducible or repressible promoters.

In some embodiments, the aspartate-semialdehyde dehydrogenase is preferably encoded by the *S. cerevisiae* HOM2 gene.

In some embodiments, the aspartate-semialdehyde dehydrogenase is most preferably encoded by a variant of the *S. cerevisiae* HOM2 gene, which genes codes for a mutated HOM2 protein that uses both NAD and NADP, as it is shown in the examples herein. Such gene variant is for example illustrated in the examples and is called HOM2-2. It corresponds to the *S. cerevisiae* HOM2 gene mutated as discussed here-under.

The nature of the mutations aiming several amino acid residues in the aspartate-semialdehyde dehydrogenase variant in order to relaxe the high selectivity of HOM2 for NADP as coenzyme and enhance the affinity of the enzyme for NAD are known to the man skilled in the art and can for example be found in Faehnle, C. R. et al., Journal of Molecular Biology 1055-1068 (2005). In particular, the mutation S39 to E39 corresponding to the replacement of the nucleotides TCT in position 115 to 117 of the nucleotide sequence by the nucleotides GAG can be mentioned.

According to the nomenclature of the amino acids well known to the man skilled in the art, S represents a Serine and E represents a Glutamic acid.

In some embodiments, the aspartokinase is most preferably encoded by the *S. cerevisiae* HOM3 gene, as it is shown in the examples herein.

Aspartokinase-Encoding Gene Over Expression and/or Controlled Expression

In some embodiments of a recombinant yeast according to the invention, over expression of an aspartokinase-encoding gene is obtained by inserting, at selected location(s) of the yeast genome, one or more copies of an expression cassette comprising an aspartokinase coding sequence. Aspartokinase and an aspartokinase-encoding gene that are encompassed by the invention are detailed elsewhere in the present specification.

In some of these embodiments, the said one or more copies of an expression cassette comprising an aspartokinase coding sequence comprise(s) regulatory sequences allowing a strong expression of the aspartokinase, such as a strong promoter that is functional in yeast cells.

In addition to or as an alternative to these embodiments of a recombinant yeast according to the invention, at least one aspartokinase-encoding gene can be under the control of an inducible or repressible promoter that is functional in yeast cells.

In these embodiments, a controlled expression of an aspartokinase-encoding gene can be obtained by inserting, at the location of the natural yeast aspartokinase open reading frame, an inducible regulatory sequence, such as an inducible or repressible promoter, that replaces the endogenous promoter initially present in the yeast genome at this genome location.

Without wishing to be bound by any particular theory, the inventors believe that with over expression of an aspartokinase-encoding gene, a controlled level of conversion of aspartate into aspartyl phosphate (Aspartyl-P), also termed phospho-aspartyl, is obtained that shall contribute to the high level of viability of a recombinant yeast according to the invention. The same applies when at least one aspartokinase coding sequence is under the control of an inducible or repressible promoter.

In some preferred embodiments, the said aspartokinase-encoding gene is the HOM3 gene from *Saccharomyces cerevisiae*, as shown in the examples herein.

In preferred embodiments, the said aspartokinase-encoding gene is placed under the control of the strong promoter pCCW12 or of the inducible or repressible promoter pCUP-1-1.

Illustratively, the aspartokinase gene may be inserted within the HOME gene and/or within the SAM3 gene, as it is shown in the examples herein.

Aspartate Kinase-Encoding Gene Over Expression and/or Controlled Expression

Alternatively or in complement to the over expression and/or controlled expression of an aspartokinase as discussed here-above, a recombinant yeast according to the invention can also be such that it comprises the over expression and/or controlled expression of an aspartate kinase-encoding gene.

Accordingly, in preferred embodiments of a recombinant yeast according to the invention, over expression of an aspartate kinase-encoding gene is obtained by inserting, at selected location(s) of the yeast genome, one or more copies of an expression cassette comprising a aspartate kinase coding sequence. Aspartate kinase and an aspartate kinase-encoding gene that are encompassed by the invention are detailed elsewhere in the present specification.

In some of these embodiments, the said one or more copies of an expression cassette comprising an aspartate kinase-coding sequence comprise regulatory sequences allowing a strong expression of the aspartate kinase, such as a strong promoter that is functional in yeast cells.

In addition to or as an alternative to these embodiments of a recombinant yeast according to the invention, at least one aspartate kinase-encoding gene can be under the control of an inducible or repressible promoter that is functional in yeast cells.

Without wishing to be bound by any particular theory, the inventors believe that with a controlled expression of an aspartate kinase-encoding gene, a controlled level of conversion of aspartate into aspartyl phosphate (Aspartyl-P) is obtained that shall contribute to the high level of viability of a recombinant yeast according to the invention.

In preferred embodiments, the said aspartate kinase-encoding gene is the AK gene from *Bacillus subtilis*, as shown in the examples herein.

In preferred embodiments, the said aspartate kinase-encoding gene is placed under the control of the inducible or repressible promoter pACU7.

Illustratively, the aspartate kinase gene may be inserted within the TRP1 gene, as it is shown in the examples herein.

Aspartate-Semialdehyde Dehydrogenase-Encoding Gene Over Expression and/or Controlled Expression In preferred embodiments of a recombinant yeast according to the invention, over expression of an aspartate-semialdehyde dehydrogenase-encoding gene is obtained by inserting, at selected location(s) of the yeast genome, one or more copies of an expression cassette comprising an aspartate-semialdehyde dehydrogenase coding sequence. Aspartate-semialdehyde dehydrogenase and an aspartate-semialdehyde dehydrogenase-encoding gene that are encompassed by the invention are detailed elsewhere in the present specification.

In some of these embodiments, the said one or more copies of an expression cassette comprising an aspartate-semialdehyde dehydrogenase coding sequence comprise(s) regulatory sequences allowing a strong expression of the aspartate-semialdehyde dehydrogenase, such as a strong promoter that is functional in yeast cells.

In addition to or as an alternative to these embodiments of a recombinant yeast according to the invention, at least one aspartate-semialdehyde dehydrogenase-encoding gene can be under the control of an inducible or repressible promoter that is functional in yeast cells.

Without wishing to be bound by any particular theory, the inventors believe that over expression of an aspartate-semialdehyde dehydrogenase may enhance the conversion of the intermediate metabolite aspartyl phosphate (Aspartyl-P) into aspartyl-semialdehyde. The same applies when at least one aspartate-semialdehyde dehydrogenase coding sequence is under the control of an inducible or repressible promoter.

In some embodiments, the aspartate-semialdehyde dehydrogenase may be an enzyme variant that uses both NADH or NADPH for catalyzing the conversion of aspartyl phosphate (Aspartyl-P) into aspartyl-semialdehyde.

In some preferred embodiments, the said aspartate-semialdehyde dehydrogenase-encoding gene is the HOM2 gene from *Saccharomyces cerevisiae*, or alternatively a variant of HOM2 utilizing both NADH and NADPH as shown in the examples herein and discussed previously.

In preferred embodiments, the said aspartate semi-aldehyde dehydrogenase-encoding gene is placed under the control of the inducible or repressible promoter pACU5 or the strong promoter pCCW12.

Illustratively, the aspartate-semialdehyde dehydrogenase gene may be inserted within the HIS3 gene, and/or within the MUP3 gene, as it is shown in the examples herein.

Diaminobutyrate Aminotransferase-Encoding Gene Over Expression and/or Controlled Expression In preferred embodiments of a recombinant yeast according to the invention, over expression of a diaminobutyrate aminotransferase-encoding gene is obtained by inserting, at selected location(s) of the yeast genome, one or more copies of an expression cassette comprising a diaminobutyrate aminotransferase coding sequence. Diaminobutyrate aminotransferase and a diaminobutyrate aminotransferase-encoding gene that are encompassed by the invention are detailed elsewhere in the present specification.

In some of these embodiments, the said one or more copies of an expression cassette comprising a diaminobutyrate aminotransferase coding sequence comprise(s) regulatory sequences allowing a strong expression of the diaminobutyrate aminotransferase, such as a strong promoter that is functional in yeast cells.

In addition to or as an alternative to these embodiments of a recombinant yeast according to the invention, at least one diaminobutyrate aminotransferase-encoding gene can be under the control of an inducible or repressible promoter that is functional in yeast cells.

Without wishing to be bound by any particular theory, the inventors believe that over expression of an diaminobutyrate aminotransferase may enhance the conversion of the intermediate metabolite aspartyl-semialdehyde into 2,4-diaminobutyrate. The same applies when at least one diaminobutyrate aminotransferase coding sequence is under the control of an inducible or repressible promoter.

In preferred embodiments, the said diaminobutyrate aminotransferase-encoding gene is the EctB gene from *Pseudomonas aeruginosa*, or the EctB gene from *Halomonas elongata* (sometimes also named *Chromohalobacter salexigens*), as shown in the examples herein.

In preferred embodiments, the said diaminobutyrate aminotransferase-encoding gene is placed under the control of the strong promoter pCCW12 and/or the strong promoter pTDH3.

Illustratively, the diaminobutyrate aminotransferase gene may be inserted within the HOME gene and/or within the SAM3 gene and/or within the MUP3 gene and/or within the URA3 gene, as it is shown in the examples herein.

Homoserine-O-Acetyltransferase-Encoding Gene Over Expression and/or Controlled Expression In preferred embodiments of a recombinant yeast according to the invention, over expression of a homoserine-O-acetyltransferase-encoding gene is obtained by inserting, at selected location(s) of the yeast genome, one or more copies of an expression cassette comprising a homoserine-O-acetyltransferase coding sequence. Homoserine-O-acetyltransferase and a homoserine-O-acetyltransferase-encoding gene that are encompassed by the invention are detailed elsewhere in the present specification.

In some of these embodiments, the said one or more copies of an expression cassette comprising a homoserine-O-acetyltransferase coding sequence comprise regulatory sequences allowing a strong expression of the homoserine-O-acetyltransferase, such as a strong promoter that is functional in yeast cells.

In addition to or as an alternative to these embodiments of a recombinant yeast according to the invention, at least one homoserine-O-acetyltransferase-encoding gene can be under the control of an inducible or repressible promoter that is functional in yeast cells.

Without wishing to be bound by any particular theory, the inventors believe that over expression of a homoserine-O-acetyltransferase allows, and consequently increases, the level of conversion of the intermediate metabolite 2,4-diaminobutyrate into acetyl-2,4-diaminobutyrate, in the presence of acetyl-CoA. The same applies when at least one homoserine-O-acetyltransferase coding sequence is under the control of an inducible or repressible promoter.

In preferred embodiments, the said homoserine-O-acetyltransferase-encoding gene is the MET2 gene from *Saccharomyces cerevisiae*, as shown in the examples herein.

In preferred embodiments, the said homoserine-O-acetyltransferase-encoding gene is the METX gene from *Corynebacterium glutamicum*, as shown in the examples herein.

In a particularly preferred embodiment, a recombinant yeast according to the invention comprises at least one homoserine-O-acetyltransferase-encoding gene which is the MET2 gene from *Saccharomyces cerevisiae* and at least one homoserine-O-acetyltransferase-encoding gene which is the METX gene from *Corynebacterium glutamicum*.

In preferred embodiments, the said homoserine-O-acetyltransferase-encoding gene is, independently for each copy of said gene if multiple copies are present, placed under the control of a strong promoter pPDC1 or the inducible or repressible promoter pACU6.

Illustratively, the homoserine-O-acetyltransferase gene may be inserted within the SAM3 gene and/or within the HIS3 gene, as it is shown in the examples herein.

Diaminobutyric Acid Acetyltransferase-Encoding Gene Over Expression and/or Controlled Expression In preferred embodiments of a recombinant yeast according to the invention, over expression of a diaminobutyric acid acetyltransferase-encoding gene is obtained by inserting, at selected location(s) of the yeast genome, one or more copies of an expression cassette comprising a diaminobutyric acid acetyltransferase coding sequence. A diaminobutyric acid acetyltransferase and a diaminobutyric acid acetyltransferase-encoding gene that are encompassed by the invention are detailed elsewhere in the present specification.

In some of these embodiments, the said one or more copies of an expression cassette comprising a diaminobutyric acid acetyltransferase coding sequence comprise(s) regulatory sequences allowing a strong expression of the diaminobutyric acid acetyltransferase, such as a strong promoter that is functional in yeast cells.

In addition to or as an alternative to these embodiments of a recombinant yeast according to the invention, at least one diaminobutyric acid acetyltransferase-encoding gene can be under the control of an inducible or repressible promoter that is functional in yeast cells.

Without wishing to be bound by any particular theory, the inventors believe that over expression of a diaminobutyric acid acetyltransferase allows, and consequently increases, the level of conversion of the intermediate metabolite 2,4-diaminobutyrate into acetyl-2,4-diaminobutyrate, in the presence of acetyl-CoA. The same applies when at least one diaminobutyric acid acetyltransferase coding sequence is under the control of an inducible or repressible promoter.

In preferred embodiments, the said diaminobutyric acid acetyltransferase-encoding gene is the EctA gene from *Halomonas elongata* (sometimes also named *Chromohalobacter salexigens*), as shown in the examples herein.

In preferred embodiments, the said diaminobutyric acid acetyltransferase-encoding gene is placed under the control of the strong promoter pPDC1.

Illustratively, the diaminobutyric acid acetyltransferase gene may be inserted within the LYP1 gene and/or within the MUP3 gene, as it is shown in the examples herein.

In a particular embodiment, a recombinant yeast according to the invention is such that its genome comprises:
- at least one nucleic acid encoding an homoserine-O-acetyltransferase METX over expressed and/or under the control of an inducible or repressible promoter, and preferably under the control of an inducible or repressible promoter; and
- at least one nucleic acid encoding a diaminobutyric acid acetyltransferase EctA over expressed and/or under the control of an inducible or repressible promoter, and preferably under the control of an inducible or repressible promoter.

Ectoine Synthase-Encoding Gene Over Expression and/or Controlled Expression

In preferred embodiments of a recombinant yeast according to the invention, over expression of an ectoine synthase-encoding gene is obtained by inserting, at selected location(s) of the yeast genome, one or more copies of an expression cassette comprising an ectoine synthase coding sequence. An ectoine synthase and an ectoine synthase-encoding gene that are encompassed by the invention are detailed elsewhere in the present specification.

In some of these embodiments, the said one or more copies of an expression cassette comprising an ectoine synthase coding sequence comprise(s) regulatory sequences allowing a strong expression of the ectoine synthase, such as a strong promoter that is functional in yeast cells.

In addition to or as an alternative to these embodiments of a recombinant yeast according to the invention, at least one ectoine synthase-encoding gene can be under the control of an inducible or repressible promoter that is functional in yeast cells.

Without wishing to be bound by any particular theory, the inventors believe that over expression of an ectoine synthase allows, and consequently increases, the level of conversion of the intermediate metabolite acetyl-2,4-diaminobutyrate into ectoine. The same applies when at least one ectoine synthase coding sequence is under the control of an inducible or repressible promoter.

In preferred embodiments, the said ectoine synthase-encoding gene is the EctC gene from *Halomonas elongata*, as shown in the examples herein.

In preferred embodiments, the said ectoine synthase-encoding gene is placed under the control of the strong promoter pTDH3 and/or the strong promoter pTEF1.

Illustratively, the ectoine synthase gene may be inserted within the LYP1 gene and/or within the MUP3 gene and/or within the URA3 gene, as it is shown in the examples herein.

Deletion or Under Expression of Homoserine Dehydrogenase

A recombinant yeast according to the invention is further defined as having a genome in which:
(i) at least one, preferably all, endogenous nucleic acid encoding an homoserine dehydrogenase HOM6 has been deleted and/or interrupted, and/or
(ii) at least one, preferably all, nucleic acid encoding an homoserine dehydrogenase HOM6 is independently:
under the control of an inducible or repressible promoter;
under the control of a weak promoter; and/or
in a destabilized form.

Without wishing to be bound by any particular theory, the inventors believe that an under expression of an homoserine dehydrogenase gene shall increase 2,4-diaminobutyrate production by the recombinant yeast by reducing the consumption of the produced aspartyl-semialdehyde by its conversion into homoserine.

In some embodiments, under expression of an homoserine dehydrogenase may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Homoserine dehydrogenase under expression also encompasses the insertion of a nucleic acid encoding a destabilized homoserine dehydrogenase. A destabilized homoserine dehydrogenase is a variant of homoserine dehydrogenase that is more rapidly degraded within the yeast cell than the parent homoserine dehydrogenase.

In preferred embodiments, a destabilized homoserine dehydrogenase consists of a degron-tagged homoserine dehydrogenase protein.

For example, the homoserine dehydrogenase gene can be interrupted by loxP, or for example by URA3.K1-loxP, and is thus deleted (which can also be termed inactivated).

It can alternatively be interrupted by a cassette comprising genes of interest, as illustrated in the examples as filed.

Aspartokinase (Hom3)

The aspartokinase enzyme is a protein which is described in the art for catalyzing the conversion of L-aspartate in the presence of ATP into 4-phospho-L-aspartate. The aspartokinase encoded by the genome of *Saccharomyces cerevisiae* may be termed HOM3.

A method implemented to measure the activity level of aspartokinase belongs to the general knowledge of the one skilled in the art.

In this regard, the one skilled in the art may advantageously refer to the method described by Stadtman et al. (1961, J Biol Chem, Vol. 236 (7): 2033-2038).

Preferred aspartokinase in the present specification is an enzyme having an EC number of n° EC 2.7.2.4.

According to a preferred embodiment, the nucleic acid(s) encoding an aspartokinase may be nucleic acid(s) originating from organisms preferably selected in a group comprising prokaryotic organisms and eukaryotic organisms. In some embodiments, the nucleic acid(s) encoding an aspartokinase may be nucleic acid(s) originating from archaebacteria. In some embodiments, the nucleic acid(s) encoding an aspartokinase may be nucleic acid(s) originating from organisms preferably selected from *Bacillus subtilis*, and yeasts. In some other preferred embodiments, the nucleic acid(s) encoding an aspartokinase may be nucleic acid(s) originating from a yeast, and especially from *Saccharomyces cerevisiae*.

According to a yet preferred embodiment, the nucleic acid(s) encoding an aspartokinase may be nucleic acid(s) selected from the group consisting of sequences having at least 25%, advantageously at least 65%, preferably at least 80%, nucleic acid identity with a nucleic acid of SEQ ID NO: 1, and also a biological activity of the same nature. The nucleic acid of SEQ ID NO: 1 encodes an aspartokinase originating from *Saccharomyces cerevisiae*, that may also be termed HOM3.

A biological activity of the same nature regarding this sequence is the capacity to code for an enzyme that catalyzes the conversion of L-aspartate in the presence of ATP into 4-phospho-L-aspartate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the aspartokinase from *Saccharomyces cerevisiae*, the one skilled in the art may refer to the accession number NP010972 in the UniProt database, or to SEQ ID NO. 2 described herein.

According to another particular embodiment, the nucleic acid(s) encoding aspartokinase may be nucleic acid(s) encoding an amino acid sequence selected from the group consisting of sequences having at least 25%, advantageously at least 65%, preferably at least 80%, amino acid identity with the amino acid sequence of SEQ ID NO: 2, and also a biological activity of the same nature. Illustratively, the aspartokinase originating from *Aquamarina atlantica* has 25% amino acid identity with the aspartokinase of SEQ ID NO. 2.

A biological activity of the same nature regarding this sequence is as described previously, i.e. the capacity to catalyze the conversion of L-aspartate in the presence of ATP into 4-phospho-L-aspartate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the aspartokinase in the present invention is regulated by at least one promoter and at least one terminator, such as herein after defined more in details, which are present in 5' and 3' position respectively of the nucleic acid sequence encoding the said aspartokinase.

As it is specified elsewhere in the present description, the aspartokinase is overexpressed and/or under the control of an inducible or repressible promoter in a recombinant yeast according to the invention.

In some embodiments, overexpression of the aspartokinase may result from the control of the corresponding gene by a strong promoter within the said recombinant yeast.

In some other embodiments, overexpression of the aspartokinase may result from the presence of a plurality of copies of an aspartokinase-encoding sequence within the genome of the said recombinant yeast.

In still further embodiments, overexpression of aspartokinase may result from both (i) the control of the corresponding gene by a strong promoter within the said recombinant yeast and (ii) the presence of a plurality of copies of an aspartokinase-encoding sequence within the genome the said recombinant yeast.

Aspartate Kinase (AK)

The aspartate kinase enzyme is a protein which is described in the art for catalyzing the conversion of L-aspartate in the presence of ATP into 4-phospho-L-aspartate. The aspartate kinase encoded by the genome of *Bacillus subtilis* may be termed AK.

A method implemented to measure the activity level of aspartate kinase belongs to the general knowledge of the one skilled in the art and is the same as the one indicated previously for aspartokinase.

According to a preferred embodiment, the nucleic acid(s) encoding an aspartate kinase may be nucleic acid(s) originating from organisms preferably selected in a group comprising prokaryotic organisms and eukaryotic organisms. In some embodiments, the nucleic acid(s) encoding an aspartate kinase may be nucleic acid(s) originating from archaebacteria. In some embodiments, the nucleic acid(s) encoding an aspartate kinase may be nucleic acid(s) originating from organisms preferably selected from *Bacillus subtilis*, and yeasts. In some other preferred embodiments, the nucleic acid(s) encoding an aspartate kinase may be nucleic acid(s) originating from yeast, and especially from *Saccharomyces cerevisiae*.

For the nucleic acid sequence, it may be referred to the one disclosed in the access number NC_000964.3 in the NCBI database.

According to a yet preferred embodiment, the nucleic acid(s) encoding an aspartate kinase may be nucleic acid(s) selected from the group consisting of sequences having at least 25%, advantageously at least 65%, preferably at least 80%, nucleic acid identity with a nucleic acid of SEQ ID NO. 3, and also a biological activity of the same nature. The nucleic acid of SEQ ID NO. 3 encodes an aspartate kinase originating from *Bacillus subtilis*, that may also be termed AK.

A biological activity of the same nature regarding this sequence is the capacity to code for an enzyme that catalyzes the conversion of L-aspartate in the presence of ATP into 4-phospho-L-aspartate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the aspartate kinase from *Bacillus* substilis, the one skilled in the art may refer to the accession number NP_389558.2 in the UniProt database, or to SEQ ID NO. 4 described herein.

According to another particular embodiment, the nucleic acid(s) encoding aspartate kinase may be nucleic acid(s) encoding an amino acid sequence selected from the group consisting of sequences having at least 25%, advantageously at least 65%, preferably at least 80%, amino acid identity with the amino acid sequence of SEQ ID NO. 4, and also a biological activity of the same nature. Illustratively, the aspartate kinase originating from *Aquamarina atlantica* has 25% amino acid identity with the aspartokinase of SEQ ID NO. 4.

A biological activity of the same nature regarding this sequence is as described previously, i.e. the capacity to catalyze the conversion of L-aspartate in the presence of ATP into 4-phospho-L-aspartate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the aspartate kinase in the present invention is regulated by at least one promoter and at least one terminator, such as herein after defined more in details, which are present in 5' and 3' position respectively of the nucleic acid sequence encoding the said aspartate kinase.

As it is specified elsewhere in the present description, the aspartate kinase is overexpressed and/or under the control of an inducible or repressible promoter in a recombinant yeast according to the invention.

In some embodiments, overexpression of the aspartate kinase may result from the control of the corresponding gene by a strong promoter within the said recombinant yeast.

In some other embodiments, overexpression of the aspartate kinase may result from the presence of a plurality of copies of an aspartate kinase-encoding sequence within the genome of the said recombinant yeast.

In still further embodiments, overexpression of aspartate kinase may result from both (i) the control of the corresponding gene by a strong promoter within the said recombinant yeast and (ii) the presence of a plurality of copies of an aspartate kinase-encoding sequence within the genome the said recombinant yeast.

Aspartate-Semialdehyde Dehydrogenase (HOM2)

The aspartate-semialdehyde dehydrogenase is a protein which is known in the art to catalyze the NADPH-dependent formation of L-aspartate-semialdehyde by the reductive dephosphorylation of L-aspartyl-4-phosphate. The aspartate-semialdehyde dehydrogenase encoded by the genome of *Saccharomyces cerevisiae* may be termed HOM2.

A method implemented to measure the activity level of aspartate-semialdehyde dehydrogenase belongs to the general knowledge of the one skilled in the art.

Preferred aspartate-semialdehyde dehydrogenase in the present specification is an enzyme having an EC number 1.2.1.11.

According to a preferred embodiment, the nucleic acid(s) encoding an aspartate-semialdehyde dehydrogenase may be nucleic acid(s) originating from organisms preferably selected in a group comprising prokaryotic organisms and eukaryotic organisms. In some embodiments, the nucleic acid(s) encoding an aspartate-semialdehyde dehydrogenase may be nucleic acid(s) originating from archaebacteria. In some preferred embodiments, the nucleic acid(s) encoding an aspartate-semialdehyde dehydrogenase may be nucleic acid(s) originating from yeast, and especially from *Saccharomyces cerevisiae*.

According to other preferred embodiment, the nucleic acid encoding an aspartate-semialdehyde dehydrogenase may be a variant or a mutant of the aspartate-semialdehyde dehydrogenase from *Saccharomyces cerevisiae*, wherein the said variant enzyme or the said mutant enzyme uses both NADH or NADPH for catalyzing reactions. Such variant or mutant enzymes are known in the art and are previously discussed in the present text.

According to a yet preferred embodiment, the nucleic acid(s) encoding an aspartate-semialdehyde dehydrogenase may be nucleic acid(s) selected from the group consisting of sequences having at least 27%, advantageously at least 65%, preferably at least 80%, nucleic acid identity with a nucleic acid selected in a group consisting of the reference nucleic acid sequences of SEQ ID NO: 5 and SEQ ID NO. 6, and also a biological activity of the same nature. The nucleic acids of SEQ ID NO: 5 and SEQ ID NO. 6 encode an aspartate-semialdehyde dehydrogenase originating from *Saccharomyces cerevisiae*, that may also be collectively termed HOM2 herein.

A biological activity of the same nature regarding this sequence is the capacity to code for an enzyme that catalyzes the NADPH-dependent formation of L-aspartate-semialdehyde by the reductive dephosphorylation of L-aspartyl-4-phosphate.

As described herein, a nucleic acid sequence having at least 27% nucleotide identity with a reference nucleic acid sequence encompasses nucleic acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the aspartate-semialdehyde dehydrogenase from *Saccharomyces cerevisiae*, the one skilled in the art may refer to the accession number NP010442 in the UniProt database, or to SEQ ID NO. 7 described herein.

According to another particular embodiment, the nucleic acid(s) encoding an aspartate-semialdehyde dehydrogenase may be nucleic acid(s) encoding an amino acid sequence selected from the group consisting of sequences having at least 27%, advantageously at least 65%, preferably at least 80%, amino acid identity with the amino acid sequence of SEQ ID NO: 7, and also a biological activity of the same nature. Illustratively, the aspartate-semialdehyde dehydrogenase originating from *Lactobacillus wasatchensis* has 27% amino acid identity with the aspartate-semialdehyde dehydrogenase of SEQ ID NO. 7.

A biological activity of the same nature regarding this sequence is as described previously, i.e. the capacity to catalyze the NADPH-dependent formation of L-aspartate-semialdehyde by the reductive dephosphorylation of L-aspartyl-4-phosphate.

As described herein, an amino acid sequence having at least 27% amino acid identity with a reference nucleic acid sequence encompasses amino acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the aspartate-semialdehyde dehydrogenase in the present invention is regulated by at least one promoter and at least one terminator, such as herein after defined more in details, which are present in 5' and 3' position respectively of the nucleic acid sequence encoding the said aspartate-semialdehyde dehydrogenase.

As it is specified elsewhere in the present description, the aspartate-semialdehyde dehydrogenase is overexpressed and/or under the control of an inducible or repressible promoter in a recombinant yeast according to the invention.

In some embodiments, overexpression of the aspartate-semialdehyde dehydrogenase may result from the control of the corresponding gene by a strong promoter within the said recombinant yeast.

In some other embodiments, overexpression of the aspartate-semialdehyde dehydrogenase may result from the presence of a plurality of copies of a aspartate-semialdehyde dehydrogenase-encoding sequence within the genome of the said recombinant yeast.

In still further embodiments, overexpression of the aspartate-semialdehyde dehydrogenase may result from both (i) the control of the corresponding gene by a strong promoter within the said recombinant yeast and (ii) the presence of a plurality of copies of an aspartate-semialdehyde dehydrogenase-encoding sequence within the genome the said recombinant yeast.

Diaminobutyrate Aminotransferase (EctB)

The diaminobutyrate aminotransferase enzyme is a protein which is described in the art for catalyzing the conversion of aspartyl semialdehyde in the presence of glutamate into 2,4-diaminobutyrate. The diaminobutyrate aminotransferase encoded by the genome of *Halomonas elongata* may be termed EctB or EctB.He.

A method implemented to measure the activity level of diaminobutyrate aminotransferase belongs to the general knowledge of the one skilled in the art.

In this regard, the one skilled in the art may advantageously refer to the method described by Ono H et al., 1999, Journal of Bacteriology, p 91-99.

Preferred diaminobutyrate aminotransferase in the present specification is an enzyme having an EC number of n° 2.6.1.76.

According to a preferred embodiment, the nucleic acid(s) encoding an diaminobutyrate aminotransferase may be nucleic acid(s) originating from organisms preferably selected in a group comprising prokaryotic organisms and eukaryotic organisms. In some embodiments, the nucleic acid(s) encoding a diaminobutyrate aminotransferase may be nucleic acid(s) originating from archaebacteria. In some embodiments, the nucleic acid(s) encoding a diaminobutyrate aminotransferase may be nucleic acid(s) originating from organisms preferably selected from bacteria, and especially from *Pseudomonas aeruginosa, Halomonas elongata* or *Sporocarcina newyorkensisn*, and preferably from *Pseudomonas aeruginosa* or *Halomonas elongata*.

According to a yet preferred embodiment, the nucleic acid(s) encoding a diaminobutyrate aminotransferase may be nucleic acid(s) selected from the group consisting of sequences having at least 35%, advantageously at least 65%, preferably at least 80%, nucleic acid identity with a nucleic acid of SEQ ID NO. 8 or SEQ ID NO. 9, and also a biological activity of the same nature.

A biological activity of the same nature regarding this sequence is the capacity to code for an enzyme that catalyzes the conversion of aspartyl semialdehyde in the presence of glutamate into 2,4-diaminobutyrate.

As described herein, a nucleic acid sequence having at least 35% nucleotide identity with a reference nucleic acid sequence encompasses nucleic acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the diaminobutyrate aminotransferase from *Halomonas elongata*, the one skilled in the art may refer to the accession number WP_013332345.1 in the UniProt database, or to SEQ ID NO. 10 or SEQ ID NO. 11 described herein.

According to another particular embodiment, the nucleic acid(s) encoding diaminobutyrate aminotransferase may be nucleic acid(s) encoding an amino acid sequence selected from the group consisting of sequences having at least 35%, advantageously at least 65%, preferably at least 80%, amino acid identity with the amino acid sequence of SEQ ID NO. 10 or SEQ ID NO. 11, and also a biological activity of the same nature.

A biological activity of the same nature regarding this sequence is as described previously, i.e. the capacity to catalyze the conversion of aspartyl semialdehyde in the presence of glutamate into 2,4-diaminobutyrate.

As described herein, an amino acid sequence having at least 35% amino acid identity with a reference nucleic acid sequence encompasses amino acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the diaminobutyrate aminotransferase in the present invention is regulated by at least one promoter and at least one terminator, such as herein after defined more in details, which are present in 5' and 3' position respectively of the nucleic acid sequence encoding the said diaminobutyrate aminotransferase.

As it is specified elsewhere in the present description, the diaminobutyrate aminotransferase is overexpressed and/or under the control of an inducible or repressible promoter in a recombinant yeast according to the invention.

In some embodiments, overexpression of the diaminobutyrate aminotransferase may result from the control of the corresponding gene by a strong promoter within the said recombinant yeast.

In some other embodiments, overexpression of the diaminobutyrate aminotransferase may result from the presence of a plurality of copies of a diaminobutyrate aminotransferase-encoding sequence within the genome of the said recombinant yeast.

In still further embodiments, overexpression of diaminobutyrate aminotransferase may result from both (i) the control of the corresponding gene by a strong promoter within the said recombinant yeast and (ii) the presence of a plurality of copies of a diaminobutyrate aminotransferase-encoding sequence within the genome of the said recombinant yeast.

Homoserine O-Acetyltransferase (MET2; METX)

The homoserine O-acetyl transferase enzyme is a protein which is described in the art for catalyzing the reaction between Acetyl-CoA and 2,4-diaminobutyrate into CoA and Acetyl-2,4-diaminobutyrate. The homoserine O-acetyl transferase encoded by the genome of *Saccharomyces cerevisiae* may be termed MET2.

A method implemented to measure the activity level of homoserine O-acetyltransferase belongs to the general knowledge of the one skilled in the art.

In this regard, the one skilled in the art may advantageously refer to the method described by Shuzo Yamagata (1987, The Journal of Bacteriology, Vol. 169(8): 3458-3463.

Preferred homoserine O-acetyltransferase in the present specification is an enzyme having an EC number of n° EC 2.3.1.31.

According to a preferred embodiment, the nucleic acid(s) encoding a homoserine O-acetyltransferase may be nucleic acid(s) originating from organisms preferably selected in a group comprising prokaryotic organisms and eukaryotic organisms. In some embodiments, the nucleic acid(s) encoding a homoserine O-acetyltransferase may be nucleic acid(s) originating from archaebacteria. In some embodiments, the nucleic acid(s) encoding a homoserine O-acetyltransferase may be nucleic acid(s) originating from organisms preferably selected from *Corynebacterium glutamicum*, and yeasts. In some other preferred embodiments, the nucleic acid(s) encoding a homoserine O-acetyltransferase may be nucleic acid(s) originating from yeast, and especially from *Saccharomyces cerevisiae*.

According to a particular embodiment, the nucleic acid encoding an homoserine-O-acetyltransferase METX are nucleic acid from a bacterium, in particular from a bacterium selected, independently, from the group consisting of *Corynebacterium glutamicum, Escherichia coli, Haemophilius influenza, Streptomyces lavendulae, Leptospira interrogans, Streptococcus pneumonia* and *Mycobacterium tuberculosis*.

According to a yet preferred embodiment, the nucleic acid(s) encoding a homoserine O-acetyltransferase may be nucleic acid(s) selected from the group consisting of sequences having at least 27%, advantageously at least 65%, preferably at least 80%, nucleic acid identity with a nucleic acid of SEQ ID NO: 12, and also a biological activity of the same nature. The nucleic acid of SEQ ID NO: 12 encodes a homoserine O-acetyltransferase originating from *Saccharomyces cerevisiae*, that may also be termed MET2. The homoserine O-acetyltransferase originating from *Corynebacterium glutamicum* is usually termed METX.

A biological activity of the same nature regarding this sequence is the capacity to code for an enzyme that catalyzes the reaction between Acetyl-CoA and 2,4-diaminobutyrate into CoA and Acetyl-2,4-diaminobutyrate.

As described herein, a nucleic acid sequence having at least 27% nucleotide identity with a reference nucleic acid sequence encompasses nucleic acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the the homoserine O-acetyltransferase from *Saccharomyces cerevisiae*, the one skilled in the art may refer to the accession number NP014122 in the UniProt database, or to SEQ ID NO. 13 described herein.

According to another particular embodiment, the nucleic acid(s) encoding a homoserine O-acetyltransferase may be nucleic acid(s) encoding an amino acid sequence selected from the group consisting of sequences having at least 27%, advantageously at least 65%, preferably at least 80%, amino acid identity with the amino acid sequence of SEQ ID NO: 13, and also a biological activity of the same nature. Illustratively, the homoserine O-acetyltransferase originating from *Aquamarina atlantica* has 27% amino acid identity with the homoserine O-acetyltransferase of SEQ ID NO. 13.

A biological activity of the same nature regarding this sequence is as described previously, i.e. the capacity to catalyze the reaction between Acetyl-CoA and 2,4-diaminobutyrate into CoA and Acetyl-2,4-diaminobutyrate.

As described herein, an amino acid sequence having at least 27% amino acid identity with a reference nucleic acid sequence encompasses amino acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of a homoserine O-acetyltransferase in the present invention is regulated by at least one promoter and at least one terminator, such as herein after defined more in details, which are present in 5' and 3' position respectively of the nucleic acid sequence encoding the said homoserine O-acetyltransferase.

As it is specified elsewhere in the present description, in some embodiments of the invention, the homoserine O-acetyltransferase is overexpressed and/or under the control of an inducible or repressible promoter in a recombinant yeast according to the invention.

In some embodiments, overexpression of the homoserine O-acetyltransferase may result from the control of the corresponding gene by a strong promoter within the said recombinant yeast.

In some other embodiments, overexpression of the homoserine O-acetyltransferase may result from the presence of a plurality of copies of a homoserine O-acetyltransferase-encoding sequence within the genome the said recombinant yeast.

In still further embodiments, overexpression of the homoserine O-acetyltransferase may result from both (i) the control of the corresponding gene by a strong promoter within the said recombinant yeast and (ii) the presence of a plurality of copies of a homoserine O-acetyltransferase-encoding sequence within the genome the said recombinant yeast.

Diaminobutyric Acid Acetyltransferase (EctA)

The diaminobutyric acid acetyltransferase enzyme is a protein which is described in the art for catalyzing the conversion of 2,4-diaminobutyrate in the presence of Acetyl-CoA into acetyl-2,4-diaminobutyrate. The diaminobutyric acid acetyltransferase encoded by the genome of *Halomonas elongata* may be termed EctA or EctA.He.

A method implemented to measure the activity level of diaminobutyric acid acetyltransferase belongs to the general knowledge of the one skilled in the art.

In this regard, the one skilled in the art may advantageously refer to the method described by Ono H et al., 1999, Journal of Bacteriology, p 91-99.

Preferred diaminobutyric acid acetyltransferase in the present specification is an enzyme having an EC number of n° 2.3.1.178.

According to a preferred embodiment, the nucleic acid(s) encoding a diaminobutyric acid acetyltransferase may be nucleic acid(s) originating from organisms preferably selected in a group comprising prokaryotic organisms and eukaryotic organisms. In some embodiments, the nucleic acid(s) encoding a diaminobutyric acid acetyltransferase may be nucleic acid(s) originating from archaebacteria. In some embodiments, the nucleic acid(s) encoding a diaminobutyric acid acetyltransferase may be nucleic acid(s) originating from organisms preferably selected from bacteria, and especially from *Chromohalobacter salexigens, Pseudomonas aeruginosa, Thaurea* sp.28, or *Halomonas elongata*.

According to a yet preferred embodiment, the nucleic acid(s) encoding a diaminobutyric acid acetyltransferase may be nucleic acid(s) selected from the group consisting of sequences having at least 30%, advantageously at least 65%, preferably at least 80%, nucleic acid identity with a nucleic acid of SEQ ID NO. 14, and also a biological activity of the same nature.

A biological activity of the same nature regarding this sequence is the capacity to code for an enzyme that catalyzes the conversion of 2,4-diaminobutyrate in the presence of Acetyl-CoA into acetyl-2,4-diaminobutyrate.

As described herein, a nucleic acid sequence having at least 30% nucleotide identity with a reference nucleic acid sequence encompasses nucleic acid sequences having at least 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the diaminobutyric acid acetyltransferase from *Halomonas elongata*, the one skilled in the art may refer to the accession number WP_035409657.1 in the UniProt database, or to SEQ ID NO. 15 described herein.

According to another particular embodiment, the nucleic acid(s) encoding diaminobutyric acid acetyltransferase may be nucleic acid(s) encoding an amino acid sequence selected from the group consisting of sequences having at least 30%, advantageously at least 65%, preferably at least 80%, amino acid identity with the amino acid sequence of SEQ ID NO. 15, and also a biological activity of the same nature.

A biological activity of the same nature regarding this sequence is as described previously, i.e. the capacity to catalyze the conversion of 2,4-diaminobutyrate in the presence of Acetyl-CoA into acetyl-2,4-diaminobutyrate.

As described herein, an amino acid sequence having at least 30% amino acid identity with a reference nucleic acid sequence encompasses amino acid sequences having at least 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the diaminobutyric acid acetyltransferase in the present invention is regulated by at least one promoter and at least one terminator, such as herein after defined more in details, which are present in 5' and 3' position respectively of the nucleic acid sequence encoding the said diaminobutyric acid acetyltransferase.

As it is specified elsewhere in the present description, the diaminobutyric acid acetyltransferase is overexpressed and/or under the control of an inducible or repressible promoter in a recombinant yeast according to the invention.

In some embodiments, overexpression of the diaminobutyric acid acetyltransferase may result from the control of the corresponding gene by a strong promoter within the said recombinant yeast.

In some other embodiments, overexpression of the diaminobutyric acid acetyltransferase may result from the presence of a plurality of copies of a diaminobutyric acid acetyltransferase-encoding sequence within the genome of the said recombinant yeast.

In still further embodiments, overexpression of diaminobutyric acid acetyltransferase may result from both (i) the control of the corresponding gene by a strong promoter within the said recombinant yeast and (ii) the presence of a plurality of copies of a diaminobutyric acid acetyltransferase-encoding sequence within the genome the said recombinant yeast.

Ectoine Synthase (EctC)

The ectoine synthase enzyme is a protein which is described in the art for catalyzing the conversion of acetyl-2,4-diaminobutyrate into ectoine. The ectoine synthase encoded by the genome of *Halomonas elongata* may be termed EctC or EctC.He.

A method implemented to measure the activity level of ectoine synthase belongs to the general knowledge of the one skilled in the art.

In this regard, the one skilled in the art may advantageously refer to the method described by Ono H et al., 1999, Journal of Bacteriology, p 91-99.

Preferred ectoine synthase in the present specification is an enzyme having an EC number of n° 4.2.1.108.

According to a preferred embodiment, the nucleic acid(s) encoding an ectoine synthase may be nucleic acid(s) originating from organisms preferably selected in a group comprising prokaryotic organisms and eukaryotic organisms. In some embodiments, the nucleic acid(s) encoding an ectoine synthase may be nucleic acid(s) originating from archaebacteria. In some embodiments, the nucleic acid(s) encoding an ectoine synthase may be nucleic acid(s) originating from organisms preferably selected from bacteria, and especially from *Pseudomonas aeruginosa, Halomonas elongata* or *Micrococcus luteus*.

According to a yet preferred embodiment, the nucleic acid(s) encoding an ectoine synthase may be nucleic acid(s) selected from the group consisting of sequences having at least 35%, advantageously at least 65%, preferably at least 80%, nucleic acid identity with a nucleic acid of SEQ ID NO. 16, and also a biological activity of the same nature.

A biological activity of the same nature regarding this sequence is the capacity to code for an enzyme that catalyzes the conversion of acetyl-2,4-diaminobutyrate into ectoine.

As described herein, a nucleic acid sequence having at least 35% nucleotide identity with a reference nucleic acid sequence encompasses nucleic acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the ectoine synthase from *Halomonas elongata*, the one skilled in the art may refer to the accession number WP_013332346 in the UniProt database, or to SEQ ID NO. 17 described herein.

According to another particular embodiment, the nucleic acid(s) encoding ectoine synthase may be nucleic acid(s) encoding an amino acid sequence selected from the group consisting of sequences having at least 35%, advantageously at least 65%, preferably at least 80%, amino acid identity with the amino acid sequence of SEQ ID NO. 17, and also a biological activity of the same nature.

A biological activity of the same nature regarding this sequence is as described previously, i.e. the capacity to catalyze the conversion of acetyl-2,4-diaminobutyrate into ectoine.

As described herein, an amino acid sequence having at least 35% amino acid identity with a reference nucleic acid sequence encompasses amino acid sequences having at least 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the ectoine synthase in the present invention is regulated by at least one promoter and at least one terminator, such as herein after defined more in details, which are present in 5' and 3' position respectively of the nucleic acid sequence encoding the said ectoine synthase.

As it is specified elsewhere in the present description, the ectoine synthase is overexpressed and/or under the control of an inducible or repressible promoter in a recombinant yeast according to the invention.

In some embodiments, overexpression of the ectoine synthase may result from the control of the corresponding gene by a strong promoter within the said recombinant yeast.

In some other embodiments, overexpression of the ectoine synthase may result from the presence of a plurality of copies of an ectoine synthase-encoding sequence within the genome of the said recombinant yeast.

In still further embodiments, overexpression of ectoine synthase may result from both (i) the control of the corresponding gene by a strong promoter within the said recombinant yeast and (ii) the presence of a plurality of copies of an ectoine synthase-encoding sequence within the genome the said recombinant yeast.

Homoserine Dehydrogenase (HOM6)

The homoserine dehydrogenase enzyme is a protein which is described in the art for catalyzing the conversion of L-homoserine into L-aspartate 4-semialdehyde, in the presence of NAD or NADP. The homoserine dehydrogenase encoded by the genome of *Saccharomyces cerevisiae* may be termed HOM6.

A method implemented to measure the activity level of homoserine dehydrogenase belongs to the general knowledge of the one skilled in the art.

In this regard, the one skilled in the art may advantageously refer to the method described by Calnyanto et al. (2006, Microbiology, Vol. 152: 105-112).

Preferred homoserine dehydrogenase in the present specification is an enzyme having an EC number of n° 1.1.1.3.

According to a preferred embodiment, the nucleic acid(s) encoding a homoserine dehydrogenase may be nucleic acid(s) originating from organisms preferably selected in a group comprising prokaryotic organisms and eukaryotic organisms. In some preferred embodiments, the nucleic acid(s) encoding a homoserine dehydrogenase may be nucleic acid(s) originating from a yeast, and especially from *Saccharomyces cerevisiae*.

According to a particular embodiment, the nucleic acid(s) encoding a homoserine dehydrogenase may be nucleic acid of SEQ ID NO: 18. The nucleic acid of SEQ ID NO: 18 encodes a homoserine dehydrogenase originating from *Saccharomyces*, that may also be termed HOM6.

For the amino acid sequence of the homoserine dehydrogenase from *Saccharomyces cerevisiae*, the one skilled in the art may refer to the accession number AJR75529 or NP012673 in the UniProt database, or to SEQ ID NO. 19 described herein.

As above-mentioned, the expression level of the homoserine dehydrogenase in the present invention is regulated by at least one promoter and at least one terminator, such as herein after defined more in details, which are present in 5' and 3' position respectively of the nucleic acid sequence encoding the said homoserine dehydrogenase.

As it is specified elsewhere in the present description, in some embodiments of the invention, the homoserine dehydrogenase is (a) fully or partially deleted or interrupted, or (b) under the control of an inducible or repressible promoter; under the control of a weak promoter; and/or in a destabilized form, in a recombinant yeast according to the invention.

Specific Embodiments of an Ectoine-Producing Recombinant Yeast

Aspartate Transaminase Over Expression and/or Controlled Expression

In preferred embodiments of a recombinant yeast according to the invention, at least one nucleic acid encoding an aspartate transaminase is overexpressed and/or is under the control of an inducible or repressible promoter.

The aspartate transaminase enzyme (also known as aspartate aminotransferase) is a protein which is described in the art for catalyzing the reaction of L-aspartate and 2-oxoglutarate for producing oxaloacetate and L-glutamate. The aspartate transaminase enzyme encoded by the genome *Saccharomyces cerevisiae* may be termed AAT2.

According to these embodiments, over expression of an aspartate transaminase-encoding gene is obtained by inserting, at selected location(s) of the yeast genome, one or more copies of an expression cassette comprising an aspartate transaminase coding sequence. Aspartate transaminase and aspartate-transaminase-encoding gene that are encompassed by the invention are detailed elsewhere in the present specification.

In some of these embodiments, the said one or more copies of an expression cassette comprising an aspartate transaminase coding sequence comprise regulatory sequences allowing a strong expression of the aspartate transaminase, such as a strong promoter that is functional in yeast cells.

In addition to or as an alternative to these embodiments of a recombinant yeast according to the invention, at least one aspartate transaminase-encoding gene can be under the control of an inducible or repressible promoter that is functional in yeast cells.

Without wishing to be bound by any particular theory, the inventors believe that an over expression of an aspartate transaminase may induce a high level of conversion of oxaloacetate into aspartate. The same applies when at least one aspartate transaminase coding sequence is under the control of an inducible or repressible promoter.

A method implemented to measure the activity level of an aspartate transaminase belongs to the general knowledge of the one skilled in the art.

In this regard, the one skilled in the art may advantageously refer to the method described in Yagi et al. (1982, Biochem, VOl. 92: 35-43).

In some embodiments, the said aspartate transaminase-encoding gene is the AAT2 gene from *Saccharomyces cerevisiae*, as shown in the examples herein.

In preferred embodiments, the aspartate aminotransferase is encoded by the *A. Thaliana* AAT2-gene.

In preferred embodiments, the said aspartate transaminase-encoding gene is placed under the control of the inducible or repressible promoter pACU1 or of the strong promoter pADH1 or of the strong promoter pPGK1.

Illustratively, the AAT2 gene may be inserted within the CAN1 gene and/or within the GNP1 gene and/or within the MUP3 gene, as it is shown in the examples herein.

Preferred aspartate transaminase in the present specification is known by the EC number 2.6.1.1.

The nucleic acid(s) encoding an aspartate transaminase may be nucleic acid(s) originating from organisms preferably selected in a group comprising prokaryotic organisms and eukaryotic organisms. In some embodiments, the nucleic acid(s) encoding an aspartate transaminase may be nucleic acid(s) originating from archaebacteria. In some preferred embodiments, the nucleic acid(s) encoding an aspartate transaminase may be nucleic acid(s) originate(s) from a yeast organism, and most preferably *Saccharomyces cerevisiae*.

According to a yet preferred embodiment, the nucleic acid(s) encoding an aspartate transaminase or AAT2 may be nucleic acid(s) selected from the group consisting of sequences having at least 39%, advantageously at least 65%, and preferably at least 80%, nucleic acid identity with the nucleic acid sequences of SEQ ID NO: 20, and also a biological activity of the same nature.

A biological activity of the same nature regarding this sequence is the capacity to code for an enzyme that catalyzes the reaction of L-aspartate and 2-oxoglutarate for producing oxaloacetate and L-glutamate.

As described herein, a nucleic acid sequence having at least 39% nucleotide identity with a reference nucleic acid sequence encompasses nucleic acid sequences having at least 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 20, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 20, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 20, and also a biological activity of the same nature.

For the amino acid sequence of the aspartate transaminase AAT2 from *Saccharomyces cerevisiae*, the one skilled in the art may refer to the accession number NP013127 in the UniProt database, or to SEQ ID NO. 21 described herein. Illustratively, the aspartate transaminase originating from *E. coli* has 39% amino acid identity with the aspartate transaminase AAT2 of SEQ ID NO. 21.

According to another particular embodiment, the nucleic acid(s) encoding an aspartate transaminase may be nucleic acid(s) encoding an amino acid sequence selected from the group consisting of sequences having at least 39%, advantageously at least 65%, preferably at least 80%, identity with the amino acid sequence of SEQ ID NO: 21, and also a biological activity of the same nature.

A biological activity of the same nature regarding this sequence is as described previously, i.e. the capacity to catalyze the reaction of L-aspartate and 2-oxoglutarate for producing oxaloacetate and L-glutamate.

As described herein, an amino acid sequence having at least 39% amino acid identity with a reference nucleic acid sequence encompasses amino acid sequences having at least 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 21, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 21, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 21, and also a biological activity of the same nature.

As above-mentioned, the expression level of the aspartate transaminase in the present invention is regulated by at least one promoter and at least one terminator, such as herein after defined more in details, which are present in 5' and 3' position respectively of the nucleic acid sequence encoding the aspartate transaminase.

As it is specified elsewhere in the present description, aspartate transaminase is overexpressed in a recombinant yeast according to the invention.

In some embodiments, overexpression of aspartate transaminase may result from the control of the corresponding gene by a strong promoter within the said recombinant yeast.

In some other embodiments, overexpression of aspartate transaminase may result from the presence of a plurality of copies of an aspartate transaminase-encoding sequence within the genome the said recombinant yeast.

In still further embodiments, overexpression of aspartate transaminase may result from both (i) the control of the corresponding gene by a strong promoter within the said recombinant yeast and (ii) the presence of a plurality of copies of an aspartate transaminase-encoding sequence within the genome the said recombinant yeast.

Glutamate Dehydrogenase Over Expression and/or Controlled Expression

In preferred embodiments of a recombinant yeast according to the invention, at least one nucleic acid encoding a glutamate dehydrogenase that converts oxo-glutarate to glutamate-encoding gene is overexpressed and/or under the control of an inducible or repressible promoter.

Accordingly, in a particular embodiment, the genome of a recombinant yeast of the invention is such that at least one nucleic acid encoding a glutamate dehydrogenase that converts oxo-glutarate to glutamate is overexpressed and/or is under the control of an inducible or repressible promoter.

The glutamate dehydrogenase enzyme (also known as NAD-specific glutamate dehydrogenase) is a protein which is described in the art for catalyzing the transformation of 2-oxoglutarate for producing L-glutamate. Thus, glutamate dehydrogenase is an enzyme specifically involved in the chemical reaction involving the conversion of 2-oxoglutarate to L-glutamate, in the presence of NADH.

According to these embodiments, over expression of a glutamate dehydrogenase enzyme-encoding gene is obtained by inserting, at selected location(s) of the yeast genome, one or more copies of an expression cassette comprising a glutamate dehydrogenase coding sequence.

Glutamate dehydrogenase and a glutamate dehydrogenase-encoding gene that are encompassed by the invention are detailed elsewhere in the present specification.

In some of these embodiments, the said one or more copies of an expression cassette comprising a glutamate dehydrogenase coding sequence comprise regulatory sequences allowing a strong expression of the glutamate dehydrogenase, such as a strong promoter that is functional in yeast cells.

In addition to or as an alternative to these embodiments of a recombinant yeast according to the invention, at least one glutamate dehydrogenase-encoding gene can be under the control of an inducible or repressible promoter that is functional in yeast cells.

Without wishing to be bound by any particular theory the inventors believe that the over expression of the glutamate dehydrogenase, by converting oxoglutarate into glutamate, simultaneously generates NAD. The same applies when at least one glutamate dehydrogenase coding sequence is under the control of an inducible or repressible promoter.

A method implemented to measure the activity level of glutamate dehydrogenase belongs to the general knowledge of the one skilled in the art.

In this regard, the one skilled in the art may advantageously refer to the method described in Noor and Punekar (2005, Microbiology, Vol. 151: 1409-1419).

In preferred embodiments, the said glutamate dehydrogenase-encoding gene encodes for a glutamate dehydrogenase which uses NADH instead of NADPH, is more particularly the GDH gene from *Entodinium caudatum* (represented as GDH.Eca or GDH2.Eca) or from *Saccharomyces cerevisiae* (represented as GDH2), as shown in the examples herein. In a particular embodiment, the said glutamate dehydrogenase-encoding gene encodes for a glutamate dehydrogenase from *Entodinium caudatum*.

Preferred glutamate dehydrogenase in the present specification can in particular be the enzyme having the EC number n° EC 1.4.1.2.

In preferred embodiments, the said glutamate dehydrogenase-encoding gene is placed under the control of the strong promoter pTDH3 or the inducible or repressible promoter pCUP1-1.

Illustratively, the glutamate dehydrogenase gene may be inserted within the HIS3 gene and/or within the MUP3 gene, as it is shown in the examples herein.

According to a preferred embodiment, the nucleic acid(s) encoding a glutamate dehydrogenase may be nucleic acid(s) originating from organisms preferably selected in a group comprising prokaryotic organisms and eukaryotic organisms. In some embodiments, the nucleic acid(s) encoding a glutamate dehydrogenase may be nucleic acid(s) originating from archaebacteria. In some embodiments, the nucleic acid(s) encoding a glutamate dehydrogenase may be nucleic acid(s) originating from organisms preferably selected from *Entodinium caudatum, Bacillus subtilis, Clostridium symbiosium*.

According to a yet preferred embodiment, the nucleic acid(s) encoding a glutamate dehydrogenase may be nucleic acid(s) selected from the group consisting of sequences having at least 49%, advantageously at least 65%, preferably at least 80%, nucleic acid identity with the nucleic acid sequences of SEQ ID NO: 22, and also a biological activity of the same nature. The nucleic acid of SEQ ID NO. 22 encodes a glutamate dehydrogenase originating from *Entodinium caudatum*, the said nucleic acid sequence being codon-optimized for its expression in yeast, and especially in *Saccharomyces cerevisiae*.

A biological activity of the same nature regarding this sequence is the capacity to code for an enzyme that catalyzes the transformation of 2-oxoglutarate for producing L-glutamate.

As described herein, a nucleic acid sequence having at least 49% nucleotide identity with a reference nucleic acid sequence encompasses nucleic acid sequences having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 22, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 22, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 22, and also a biological activity of the same nature.

For the amino acid sequence of the glutamate dehydrogenase from *Entodinium caudatum*, the one skilled in the art may refer to the accession number AAF15393 in the UniProt database, or to SEQ ID NO. 23 described herein. Illustratively, the glutamate dehydrogenase originating from *Giardia intestinalis* has 49% amino acid identity with the glutamate dehydrogenase of SEQ ID NO. 23.

According to another particular embodiment, the nucleic acid(s) encoding a glutamate dehydrogenase may be nucleic acid(s) encoding an amino acid sequence selected from the group consisting of sequences having at least 49%, advantageously at least 65%, preferably at least 80%, amino acid identity with the amino acid sequence of SEQ ID NO: 23, and also a biological activity of the same nature.

A biological activity of the same nature regarding this sequence is as described previously, i.e. the capacity to catalyze the transformation of 2-oxoglutarate for producing L-glutamate.

As described herein, an amino acid sequence having at least 49% amino acid identity with a reference nucleic acid sequence encompasses amino acid sequences having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 23, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 23, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 23, and also a biological activity of the same nature.

As above-mentioned, the expression level of the glutamate dehydrogenase in the present invention is regulated by at least one promoter and at least one terminator, such as herein after defined more in details, which are present in 5' and 3' position respectively of the nucleic acid sequence encoding the said glutamate dehydrogenase.

As it is specified elsewhere in the present description, the glutamate dehydrogenase is overexpressed in a recombinant yeast according to the invention.

In some embodiments, overexpression of the glutamate dehydrogenase may result from the control of the corresponding gene by a strong promoter within the said recombinant yeast.

In some other embodiments, overexpression of the glutamate dehydrogenase may result from the presence of a plurality of copies of a glutamate dehydrogenase-encoding sequence within the genome the said recombinant yeast.

In still further embodiments, overexpression of the glutamate dehydrogenase may result from both (i) the control of the corresponding gene by a strong promoter within the said recombinant yeast and (ii) the presence of a plurality of copies of a glutamate dehydrogenase-encoding sequence within the genome the said recombinant yeast.

Export of the Compounds of Interest

In further embodiments of a recombinant yeast according to the invention, the export of the produced ectoine outside of the yeast cell may be enhanced by (i) under expression of genes encoding yeast permeases, by (ii) under expression of genes encoding amino acid exporter proteins, or by (iii) both under expression of genes encoding yeast permeases and under expression of genes encoding amino acid exporter proteins.

Under Expression of Permease-Encoding Gene(s)

As it is described below, permease-encoding genes that may be under expressed in a recombinant yeast according to the invention encompass AGP1, AGP3, BAP3, BAP2, GAP1, GNP1, MUP3 and MUP1.

AGP1 is the general amino acid permease 1 from *Saccharomyces cerevisiae*. For the amino acid sequence of AGP1 it may be referred to the access number NP_009905 in the UniProt database. For the nucleic acid sequence, it may be referred to the access number NM_001178671 in the NCBI database.

AGP3 is the general amino acid permease 3 from *Saccharomyces cerevisiae*. For the amino acid sequence of AGP3 it may be referred to the access number NP_116600 in the UniProt database. For the nucleic acid sequence, it may be referred to the access number NM_001179912 in the NCBI database.

BAP3 is the valine amino acid permease from *Saccharomyces cerevisiae*. For the amino acid sequence of BAP3 it may be referred to the access number NP_010331 in the UniProt database. For the nucleic acid sequence, it may be referred to the access number NM_001180354 in the NCBI database.

BAP2 is the Leu/Val/Ile amino acid permease from *Saccharomyces cerevisiae*. For the amino acid sequence of BAP2 it may be referred to the access number NP_009624 in the UniProt database. For the nucleic acid sequence, it may be referred to the access number NM_001178416 in the NCBI database.

GAP1 is the general amino-acid permease from *Saccharomyces cerevisiae*. For the amino acid sequence of GAP1 it may be referred to the access number NP_012965.3 in the UniProt database. For the nucleic acid sequence, it may be referred to the access number NM_001179829 in the NCBI database.

GNP1 is the high-affinity glutamine permease from *Saccharomyces cerevisiae*. For the amino acid sequence of GNP1 it may be referred to the access number NP_010796 in the UniProt database. For the nucleic acid sequence, it may be referred to the access number NM_001180816 in the NCBI database.

MUP3 is the low-affinity methionine permease from *Saccharomyces cerevisiae*. For the amino acid sequence of MUP3 it may be referred to the access number NP_011827 in the UniProt database. For the nucleic acid sequence, it may be referred to the access number NM_001179116 in the NCBI database.

MUP1 is the low-affinity methionine permease from *Saccharomyces cerevisiae*. For the amino acid sequence of MUP it may be referred to the access number NP_011569 in the UniProt database. For the nucleic acid sequence, it may be referred to the access number NM_001181184 in the NCBI database.

In some embodiments of a recombinant yeast according to the invention, the said recombinant yeast is further defined as having an under expression one or more genes encoding a permease, that encompasses AGP1, AGP3, BAP3, BAP2, GAP1, GNP1, MUP3 and MUP1 permeases.

Accordingly, in a particular embodiment, the genome of a recombinant yeast of the invention is such that at least one of the following modifications has been performed:

(A) at least one, preferably all, endogenous nucleic acid encoding a general amino acid permease AGP3 have been deleted from the genome of the yeast, and optionally:
  (i) at least one nucleic acid encoding a general amino acid permease AGP3 has been inserted and is under the control of an inducible or repressible promoter, and/or
  (ii) at least one nucleic acid encoding a destabilized general amino acid permease AGP3 has been inserted;

(B) at least one, preferably all, endogenous nucleic acid encoding a branched-chain amino-acid permease 3 has been deleted from the genome of the yeast, and, optionally:
  (i) at least one nucleic acid encoding a branched-chain amino-acid permease 3 has been inserted and is under the control of an inducible or repressible promoter, and/or
  (ii) at least one nucleic acid encoding a destabilized branched-chain amino-acid permease 3 has been inserted;

(C) at least one, preferably all, endogenous nucleic acid encoding a branched-chain amino-acid permease 2 has been deleted from the genome of the yeast, and, optionally:
  (i) at least one nucleic acid encoding a branched-chain amino-acid permease 2 has been inserted and is under the control of an inducible or repressible promoter, and/or (ii) at least one nucleic acid encoding a destabilized branched-chain amino-acid permease 2 has been inserted;

(D) at least one, preferably all, endogenous nucleic acid encoding a general amino acid permease GAP1 has been deleted from the genome of the yeast, and, optionally:
  (i) at least one nucleic acid encoding a general amino acid permease GAP1 has been inserted and is under the control of an inducible or repressible promoter, and/or
  (ii) at least one nucleic acid encoding a destabilized general amino acid permease GAP1 has been inserted;

(E) at least one, preferably all, endogenous nucleic acid encoding a high-affinity glutamine permease GNP1 has been deleted from the genome of the yeast, and, optionally:
  (i) at least one nucleic acid encoding a high-affinity glutamine permease GNP1 has been inserted and is under the control of an inducible or repressible promoter, and/or
  (ii) at least one nucleic acid encoding a destabilized high-affinity glutamine permease GNP1 has been inserted;

(F) at least one, preferably all, endogenous nucleic acid encoding a general amino acid permease AGP1 has been deleted from the genome of the yeast, and, optionally:
  (i) at least one nucleic acid encoding a general amino acid permease AGP1 has been inserted and is under the control of an inducible or repressible promoter, and/or
  (ii) at least one nucleic acid encoding a destabilized general amino acid permease AGP1 has been inserted;

(G) at least one, preferably all, endogenous nucleic acid encoding a low-affinity methionine permease MUP3 has been deleted from the genome of the yeast, and, optionally:
  (i) at least one nucleic acid encoding a low-affinity methionine permease MUP3 has been inserted and is under the control of an inducible or repressible promoter, and/or
  (ii) at least one nucleic acid encoding a destabilized low-affinity methionine permease MUP3 has been inserted;

(H) at least one, preferably all, endogenous nucleic acid encoding a high-affinity methionine permease MUP1 has been deleted from the genome of the yeast, and, optionally:
  (i) at least one nucleic acid encoding a high-affinity methionine permease MUP1 has been inserted and is under the control of an inducible or repressible promoter, and/or
  (ii) at least one nucleic acid encoding a destabilized high-affinity methionine permease MUP1 has been inserted;

(I) at least one nucleic acid encoding a probable transporter AQR1 is overexpressed; and/or (J) at least one nucleic acid encoding a polyamine transporter 1 is overexpressed.

In a particular embodiment, at least two, in particular at least three of these modifications have been performed.

Without wishing to be bound by any particular theory, the inventors believe that an under expression of any of the permease genes shall increase the excretion of the produced ectoine outside the yeast cell, e.g. in the culture medium.

As regards permeases under expression of one or more of these genes encompasses a complete repression of their expression, e.g. by interruption or deletion of the said one or more permease genes.

In some embodiments, under expression of a permease-encoding gene may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

As regards a permease gene, under expression also encompasses the insertion of a nucleic acid encoding a destabilized permease protein or the insertion of a nucleic acid encoding a destabilized permease protein, or both.

A destabilized permease is a variant of a permease that is more rapidly degraded within the yeast cell than the parent permease.

In preferred embodiments, a destabilized permease consists of a degron-tagged permease protein.

As illustrated in the examples, the AGP3 gene, the BAP3 gene, the GAP1 gene, the GNP1 gene and the MUP3 gene can be interrupted by loxP and are thus deleted.

Over Expression of Amino Acid Exporter Protein-Encoding Gene(s)

As it is described below, exporter protein-encoding genes that may be over expressed in a recombinant yeast according to the invention encompass AQR1 and TPO1.

AQR1 is a transporter from *Saccharomyces cerevisiae*. For the amino acid sequence of AQR1 it may be referred to the access number NP_014334 in the UniProt database. For the nucleic acid sequence, it may be referred to the access number NM_001182903 in the NCBI database.

TPO1 is a polyamine transporter from *Saccharomyces cerevisiae*. For the amino acid sequence of TPO1 it may be referred to the access number NP_013072 in the UniProt database. For the nucleic acid sequence, it may be referred to the access number NM_001181848 in the NCBI database.

In preferred embodiments of a recombinant yeast according to the invention, over expression of a transporter-encoding gene is obtained by inserting, at selected location(s) of the yeast genome, one or more additional copies of an expression cassette comprising the said transporter coding sequence.

Without wishing to be bound by any particular theory, the inventors believe that an over expression of a transporter-encoding gene shall increase the excretion of the produced ectoine outside the yeast cell, e.g. in the culture medium.

In some embodiments, over expression of a transporter-encoding gene is obtained by inserting, at selected location(s) of the yeast genome, one or more additional copies of an expression cassette comprising a transporter gene coding sequence. In some of these embodiments, the said one or more copies of an expression cassette comprising a transporter coding sequence comprise regulatory sequences allowing a strong expression of the said transporter, such as a strong promoter that is functional in yeast cells.

In some other embodiments, one copy of a transporter-encoding gene is inserted at a selected location of the yeast genome. In these other embodiments, the said one or more copies of an expression cassette comprising a transporter coding sequence comprise regulatory sequences allowing a strong expression of the said transporter, such as a strong promoter that is functional in yeast cells.

In preferred embodiments, the said amino acid exporter protein-encoding gene AQR1 is placed under the control of the strong promoter pTEF3.

Illustratively, the AQR1 gene may be inserted within the PYK1 gene, as it is shown in the examples herein.

In preferred embodiments, the said amino acid exporter protein-encoding gene_TPO1 is placed under the control of the strong inducible or repressible promoter pSAM4 or the strong constitutive promoter pTEF1.

TPO1-1 can be used instead of TPO1. TPO1-1 is an artificial allele in which the lysines 10, 49, 86, 143, 144 and 145 are replaced by arginines.

It is believed by the inventors that these modifications protect TP01 from degradation through the ubiquitin-proteasome pathway, thus stabilizing it.

In preferred embodiments, the said amino acid exporter protein-encoding gene_TPO1 is placed under the control of the strong promoter pTEF3.

Illustratively, the TPO1 gene may be inserted within the PYK1 gene, as it is shown in the examples herein.

In view of further increasing ectoine production, a recombinant yeast according to the invention may comprise additional genetic changes, such that they produce large quantities of the intermediate product oxaloacetate. These optional genetic changes are described here below.

Further Embodiments of an Ectoine-Producing Recombinant Yeast

According to some embodiments of a recombinant yeast according to the invention, production of ectoine may be further increased by placing the said recombinant yeast in conditions leading to an increase production of the intermediate metabolite oxaloacetate.

Placing the said recombinant yeast in conditions leading to an increased production of oxaloacetate may be performed by introducing further genetic modifications in the yeast genome.

The present inventors have found that an optimally increased ectoine production may be reached by introducing further genetic changes to the ectoine-producing recombinant yeast, that are described below.

First Further Embodiments of a Ectoine-Producing Recombinant Yeast

According to these first further embodiments of a ectoine-producing recombinant yeast according to the invention, further genetic engineering of the recombinant yeast is performed with the aim of increasing the production of the intermediate product phosphoenol-pyruvate (PEP).

Without wishing to be bound by any particular theory, the inventors believe that the further genetic changes introduced in the ectoine-producing recombinant yeast (i) cause an over-production of NADPH, (ii) cause a controlled and balanced conversion of phosphoenol pyruvate into oxaloacetate and pyruvate, respectively, and (iii) cause a reduced conversion of pyruvate into ethanol and a redirection towards conversion of phosphoenol pyruvate into oxaloacetate.

These further genetic changes introduced by genetic engineering in a ectoine-producing recombinant yeast according to the invention are specified in more detail below.

According to these embodiments, genetic changes are introduced so as to over-express a glucose-6-phosphate-1-dehydrogenase (also termed MET19 or ZWF1) and a 6-phosphogluconate dehydrogenase, decarboxylating 1 (also termed GND1). Without wishing to be bound by any particular theory, the inventors believe that an over expression of MET19 and GND1 causes an increase in NADPH production.

According to these embodiments, genetic changes are introduced so as to over-express a phosphoenolpyruvate carboxylase (also termed PEPC ou PPC) and/or a phosphoenolpyruvate carboxykinase [ATP] (also termed PCK1 or PEPCK).

According to these embodiments, genetic changes are introduced so as to under-express a pyruvate kinase 1 (also termed PYK1 or CDC19) and a pyruvate kinase 2 (also termed (PYK2). In some of these embodiments, PYK2 gene may be deleted rather than being under-expressed.

In some of these embodiments, one or more of the genes encoding a pyruvate decarboxylase is (are) inactivated, preferably by deletion. Pyruvate decarboxylase-encoding genes encompass those termed PDC1, PDC5 and PDC6, respectively. According to some of these embodiments, PDC1 and/or PDC6 genes are inactivated, preferably by interruption or deletion, whereas the other pyruvate decarboxylase-encoding gene PDC5 is left unaltered; Or its expression is reduced by controlling it with a weak promoter.

In some of these embodiments, alcohol dehydrogenase activity of the recombinant yeast is reduced by altering the expression of one or more of the alcohol dehydrogenase-encoding genes. In some of these embodiments, the expression of ADH1 is reduced by placing the gene under the control of a weak promoter or by producing a destabilized ADH1 enzyme. In some of these embodiments, one or more of ADH3, ADH4 and ADH5 may be inactivated, preferably by interruption or deletion.

In some of these embodiments, an exogenous acetyl dehydrogenase-encoding gene (also termed MHPF) may be introduced in the yeast genome and over-expressed.

In some of these embodiments, an exogenous acetate kinase-encoding gene (also termed ACKA) may be introduced in the yeast genome and over-expressed.

In some of these embodiments, an exogenous phosphate acetyl transferase-encoding gene (also termed PTA) may be introduced in the yeast genome and over-expressed.

Glucose-6-phosphate-1-dehydrogenase

The glucose-6-phosphate-1-dehydrogenase enzyme is a protein which is described in the art for catalyzing D-glucose 6-phosphate to 6-phospho-D-glucono-1,5-lactone, with concomitant reduction of NADP to NADPH.

A method implemented to measure the activity level of glucose-6-phosphate-1-dehydrogenase belongs to the general knowledge of the one skilled in the art.

In this regard, the one skilled in the art may advantageously refer to the method described by Kuby, S. et al. (1966) Dehydrogenases and Oxidases Methods in Enzymology 9, 116-117.

Preferred glucose-6-phosphate-1-dehydrogenase in the present specification is an enzyme having an EC number of n° 1.1.1.49.

For the amino acid sequence of glucose-6-phosphate-1-dehydrogenase (also termed MET19), it may be referred to the access number NP_014158.1 in the UniProt database. For the nucleic acid sequence, it may be referred to the access number NM_001183079.1 in the UniProt database.

6-phosphogluconate dehydrogenase, decarboxylating/ The 6-phosphogluconate dehydrogenase, decarboxylating 1 enzyme is a protein which is described in the art for catalyzing the oxidative decarboxylation of 6-phosphogluconate to ribulose 5-phosphate and CO2, with concomitant reduction of NADP to NADPH.

A method implemented to measure the activity level of 6-phosphogluconate dehydrogenase, decarboxylating 1 belongs to the general knowledge of the one skilled in the art.

In this regard, the one skilled in the art may advantageously refer to the method described by He W. et al. (2007) BMC Structural Biology, 7:38.

Preferred 6-phosphogluconate dehydrogenase, decarboxylating 1 in the present specification is an enzyme having an EC number of n° 1.1.1.44.

For the amino acid sequence of 6-phosphogluconate dehydrogenase, decarboxylating 1 (also termed GND1), it may be referred to the access number NP_012053 in the UniProt database. For the nucleic acid sequence, it may be referred to the access number NM_001179314 in the NCBI database.

Pyruvate Kinase 1

The pyruvate kinase 1 enzyme is a protein which is described in the art for catalyzing the conversion of pyruvate into phosphoenolpyruvate, in the presence of ATP.

A method implemented to measure the activity level of pyruvate kinase 1 belongs to the general knowledge of the one skilled in the art.

In this regard, the one skilled in the art may advantageously refer to the method described by Susan-resiga and Nowak (biochemistry, 2004, 43, 15230-15245).

Preferred pyruvate kinase 1 in the present specification is an enzyme having an EC number of n° 2.7.1.40.

For the amino acid sequence of pyruvate kinase 1 (also termed PYK1) it may be referred to the access number NP_009362 in the UniProt database. For the nucleic acid sequence, it may be referred to the access number NM_001178183 in the NCBI database.

Pyruvate Kinase 2

The pyruvate kinase 2 enzyme is a protein which is described in the art for catalyzing the conversion of pyruvate into phosphoenolpyruvate, in the presence of ATP. Pyruvate kinase 2 may be used by the yeast cell under conditions in which the level of glycolytic flux is very low.

A method implemented to measure the activity level of pyruvate kinase 2 belongs to the general knowledge of the one skilled in the art.

In this regard, the one skilled in the art may advantageously refer to the method described by Susan-resiga and Nowak (biochemistry, 2004, 43, 15230-15245).

Preferred pyruvate kinase 2 in the present specification is an enzyme having an EC number of n° 2.7.1.40.

For the amino acid sequence of pyruvate kinase 2 (also termed PYK2) it may be referred to the access number NP_014992 in the UniProt database. For the nucleic acid sequence, it may be referred to the access number NM_001183767 in the NCBI database.

Pyruvate Decarboxylase Isozyme 1

The pyruvate decarboxylase isozyme 1 is a protein which is described in the art for being involved in the non-oxidative conversion of pyruvate to acetaldehyde and carbon dioxide during alcoholic fermentation.

A method implemented to measure the activity level of the pyruvate decarboxylase isozyme 1 belongs to the general knowledge of the one skilled in the art.

In this regard, the one skilled in the art may advantageously refer to the method described by Wang et al. (Biochemistry, 2001, 40:1755-1763).

Preferred pyruvate decarboxylase isozyme 1 in the present specification is an enzyme having an EC number of n° 4.1.1.1.

For the amino acid sequence of pyruvate decarboxylase isozyme 1 (also termed PDC1) it may be referred to the access number NP_013145 in the UniProt database. For the nucleic acid sequence, it may be referred to the access number NM_001181931 in the NCBI database.

Pyruvate Decarboxylase Isozyme 5

The pyruvate decarboxylase isozyme 5 is a protein which is described in the art for being involved in the nonoxidative conversion of pyruvate to acetaldehyde and carbon dioxide during alcoholic fermentation.

A method implemented to measure the activity level of the pyruvate decarboxylase isozyme 5 belongs to the general knowledge of the one skilled in the art.

In this regard, the one skilled in the art may advantageously refer to the method described by Wang et al. (Biochemistry, 2001, 40:1755-1763).

Preferred pyruvate decarboxylase isozyme 5 in the present specification is an enzyme having an EC number of n° 4.1.1.1.

For the amino acid sequence of pyruvate decarboxylase isozyme 5 (also termed PDC5) it may be referred to the access number NP_013235 in the UniProt database. For the nucleic acid sequence, it may be referred to the access number NM_001182021 in the NCBI database.

Pyruvate Decarboxylase Isozyme 6

The pyruvate decarboxylase isozyme 6 is a protein which is described in the art for being involved in the nonoxidative conversion of pyruvate to acetaldehyde and carbon dioxide during alcoholic fermentation.

A method implemented to measure the activity level of the pyruvate decarboxylase isozyme 5 belongs to the general knowledge of the one skilled in the art. In this regard, the one skilled in the art may advantageously refer to the method described by Wang et al. (Biochemistry, 2001, 40:1755-1763).

Preferred pyruvate decarboxylase isozyme 6 in the present specification is an enzyme having an EC number of n° 4.1.1.1.

For the amino acid sequence of pyruvate decarboxylase isozyme 6 (also termed PDC6) it may be referred to the access number NP_013235 in the UniProt database. For the nucleic acid sequence, it may be referred to the access number NM_001182021 in the NCBI database.

Acetaldehyde Dehydrogenase

The acetaldehyde dehydrogenase is a protein which is described in the art for catalyzing the conversion of acetaldehyde to acetyl-CoA, using NAD and coenzyme A.

A method implemented to measure the activity level of acetaldehyde dehydrogenase belongs to the general knowledge of the one skilled in the art.

In this regard, the one skilled in the art may advantageously refer to the method described by Fisher et al. (2013) Chemi. Biol. Interact. 202 70-77.

Preferred acetaldehyde dehydrogenase in the present specification is an enzyme having an EC number of n° 1.1.1.10.

For the amino acid sequence of acetaldehyde dehydrogenase (also termed MHPF) it may be referred to the access number NP_414885 in the UniProt database. For the nucleic acid sequence, it may be referred to the one disclosed in the access number NC_000913.3 in the NCBI database.

Acetate Kinase

The acetate kinase is a protein which is described in the art for the formation of acetyl phosphate from acetate and ATP.

A method implemented to measure the activity level of acetate kinase belongs to the general knowledge of the one skilled in the art.

In this regard, the one skilled in the art may advantageously refer to the method described by Sagers et al. J. Bacteriology (1961) 82 233-238.

For the amino acid sequence of acetate kinase (also termed ACKA) it may be referred to the access number NP_416799 in the UniProt database. For the nucleic acid sequence, it may be referred to the one disclosed in the access number NC_000913.3 in the NCBI database.

Phosphate Acetyltransferase

The phosphate acetyltransferase is a protein which is described in the art for catalyzing the reversible interconversion of acetyl-CoA and acetyl phosphate.

A method implemented to measure the activity level of the phosphate acetyltransferase belongs to the general knowledge of the one skilled in the art.

In this regard, the one skilled in the art may advantageously refer to the method described by Castano-Cerezo and Canovas, Microbial Cell Factories 2009, 8:54.

Preferred phosphate acetyltransferase in the present specification is an enzyme having an EC number of n° 2.3.1.8.

For the amino acid sequence of phosphate acetyltransferase (also termed PTA) it may be referred to the access number NP_416800 in the UniProt database. For the nucleic acid sequence, it may be referred to the one disclosed in the access number NC_000913 in the NCBI database.

Alcohol Dehydrogenase 1

The alcohol dehydrogenase 1 is a protein which is described in the art for catalyzing the conversion of primary unbranched alcohols to their corresponding aldehydes.

A method implemented to measure the activity level of the alcohol dehydrogenase 1 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 1 in the present specification is an enzyme having an EC number of n° 1.1.1.1.

For the amino acid sequence of alcohol dehydrogenase 1 (also termed ADH1) it may be referred to the access number NP_014555 in the UniProt database. For the nucleic acid sequence, it may be referred to the access number NM_001183340 in the NCBI database.

Alcohol Dehydrogenase 3

The alcohol dehydrogenase 3 is a protein which is described in the art for catalyzing the conversion of primary unbranched alcohols to their corresponding aldehydes.

A method implemented to measure the activity level of the alcohol dehydrogenase 3 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 3 in the present specification is an enzyme having an EC number of n° 1.1.1.1.

For the amino acid sequence of alcohol dehydrogenase 3 (also termed ADH3) it may be referred to the access number NP_013800 in the UniProt database. For the nucleic acid sequence, it may be referred to the access number NM_001182582 in the NCBI database.

Alcohol Dehydrogenase 4

The alcohol dehydrogenase 4 is a protein which is described in the art for catalyzing the conversion of primary unbranched alcohols to their corresponding aldehydes.

A method implemented to measure the activity level of the alcohol dehydrogenase 4 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 4 in the present specification is an enzyme having an EC number of n° 1.1.1.1.

For the amino acid sequence of alcohol dehydrogenase 4 (also termed ADH4) it may be referred to the access number NP_011258 in the UniProt database. For the nucleic acid sequence, it may be referred to the access number NM_001181122 in the NCBI database.

Alcohol Dehydrogenase 5

The alcohol dehydrogenase 5 is a protein which is described in the art for catalyzing the conversion of primary unbranched alcohols to their corresponding aldehydes.

A method implemented to measure the activity level of the alcohol dehydrogenase 5 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 5 in the present specification is an enzyme having an EC number of n° 1.1.1.1.

For the amino acid sequence of alcohol dehydrogenase 5 (also termed ADH5) it may be referred to the access number NP_009703 in the UniProt database. For the nucleic acid sequence, it may be referred to the access number NM_001178493 in the NCBI database.

Second Further Embodiments of a Ectoine-Producing Recombinant Yeast

According to these further embodiments of a ectoine-producing recombinant yeast according to the invention, further genetic engineering of the recombinant yeast is performed with the aim of increasing the production of the intermediate product phosphoenol-pyruvate (PEP).

Without wishing to be bound by any particular theory, the inventors believe that the further genetic changes introduced in the ectoine-producing recombinant yeast (i) cause an over-production of NADPH, (ii) cause a controlled and balanced conversion of phosphoenol pyruvate into oxaloacetate and pyruvate, respectively, and (iii) cause a reduced conversion of pyruvate into ethanol and a redirection towards conversion of phosphoenol pyruvate into oxaloacetate.

For this purpose, the inventors have conceived a completely novel metabolic pathway, starting from phosphenolpyruvate and ending with the production of oxaloacetate.

These further genetic changes introduced by genetic engineering in a ectoine-producing recombinant yeast according to the invention are specified in more detail below.

According to these embodiments, genetic changes are introduced so as to under express the pyruvate kinase 1 (also termed PYK1), and optionally also pyruvate kinase 2 (also termed PYK2). In some of these embodiments, PYK1 may be under-expressed by placing the gene under the control of a weak promoter or of an inducible or repressible promoter. In some of these embodiments, PYK2 may be inactivated, e.g. by interruption or deletion. In some of these embodiments, PYK1 gene may be deleted rather than being under-expressed. In some of these embodiments, PYK1 gene and PYK2 gene may be deleted rather than being under-expressed.

According to these embodiments, genetic changes are introduced so as to over-express a phosphoenolpyruvate carboxykinase [ATP] (also termed PCK or PCKA or PEPCK), either (i) by constitutive over-expression or (ii) by inducible over-expression.

According to these embodiments, genetic changes are introduced so as over-express in the cytoplasm a malate dehydrogenase, such as a peroxisomal malate dehydrogenase (also termed MDH3), either (i) by constitutive over-expression or (ii) by inducible over-expression.

According to these embodiments, genetic changes are introduced so as over-express a NADP-dependent malic enzyme 3 (also termed ME3 or NADP-ME3), either (i) by constitutive over-expression or (ii) by inducible over-expression.

According to these embodiments, genetic changes are introduced so as to reduce expression of one or more alcohol dehydrogenase(s), preferably one or more alcohol dehydrogenase(s) selected in a group comprising alcohol dehydrogenase 1 (also termed ADH1), alcohol dehydrogenase 3 (also termed ADH3), alcohol dehydrogenase 4 (also termed ADH4) and alcohol dehydrogenase 5 (also termed ADH5), e.g. (i) by placing the corresponding coding sequence under the control of a weak promoter or of an inducible or repressible promoter, or (ii) by production of a destabilized form of the said alcohol dehydrogenase(s).

Still according to these embodiments, genetic changes are introduced so as to over-express an exogenous acetaldehyde dehydrogenase (also termed MHPF), either (i) by constitutive over-expression or (ii) by inducible over-expression.

Phosphoenolpyruvate Carboxykinase (PPCK)

The phosphoenol carboxykinase [ATP] enzyme is a protein which is described in the art for catalyzing the conversion of oxaloacetate to phosphoenolpyruvate through direct phosphoryl transfer between the nucleoside triphosphate and oxaloacetate.

A method implemented to measure the activity level of phosphoenol carboxykinase [ATP] belongs to the general knowledge of the one skilled in the art.

In this regard, the one skilled in the art may advantageously refer to the method described by Bazaes S. et al. (2007) The Protein Journal, 26, 265-269 and Mariet J. Van der Werf et al. (1997) Arch Microbiol 167: 332-342.

Preferred phosphoenol carboxykinase [ATP] in the present specification is an enzyme having an EC number of n° 4.1.1.49.

For the amino acid sequence of phosphoenol carboxykinase [ATP] (also termed PCKA) it may be referred to the access number NP_417862 in the UniProt database. For the nucleic acid sequence, it may be referred to the one disclosed in the access number NC 000913 in the NCBI database.

Preferred phosphoenol carboxykinase according to the invention can be selected from phosphoenolpyruvate carboxykinase PPCK such as PEPCK having an EC number of n° 4.1.1.32.

Malate Dehydrogenase

The malate dehydrogenase enzyme is a protein which is described in the art for catalyzing the conversion of malate to oaxaloacetate, in the presence of NADH.

A method implemented to measure the activity level of malate dehydrogenase belongs to the general knowledge of the one skilled in the art. Mention can for example be made of the commercial kit sold by Sigma entitled "Malate dehydrogenase assay kit" under the reference MAK196-1KT.

For the amino acid sequence of malate dehydrogenase (also termed MDH3) it may be referred to the access number NP_010205 in the UniProt database. For the nucleic acid sequence, it may be referred to the access number NM_00118037 in the NCBI database.

NADP-Dependent Malic Enzyme 3

The NADP-dependent malic enzyme 3 enzyme is a protein which is described in the art for catalyzing the conversion of malate to pyruvate, in the presence of NADP.

A method implemented to measure the activity level of NADP-dependent malic enzyme 3 belongs to the general knowledge of the one skilled in the art.

In this regard, the one skilled in the art may advantageously refer to the method described by Gerrard-Wheeler et al. FEBS Journal 276 (2009) 5665-5677.

Preferred NADP-dependent malic enzyme 3 in the present specification is an enzyme having an EC number of n° 1.1.1.40.

For the amino acid sequence of NADP-dependent malic enzyme 3 (also termed NADP-ME3 or ME3) it may be referred to the access number NP_197960 in the UniProt database. For the nucleic acid sequence, it may be referred to the access number NM_122489 in the NCBI database.

Alcohol dehydrogenase 1, alcohol dehydrogenase 3, alcohol dehydrogenase 4, alcohol dehydrogenase 5 and acetaldehyde dehydrogenase are as indicated here-above.

Promoters

As it is disclosed herein, the expression of the genes of interest that have been genetically engineered for obtaining a recombinant yeast according to the invention comprise appropriate regulatory sequences that are functional in yeast cells, including in *Saccharomyces cerevisiae*.

As disclosed in the present specification, various promoters may be used for the desired expression of the coding sequences of interest, which include (i) constitutive strong promoters (also called strong promoters in the present text), (ii) constitutive weak promoters (also called weak promoters in the present text) and (iii) inducible or repressible promoters. A list of yeast promoter with their relative activities in different media can be found in Keren et al. (2013) Molecular Systems Biology 9:701.

Promoters allowing the constitutive over-expression of a given gene, may be found in literature (Velculescu et al. (1997) Cell 88, 243-251).

Strong promoters more particularly interesting in the present invention may be selected from the group comprising:
pTDH3 (SEQ ID N° 24),
pENO2 (SEQ ID N° 25),
pTEF K1 (SEQ ID N° 26),
pTEF3 (SEQ ID N° 27),
pTEF1 (SEQ ID N° 28),
pADH1 (SEQ ID N° 29),
pGMP1 (SEQ ID N° 30),
pFBA1 (SEQ ID N° 31),
pPDC1 (SEQ ID N° 32),
pCCW12 (SEQ ID N° 33), and
pGK1 (SEQ ID N° 34).

According to a particular embodiment, the strong promoter according to the invention is, independently, selected from the group consisting of pTDH3, pENO2, pTEF-K1, pTEF3, pTEF1, pADH1, pGMP1, pFBA1, pPDC1, pCCW12 and pGK1.

Weak promoters more particularly interesting in the present invention may be selected from the group comprising:
pURA3 (SEQ ID N° 36),
pRPLA1 (SEQ ID N° 37),
pNUP57 (SEQ ID N° 119), and
pGAP1 (SEQ ID N° 120).

According to a particular embodiment, the weak promoter according to the invention is, independently, selected from the group consisting of pURA3, pRPLA1, pNUP57 and pGAP1.

As previously mentioned, inducible or repressible promoters are promoters whose activity is controlled by the presence or absence of biotic or abiotic factors and also by the quantity of said factor. Accordingly, for some promoters, their activity will in particular be induced and thus increased when the quantity of a given factor increases or is increased, and, accordingly, the activity of these same promoters can be repressed and thus reduced when the quantity of said factor diminishes or is reduced. The quantity of said factor(s) in the culture medium of a recombinant yeast of the invention comprising inducible or repressible promoters can be decided and thus controlled by the man skilled in the art.

For example, increasing the quantity of methionine in a culture medium of a recombinant yeast according to the invention comprising a pSAM4 promoter will induce and thus increase transcription of the gene under the control of this promoter. On the contrary, reducing the quantity of methionine in said culture medium will lead to a repression, and thus a reduced, transcription of the gene under the control of this promoter.

In another example, increasing the quantity of copper in a culture medium of a recombinant yeast according to the invention comprising a pCTR1 promoter will repress and thus decrease transcription of the gene under the control of this promoter. On the contrary, reducing the quantity of copper in said culture medium will lead to an induced, and thus an increased, transcription of the gene under the control of this promoter.

For this reason, the following promoters are referred to in the present text as being "inducible or repressible promoters".

According to a first embodiment, inducible or repressible promoters according to the invention may be selected from the group comprising promoters inducible or repressible with copper, promoters inducible or repressible with methionine and promoters inducible or repressible with threonine, and are in particular selected from the group consisting of:
  pSAM4—methionine inducible or repressible (SEQ ID N° 38),
  pCUP1-1—copper inducible or repressible (SEQ ID N° 39),
  pCUP1.cgla—copper inducible or repressible (SEQ ID N° 40),
  pCUP1.sba—copper inducible or repressible (SEQ ID N° 41),
  pACU1—copper inducible or repressible (SEQ ID N° 42),
  pACU2—copper inducible or repressible (SEQ ID N° 43),
  pACU3p—copper inducible or repressible (SEQ ID N° 44),
  pACU4p—copper inducible or repressible (SEQ ID N° 45),
  pACU5—copper inducible or repressible (SEQ ID N° 46),
  pACU6—copper inducible or repressible (SEQ ID N° 47),
  pACU7—copper inducible or repressible (SEQ ID N° 48),
  pACU8—copper inducible or repressible (SEQ ID N° 49),
  pACU9—copper inducible or repressible (SEQ ID N° 50),
  pACU10p—copper inducible or repressible (SEQ ID N° 51),
  pACU11—copper inducible or repressible (SEQ ID N° 52),
  pACU12—copper inducible or repressible (SEQ ID N° 53),
  pACU13—copper inducible or repressible (SEQ ID N° 54),
  pACU14—copper inducible or repressible (SEQ ID N° 55),
  pACU15—copper inducible or repressible (SEQ ID N° 56),
  pGAL/CUPlp—copper inducible or repressible (SEQ ID N° 57),
  pCRS5—copper inducible or repressible (SEQ ID N° 58), and
  pCHA1—threonine inducible or repressible (SEQ ID N° 59).

According to this embodiment, the inducible or repressible promoter according to the invention can in particular, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, and pCHA1.

The activity of these promoters is thus induced by the increasing presence of methionine, copper or threonine as indicated above, and their activity diminishes, i.e. is repressed, when the quantity of methionine, copper or threonine is reduced.

According to a second embodiment, inducible or repressible promoters according to the invention may be selected from the group comprising promoters inducible or repressible with copper, promoters inducible or repressible with lysine and promoters inducible or repressible with methionine, and in particular selected from the group consisting of:
  pCTR1—copper inducible or repressible (SEQ ID N° 60),
  pCTR3—copper inducible or repressible (SEQ ID N° 61),
  pCUR1—copper inducible or repressible (SEQ ID N° 62),
  pCUR2—copper inducible or repressible (SEQ ID N° 63),
  pCUR3—copper inducible or repressible (SEQ ID N° 64),
  pCUR4—copper inducible or repressible (SEQ ID N° 65),
  pCUR5p—copper inducible or repressible (SEQ ID N° 66),
  pCUR6—copper inducible or repressible (SEQ ID N° 67),
  pCUR7—copper inducible or repressible (SEQ ID N° 68),
  pCUR8—copper inducible or repressible (SEQ ID N° 69),
  pCUR9—copper inducible or repressible (SEQ ID N° 70),
  pCUR10—copper inducible or repressible (SEQ ID N° 71),
  pCUR11—copper inducible or repressible (SEQ ID N° 72),
  pCUR12—copper inducible or repressible (SEQ ID N° 73),
  pCUR13—copper inducible or repressible (SEQ ID N° 74),
  pCUR14—copper inducible or repressible (SEQ ID N° 75), pCUR15—copper inducible or repressible (SEQ ID N° 76),
pCUR16—copper inducible or repressible (SEQ ID N° 77),
pCUR17—copper inducible or repressible (SEQ ID N° 78),
pLYS1—lysine inducible or repressible (SEQ ID N° 79),
pLYS4—lysine inducible or repressible (SEQ ID N° 80),
pLYS9—lysine inducible or repressible (SEQ ID N° 81),
pLYR1p—lysine inducible or repressible (SEQ ID N° 82),
pLYR2p—lysine inducible or repressible (SEQ ID N° 83),
pLYR3p—lysine inducible or repressible (SEQ ID N° 84),
pLYR4p—lysine inducible or repressible (SEQ ID N° 85),
pLYR5p—lysine inducible or repressible (SEQ ID N° 86),
pLYR6p—lysine inducible or repressible (SEQ ID N° 87),
pLYR7p—lysine inducible or repressible (SEQ ID N° 88),
pLYR8—lysine inducible or repressible (SEQ ID N° 89),
pLYR9—lysine inducible or repressible (SEQ ID N° 90),
pLYR10—lysine inducible or repressible (SEQ ID N° 91),
pLYR11—lysine inducible or repressible (SEQ ID N° 92),
pMET17—methionine inducible or repressible (SEQ ID N° 93),
pMET6—methionine inducible or repressible (SEQ ID N° 94),
pMET14—methionine inducible or repressible (SEQ ID N° 95),
pMET3—methionine inducible or repressible (SEQ ID N° 96),
pSAM1—methionine inducible or repressible (SEQ ID N° 97),
pSAM2—methionine inducible or repressible (SEQ ID N° 98),
pMDH2—glucose inducible or repressible (SEQ ID N° 35),
pJEN1—glucose inducible or repressible (SEQ ID N° 118),
pICL1—glucose inducible or repressible (SEQ ID N° 119),
pADH2—glucose inducible or repressible (SEQ ID N° 120), and
pMLS1—glucose inducible or repressible (SEQ ID N° 121).

According to this particular embodiment, the inducible or repressible promoter according of the invention can, independently, be selected from the group consisting of pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

The activity of these promoters is thus repressed by the increasing presence of methionine, copper, lysine or glucose as indicated above, and their activity increases, i.e. is induced, when the quantity of methionine, copper, lysine or glucose is reduced.

In a particular embodiment, inducible or repressible promoters according to the invention may be selected from the group comprising promoters inducible or repressible with copper, promoters inducible or repressible with glucose, promoters inducible or repressible with lysine, promoters inducible or repressible with methionine and promoters inducible or repressible with threonine.

In a more particular embodiment, the inducible or repressible promoter according to the invention can, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, pCHA1, pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

More particularly, said promoters, identical or different, may be preferably characterized by a sequence of nucleic acid selected from the group consisting of sequences having at least 80% identity with sequences SEQ ID NO: 24 to 98 and 116-121.

Synthetic promoters as described in Blazeck & Alper (2013) Biotechnol. J. 8 46-58 can also be used.

The strong, weak and inductible or repressible promoters of the invention can originate from any organism from the Saccharomycetes class and can in particular originate, independently, from an organism selected from the group consisting of *Saccharomyces cerevisiae, Saccharomyces boulardii, Saccharomyces castelii, Saccharomyces bayanus, Saccharomyces arboricola, Saccharomyces kudriavzevii, Ashbya gossypii, Kluveromyces lactis, Pichia pastoris, Candida glabrata, Candida tropicalis, Debaryomyces castelii, Yarrowia lipolitica* and *Cyberlindnera jadinii*.

The strong, weak and inductible or repressible promoters of the invention can preferably originate from an organism selected from the group consisting of *Saccharomyces cerevisiae, Saccharomyces castelii, Saccharomyces bayanus, Saccharomyces arboricola, Saccharomyces kudriavzevii* and *Kluveromyces lactis*.

Terminators

As it is disclosed herein, the expression of the genes of interest that have been genetically engineered for obtaining a recombinant yeast according to the invention comprise appropriate transcription terminator sequences that are functional in yeast cells, including in *Saccharomyces cerevisiae*.

Said transcription terminators, identical or different, may be found in literature Yamanishi et al., (2013) ACS synthetic biology 2, 337-347.

Terminators more particularly interesting in the present invention may be selected from the group comprising:
tTDH2 from the gene coding for Glyceraldehyde-3-phosphate dehydrogenase, isozyme 2 (TDH2 gene=Sequence SEQ ID N° 99),
tCYC1 (=Sequence SEQ ID N° 100),
tTDH3 (=Sequence SEQ ID N° 101), and
tADH1 from gene coding for the alcohol dehydrogenase (ADH1 gene=Sequence SEQ ID N° 102),
tADH2 from gene coding for the alcohol dehydrogenase (ADH2 gene=Sequence SEQ ID N° 103),
tTPI1 from the gene encoding for the Triose Phosphate Isomerase (TPI1 gene=Sequence SEQ ID N° 104), tMET17 from the gene encoding for the O-acetyl homoserine-O-acetyl serine sulfhydrylase (Met17 gene=Sequence SEQ ID N° 105),
tENO2 from the gene coding for Enolase II (ENO2 gene=Sequence SEQ ID N° 106),
tMET3 (=Sequence SEQ ID N° 107), and
tPGK1 from the gene encoding for the 3-phosphoglycerate kinase (PGK1 gene=Sequence SEQ ID N° 108),
tDIT1 (=Sequence SEQ ID N° 109)
tRPL3 (=Sequence SEQ ID N° 110)
tRPL41B (=Sequence SEQ ID N° 111)
tRPL15A (=Sequence SEQ ID N° 112)
tIDP1 (=Sequence SEQ ID N° 113).
More particularly, said terminator, identical or different, may be preferably characterized by a sequence of nucleic acid selected from the group consisting of sequences having at least 80% identity with sequences SEQ ID NO: 99 to 113.

Recombinant Yeast

Generally, yeast can grow rapidly and can be cultivated at higher density as compared with bacteria, and does not require an aseptic environment in the industrial setting. Furthermore, yeast cells can be more easily separated from the culture medium compared to bacterial cells, greatly simplifying the process for product extraction and purification.

Preferentially, the yeast of the invention may be selected among the genus Saccharomyces, CandidaAshbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus or Malassezia.

More preferentially, the yeast may be Crabtree positive yeast of genus of Saccharomyces, Dekkera, Schizosaccharomyces, Kluyveromyces, Torulaspora Zigosaccharomyces, or. Brettanomycces.

More preferentially, the yeast may be from the species Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa or Torulaspora glabrata.

More preferentially, the recombinant yeast may belong to the Saccharomyces genus, and preferably to the Saccharomyces cerevisiae species.

As above-mentioned, a recombinant yeast according to the invention has a pyruvate decarboxylase activity which is reduced by insertion of at least one DNA construct(s) selected from those disclosed in the present specification.

Methods implemented to insert a specific DNA construct within a gene belong to the general knowledge of a man skilled in the art. A related method is described in more details in the herein after examples.

Culture Conditions

The present invention also relates to the use of a recombinant yeast such as above-defined, for the production of ectoine.

The present invention further relates to a method of production of ectoine comprising the following steps:
providing a recombinant microorganism as previously described, cultivating the recombinant microorganism in a culture medium containing a source of carbon, and recovering the ectoine.

Typically, microorganisms of the invention are grown at a temperature in the range of about 20° C. to about 37° C., preferably at a temperature ranging from 27 to 34° C., in an appropriate culture medium.

When the recombinant yeast according to the invention belongs to the S. cerevisiae species, the temperature may advantageously range from 27 to 34° C., in an appropriate culture medium.

Suitable growth media for yeast are common commercially prepared media such as broth that includes yeast nitrogen base, ammonium sulfate, and dextrose as the carbon/energy source) or YPD Medium, a blend of peptone, yeast extract, and dextrose in optimal proportions for growing most. Other defined or synthetic growth media may also be used and the appropriate medium for growth of the particular microorganism will be known by one skilled in the art of microbiology or fermentation science.

The term "appropriate culture medium" is above-defined.

Examples of known culture media for a recombinant yeast according to the present invention are known to the person skilled in the art, and are presented in the following publication D. Burke et al., Methods in yeast Genetics—A cold spring harbor laboratory course Manual (2000).

Suitable pH ranges for the fermentation may be between pH 3.0 to pH 7.5, where pH 4.5 to pH 6.5 is preferred as the initial condition.

Fermentations may be performed under aerobic conditions or micro-aerobic conditions.

The amount of product in the fermentation medium can be determined using a number of methods known in the art, for example, high performance liquid chromatography (HPLC) or gas chromatography (GC).

The present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system may also be used in the present invention. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media.

Measurement of the actual substrate concentration in Fed-Batch systems is difficult and is therefore estimated on the basis of the changes of measurable factors such as pH, dissolved oxygen and the partial pressure of waste gases such as $CO_2$.

Fermentations are common and well known in the art and examples may be found in Sunderland et al., (1992), herein incorporated by reference. Although the present invention is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production.

In order to still improve the ectoine production, a particular embodiment may consist of culturing the recombinant yeast cells in an appropriate culture medium, such as above-mentioned, wherein the said culture medium comprises an optimal amount of carbon source, especially glucose.

Preferably, the cells are cultured in such an optimal culture medium during only a part of the whole culture duration. In some embodiments, the yeast cells are incubated in the said optimal culture medium 10 hours or more after initiation of the culture, which encompasses 11, 12, 13, 14, 15 or 16 hours or more after initiation of the culture.

Preferably, the cells are cultured in such an optimal culture medium during a time period ranging from 5 hours to 15 hours, which includes from 6 hours to 10 hours, e.g. 8 hours after initiation of the culture.

In preferred embodiments, the carbon source comprised in said optimal culture medium consists of glucose. In preferred embodiments, the said optimal culture medium comprises 12% w/w or more glucose, including 15% w/w or more glucose. In preferred embodiments, the said optimal culture medium comprises at most 40% w/w glucose, which includes at most 35% w/w glucose.

Thus, in the preferred embodiments described above, a method for producing ectoine according to the invention may further comprise, between steps (a) and (c), an intermediate step (b) consisting of cultivating the yeast cells in the said optimal culture medium.

Purification of Ectoine

According to a specific aspect of the invention, the fermentative production of ectoine comprises a step of isolation of the ectoine from the culture medium. Recovering the ectoine from the culture medium is a routine task for a man skilled in the art. It may be achieved by a number of techniques well known in the art including but not limiting to distillation, gas-stripping, pervaporation, selective precipitation or liquid extraction. The expert in the field knows how to adapt parameters of each technique dependent on the characteristics of the material to be separated.

The yeast as model of microorganism in the present invention has been retained in that the synthesized ectoine is/are entirely exported outside the cells, thus simplifying the purification process.

The synthesized ectoine may be collected by distillation. Distillation may involve an optional component different from the culture medium in order to facilitate the isolation of ectoine by forming azeotrope and notably with water. This optional component is an organic solvent such as cyclohexane, pentane, butanol, benzene, toluene, trichloroethylene, octane, diethylether or a mixture thereof.

Gas stripping is achieved with a stripping gas chosen among helium, argon, carbon dioxide, hydrogen, nitrogen or mixture thereof.

Liquid extraction is achieved with organic solvent as the hydrophobic phase such as pentane, hexane, heptane or dodecane.

The terms "between . . . and . . . " and "ranging from . . . to . . . " should be understood as being inclusive of the limits, unless otherwise specified.

The examples and figures which follow are presented by way of illustration and without implied limitation of the invention.

EXAMPLES

Example 1: Protocol for Making a Recombinant *Saccharomyces cerevisiae* Strain According to the Invention All the hereinafter implemented recombinant *Saccharomyces cerevisiae* strains were constructed from standard strains using standard yeast molecular genetics procedure (Methods in yeast Genetics—A cold spring harbor laboratory course Manual (2000) by D. Burke, D. Dawson, T. Stearns CSHL Press).

Cluster of the following-mentioned genes were integrated in recombinant yeast at once using the ability of yeast to efficiently recombine free DNA ends which have sequence homology.

In addition, for a better comprehension of following genotypes:
  ade2, his3, leu2, trp1 and ura3 are auxotrophy marker genes.
  Lowercase letters mean that the considered gene is inactive, uppercase letters reflect an active gene.
  "::": following a gene name means that the gene is interrupted by what follows (if more than one gene are inserted, they are noted in brackets [ ]). The interruption of the gene is concomitant with an entire deletion of the coding sequence but preserves the promoter. In consequence the gene followed by "::" is inactive and is noted in lowercase. If not specified the transcription of the gene inserted is controlled by the promoter of the disrupted gene.
  "gene.K1" means that the gene originates from *Kluyveromyces lactis*.

More particularly, the coding sequences to be cloned were artificially synthesized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotide sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit are then PCR amplified from the plasmids constructs, yielding X unit of linear DNA having overlapping sequences. At least one of this gene is an auxotrophic marker, in order to select for recombination event. All the linear fragments are transformed in the yeast at once, and recombinant yeast are selected for the auxotrophy related to the marker used. The integrity of the sequence is then verified by PCR and sequencing.

Example 2: Comparative Examples for the Production of Ectoine

A. Firstly, two recombinant strains are obtained: YA3370-20 and YA3371-46. These two strains have been recombined in order to only comprise a part of the modifications according to the invention.

Accordingly, these two strains are as follows:

YA3370-20: ade2, can1::[pACU1-AAT2-tRPL3-pCUP1-1-PPC-5.Ec-tTP11]x4, his3::[pACU5-HOM2-2-tRPL3-pTDH3-GDH-2.Eca-tIDP1]x4, hom6::[URA3-pCCW12-ECTB.He-tIDP1]x5, leu2, lyp1::[pPDC1-ECTA.He-tCYC1-pTDH3-ECTC.He-tTDH3]x2, pyk1::[LEU2.K1-RS,pTDH3-PEPCK-1.Ec-tIDP1,pTEF3-AQR1-tRPL41B, pCUR3-PYK1-tPYK1], sam3::[pPDC1-METX.Cg-tRPL3-pTDH3-MHPF.ec-tIDP1]x2, trp1::[pPDC1-PPC-5.Ec-tRPL3-pACU7-AK.Bs-tIDP1-TRP1]x6, ura3

YA3371-46: ade2, can1::[pACU1-AAT2-tRPL3-pCUP1-1-PPC-5.Ec-tTP11]x4, his3::[pACU5-HOM2-2-tRPL3-pTDH3-GDH-2.Eca-tIDP1]x4, hom6::[URA3-pCCW12-ECTB.He-tIDP1]x5, leu2, lyp1::[pPDC1-ECTA.He-tCYC1-pTDH3-ECTC.He-tTDH3]x2, pyk1::[LEU2.K1-RS,pTDH3-PEPCK-1.Ec-tIDP1,pTEF3-AQR1-tRPL41B, pCUR3-PYK1-tPYK1], sam3::[pCCW12-ECTB.Pa-tRPL3-pTDH3-MHPF.Ec-tRPL41B]x4, trp1::[pPDC1-PPC-5.Ec-tRPL3-pACU7-AK.Bs-tIDP1-TRP1]x6, ura3

PEPCK-1 is a form of PEPCK stabilized by modification of the Arginine amino acid in position 2 by a Glycine.

PPC-5 is a more stable form of PPC wherein an alanine has been added in N+1.

All these strains were grown for 24 hours in YE (Yeast Extract) 2% and Glucose 8%, and 500 µM of $CuSO_4$ was added after 8 hours. The content of ectoine in the medium was assayed after 24 hours using the AccQ-Tag precolumn derivatization method for amino acid determination using a AccQ-Tag Ultra Derivatization Kit from Waters as advised by the manufacturer.

The ectoine amounts obtained with these different strains are respectively:

YA3370-20: 1 g/L$^{-1}$.
YA3371-46: 1.55 g/L$^{-1}$.

In comparison, a native strain does not produce ectoine.

It results from this comparative experiment that a recombinant strain comprising the modifications according to the invention produces a greater amount of ectoine when cultured in the same conditions as other recombinant strains not comprising all the genetic modifications according to the invention.

B. Five other recombinant strains have also been obtained: YA3380-40B, YA3595-25 and YA3595-34.

These three strains are as follows:

YA3380-40B: gnp1::[LEU2.K1-RS, pADH1-AAT2-tRPL15A, pTEF3-MDH3-1-tRPL3, pPDC1-PEPCK-1.Ec-tMET25, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3::[pACU5-ME3.At-tRPL3-pACU6-METX-1.Cg-tIDP1]x11, hom6::[TRP1.K1, pCCW12.Sba-HOM3-tDIT1], leu2, mup3::[HIS5. Sp, pACU7-PEPCK-1.Ec-tRPL3, pCCW12-HOM2-1-tTDH3, pPGK1-AAT2-tTDH2, pENO2-MDH3-1-tRPL15A, pCUP1-1-GDH-2.Eca-tTPI1, pTDH3.Sba-ECTB.He-tIDP1, pPDC1-ECTA.He-tRPL41B, pTEF1.Sba-ECTC.He-tRPL15A], pyk1::[LEU2.K1, pTDH3-PEPCK-1.Ec-tIDP1, pPDC1-MDH3-1-tRPL15A, pTEF3-TP01-tEN02, pCUR3-PYK1-7-tCYC1], trp1, ura3

YA3595-25: ade2, gnp1::[LEU2.K1-RS,pADH1-AAT2-tRPL15A, pTEF3-MDH3-1-tRPL3, pPDC1-PEPCK-1.Ec-tMET25, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, hom6::[TRP1.K1, pCCW12.Sba-HOM3-tDIT1], leu2, mup3::[HIS5.Sp, pACU7-PEPCK-1.Ec-tRPL3, pCCW12-HOM2-1-tTDH3, pPGK1-AAT2-tTDH2, pEN02-MDH3-1-tRPL15A, pCUP1-1-GDH-2.Eca-tTPI1, pTDH3.Sba-ECTB.He-tIDP1, pPDC1-ECTA.He-tRPL41B, pTEF1.Sba-ECTC.He-tRPL15A], pyk1::[LEU2.K1, pTDH3-PEPCK-1.Ec-tIDP1, pPDC1-MDH3-1-tRPL15A, pTEF3-TP01-tEN02, pCUR3-PYK1-7-tCYC1], sam3::[pACU7-PEPCK-1.Ec-tRPL3-pCUP1-1-HOM3-tDIT1]x7, trp1, ura3::[pCCW12-ECTB.Ab-tRPL3-pTDH3-ECTC.He-tRPL41B.Sba]x14

YA3595-34: ade2, gnp1::[LEU2.K1-RS,pADH1-AAT2-tRPL15A, pTEF3-MDH3-1-tRPL3, pPDC1-PEPCK-1.Ec-tMET25, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, hom6::[TRP1.K1, pCCW12.Sba-HOM3-tDIT1], leu2, mup3::[HIS5.Sp, pACU7-PEPCK-1.Ec-tRPL3, pCCW12-HOM2-1-tTDH3, pPGK1-AAT2-tTDH2, pEN02-MDH3-1-tRPL15A, pCUP1-1-GDH-2.Eca-tTPI1, pTDH3.Sba-ECTB.He-tIDP1, pPDC1-ECTA.He-tRPL41B, pTEF1.Sba-ECTC.He-tRPL15A], pyk1::[LEU2.K1, pTDH3-PEPCK-1.Ec-tIDP1, pPDC1-MDH3-1-tRPL15A, pTEF3-TPO1-tEN02, pCUR3-PYK1-7-tCYC1], sam3::[pACU7-PEPCK-1.Ec-tRPL3-pCUP1-1-HOM3-tDIT1]x7, trp1, ura3::[pCCW12-ECTB.Ab-tRPL3-pTDH3-ECTC.He-tRPL41B.Sba]x9

The strains YA3380-40B and YA3595-25 were grown for 24 hours in YPA medium (1% yeast extract, 2% peptone, 0.01% adenine hemisulfate), Glucose 8%, $(NH_4)_2SO_4$ 50 mM, and Methionine 0.5 mM and Threonine 0.85 mM. The content of ectoine in the medium was assayed after 24 hours using the AccQ-Tag precolumn derivatization method for amino acid determination using a AccQ-Tag Ultra Derivatization Kit from Waters as advised by the manufacturer.

PEPCK-1 is a form of PEPCK stabilized by modification of the Arginine amino acid in position 2 by a Glycine.

The ectoine amounts obtained with these two strains are respectively:

YA3380-40B: 211 mg/L$^{-1}$.

YA3595-25: 1.29 g/L$^{-1}$.

In comparison, a native strain does not produce ectoine.

The strain YA3595-34, as well as the strain YA3595-25, were grown for 24 hours in YPA medium (1% yeast extract, 2% peptone, 0.01% adenine hemisulfate), Saccharose 8%, (NH$_4$)$_2$SO$_4$ 50 mM, and Methionine 0.5 mM and Threonine 0.85 mM. The content of ectoine in the medium was assayed after 24 hours using the AccQ-Tag precolumn derivatization method for amino acid determination using a AccQ-Tag Ultra Derivatization Kit from Waters as advised by the manufacturer.

The ectoine amounts obtained with these two strains are respectively:

YA3595-25: 2.63 g/L$^{-1}$.

YA3595-34: 2.58 g/L$^{-1}$.

In comparison, a native strain does not produce ectoine.

It results from this comparative experiment that a recombinant strain comprising the modifications according to the invention produces a greater amount of ectoine when cultured in the same conditions as other recombinant strains not comprising all the genetic modifications according to the invention.

C. Three other recombinant strains have also been obtained: YA4440, YA4442 and YA4444.

These three strains are as follows:

YA4440: MAT-α, gnp1::[LEU2.K1-RS, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3::[HIS3-pACU5-ME3.At-tRPL3, pACU6-METX-1.Cg-tIDP1]x5, hom6::[TRP1.K1-RS, pCCW12.Sba-HOM3-tDIT1], leu2, lys2Δ201, mup3::[HIS5.sp-RS, pACU7-PEPCK-1.Ec-tRPL3, pCCW12-HOM2-1-tTDH3, pPGK1-AAT2-tTDH2, pENO2-MDH3 tRPL15A, pCUP1-1-GDH-21.Eca-tTPI1, pTDH3.Sba-ECTB.He-tIDP1, pPDC1-ECTA.He-tRPL41B, pTEF1.Sba-ECTC.He-tRPL15A], pyk1::[LEU2.K1-RS, pTDH3-PEPCK-1.Ec-tIDP1, pPDC1-MDH3-1-tRPL15A, pTEF3-TPO1-tENO2, pCUR3-PYK1-7-tCYC1], sam3::[pACU7-PEPCK-1.Ec-tRPL3, pCUP1-1-HOM3-tDIT1-sam3]x5, trp1, trp4::[LYS2-loxP, pCCW12-PEPCK-1.Ec-tTPI1, pCCW12-GDH2-tRPL3, pCCW12-METX-1.Cg-tRPL41B.Sba, pCCW12.Sba-HOM3-tRPL15A], ura3::[ECTB.Ab-ECTC.He-URA3]x7

YA4442: MAT-α, gnp1::[LEU2.K1-RS, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3::[HIS3-pACU5-ME3.At-tRPL3, pACU6-METX-1.Cg-tIDP1]x5, hom6::[TRP1.K1-RS, pCCW12.Sba-HOM3-tDIT1], leu2, lys2Δ201, mup3::[HIS5.sp-RS, pACU7-PEPCK-1.Ec-tRPL3, pCCW12-HOM2-1-tTDH3, pPGK1-AAT2-tTDH2, pENO2-MDH3-1-tRPL15A, pCUP1-1-GDH-21.Eca-tTPI1, pTDH3.Sba-ECTB.He-tIDP1, pPDC1-ECTA.He-tRPL41B, pTEF1.Sba-ECTC.He-tRPL15A], pyk1::[LEU2.K1-RS, pTDH3-PEPCK-1.Ec-tIDP1, pPDC1-MDH3-1-tRPL15A, pTEF3-TPO1-tENO2, pCUR3-PYK1-7-tCYC1], sam3::[pACU7-PEPCK-1.Ec-tRPL3, pCUP1-1-HOM3-tDIT1-sam3]x5, trp1, trp4::[LYS2-loxP, pCCW12-PEPCK-1.Ec-tTPI1, pCCW12-GDH1-tRPL3, pCCW12-METX-1.Cg-tRPL41B.Sba, pCCW12.Sba-HOM3-tRPL15A], ura3::[ECTB.Ab-ECTC.He-URA3]x7

YA4444: MAT-α, gnp1::[LEU2.K1-RS, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3::[HIS3-pACU5-ME3.At-tRPL3, pACU6-METX-1.Cg-tIDP1]x5, hom6::[TRP1.K1-RS, pCCW12.Sba-HOM3-tDIT1], leu2, lys2Δ201, mup3::[HIS5.sp-RS, pACU7-PEPCK-1.Ec-tRPL3, pCCW12-HOM2-1-tTDH3, pPGK1-AAT2-tTDH2, pENO2-MDH3 tRPL15A, pCUP1-1-GDH-21.Eca-tTPI1, pTDH3.Sba-ECTB.He-tIDP1, pPDC1-ECTA.He-tRPL41B, pTEF1.Sba-ECTC.He-tRPL15A], pyk1::[LEU2.K1-RS, pTDH3-PEPCK-1.Ec-tIDP1, pPDC1-MDH3-1-tRPL15A, pTEF3-TPO1-tENO2, pCUR3-PYK1 tCYC1], sam3::[pACU7-PEPCK-1.Ec-tRPL3, pCUP1-1-HOM3-tDIT1-sam3]x5, trp1, trp4::[LYS2-loxP, pCCW12-PEPCK-1.Ec-tTPI1, pCCW12-GDH2.Eca-tRPL3, pCCW12-METX-1.Cg-tRPL41B.Sba, pCCW12.Sba-HOM3-tRPL15A], ura3::[ECTB.Ab-ECTC.He-URA3]x7

GDH1 and GDH2 are endogenous *Saccharomyces cerevisiae* enzymes, while GDH2.Eca is a GDH enzyme from Entodimium caudatum.

These strains were grown in Erlenmeyer flasks at 28° C. for 16 h in Yeast extract 2%, Sucrose 8%, Methionine 0.5 mM, Threonine 4.2 mM, Urea 50 mM, vitamin B5 4 μM, vitamin B1 6 μM, vitamin B6 10 μM, vitamin B10 1.5 μM, vitamin B3 2.9 μM, vitamin B2 0.5 μM, vitamin B8 0.08 μM, vitamin B9 4.5 nM, CuSO4 500 μM. After 16 hours 500 μM CuSO4 and urea 100 mM were added and the cultures were grown for another 8 hours.

Ectoine production was then evaluated essentially as described in Ono H, et al. (1999) Journal of Bacteriology, p, 91-99 except that ectoine was detected by HPLC-UV.

Under these conditions, YA4440 produced 6.4 g/l of ectoine, YA4442 produced 4.7 g/l of ectoine and YA4444 produced 6.1 g/l of ectoine. It is reminded that, in these same conditions, a wild-type strain (e.g. non recombinant) does not a produce a detectable amount of ectoine.

These three strains are identical but for the GDH enzyme over-expressed. The above results show that the over-expression of NADH dependent GDH (GDH2 in YA4440 and GDH2.Eca in YA4444) allows for the production of more ectoine than the overexpression of a NADPH dependent GDH (GDH1 in YA4442).

Thus, the overexpression of a NADH dependent glutamate Dehydrogenase allows for the production of more ectoine than the overexpression of a NADPH dependent glutamate Dehydrogenase (GDH1).

The invention claimed is:

1. An ectoine-producing recombinant yeast, in the genome of which:
   (A) (i) at least one nucleic acid encoding an aspartokinase is overexpressed and/or is under the control of an inducible or repressible promoter; and/or
   (ii) at least one nucleic acid encoding an aspartate kinase is overexpressed and/or is under the control of an inducible or repressible promoter; and
   (B) at least one nucleic acid encoding an aspartate semi-aldehyde dehydrogenase that can use as coenzyme both NAD and NADP is overexpressed and/or is under the control of an inducible or repressible promoter; and
   (C) at least one nucleic acid encoding a diaminobutyrate aminotransferase is overexpressed and/or is under the control of an inducible or repressible promoter; and
   (D) (i) at least one nucleic acid encoding an homoserine-O-acetyltransferase METX is overexpressed and/or is under the control of an inducible or repressible promoter that is heterologous from the nucleic acid encoding METX, and
   (ii) at least one nucleic acid encoding a diaminobutyric acid acetyltransferase is overexpressed and/or is under the control of an inducible or repressible promoter; and
   (E) at least one nucleic acid encoding an ectoine synthase is overexpressed and/or is under the control of an inducible or repressible promoter; and
   (F) (i) at least one endogenous nucleic acid encoding an homoserine dehydrogenase has been deleted and/or interrupted, and/or (ii) at least one nucleic acid encoding a homoserine dehydrogenase is:
under the control of an inducible or repressible promoter;
under the control of a weak promoter; and/or
the homoserine dehydrogenase is degron-tagged.

2. The recombinant yeast according to claim 1, in the genome of which at least one nucleic acid encoding an aspartate transaminase is overexpressed and/or is under the control of an inducible or repressible promoter.

3. The recombinant yeast according to claim 1, in the genome of which at least one nucleic acid encoding a glutamate dehydrogenase that converts oxo-glutarate to glutamate is overexpressed and/or is under the control of an inducible or repressible promoter.

4. The recombinant yeast according to claim 1, in the genome of which at least one of the following modifications has been performed:
(A) at least one endogenous nucleic acid encoding a general amino acid permease AGP3 have been deleted from the genome of the yeast, and:
   (i) at least one nucleic acid encoding a general amino acid permease AGP3 has been inserted and is under the control of an inducible or repressible promoter, and/or
   (ii) at least one nucleic acid encoding a destabilized general amino acid permease AGP3 has been inserted, wherein the general amino acid permease AGP3 is degron-tagged;
(B) at least one endogenous nucleic acid encoding a branched-chain amino-acid permease 3 has been deleted from the genome of the yeast, and:
   (i) at least one nucleic acid encoding a branched-chain amino-acid permease 3 has been inserted and is under the control of an inducible or repressible promoter, and/or
   (ii) at least one nucleic acid encoding a destabilized branched-chain amino-acid permease 3 has been inserted, wherein the branched-chain amino-acid permease 3 is degron-tagged;
(C) at least one endogenous nucleic acid encoding a branched-chain amino-acid permease 2 has been deleted from the genome of the yeast, and:
   (i) at least one nucleic acid encoding a branched-chain amino-acid permease 2 has been inserted and is under the control of an inducible or repressible promoter, and/or
   (ii) at least one nucleic acid encoding a destabilized branched-chain amino-acid permease 2 has been inserted, wherein the branched-chain amino-acid permease 2 is degron-tagged;
(D) at least one endogenous nucleic acid encoding a general amino acid permease GAP1 has been deleted from the genome of the yeast, and:
   (i) at least one nucleic acid encoding a general amino acid permease GAP1 has been inserted and is under the control of an inducible or repressible promoter, and/or
   (ii) at least one nucleic acid encoding a destabilized general amino acid permease GAP1 has been inserted, wherein the general amino acid permease GAP1 is degron-tagged;
(E) at least one endogenous nucleic acid encoding a high-affinity glutamine permease GNP1 has been deleted from the genome of the yeast, and:
   (i) at least one nucleic acid encoding a high-affinity glutamine permease GNP1 has been inserted and is under the control of an inducible or repressible promoter, and/or
   (ii) at least one nucleic acid encoding a destabilized high-affinity glutamine permease GNP1 has been inserted, wherein the high-affinity glutamine permease GNP1 is degron-tagged;
(F) at least one endogenous nucleic acid encoding a general amino acid permease AGP1 has been deleted from the genome of the yeast, and:
   (i) at least one nucleic acid encoding a general amino acid permease AGP1 has been inserted and is under the control of an inducible or repressible promoter, and/or
   (ii) at least one nucleic acid encoding a destabilized general amino acid permease AGP1 has been inserted, wherein the general amino acid permease AGP1 is degron-tagged;
(G) at least one endogenous nucleic acid encoding a low-affinity methionine permease MUP3 has been deleted from the genome of the yeast, and:
   (i) at least one nucleic acid encoding a low-affinity methionine permease MUP3 has been inserted and is under the control of an inducible or repressible promoter, and/or
   (ii) at least one nucleic acid encoding a destabilized low-affinity methionine permease MUP3 has been inserted, wherein the low-affinity methionine permease MUP3 is degron-tagged;
(H) at least one endogenous nucleic acid encoding a high-affinity methionine permease MUP1 has been deleted from the genome of the yeast, and:
   (i) at least one nucleic acid encoding a high-affinity methionine permease MUP1 has been inserted and is under the control of an inducible or repressible promoter, and/or
   (ii) at least one nucleic acid encoding a destabilized high-affinity methionine permease MUP1 has been inserted, wherein the high-affinity methionine permease MUP1 is degron-tagged;
(I) at least one nucleic acid encoding a transporter AQR1 is overexpressed; and/or
(J) at least one nucleic acid encoding a polyamine transporter 1 is overexpressed.

5. The recombinant yeast according to claim 4, in the genome of which at least two of the modifications indicated in claim 4 have been performed.

6. The recombinant yeast according to claim 4, wherein the at least one nucleic acid encoding a general amino acid permease, a branched-chain amino-acid permease 3, a branched-chain amino-acid permease 2, a general amino acid permease GAP1, a high-affinity glutamine permease GNP1, a general amino acid permease AGP1, a low-affinity methionine permease MUP3 and a high-affinity methionine permease MUP1 are, independently, nucleic acid from a yeast.

7. The recombinant yeast according to claim 1, wherein the nucleic acid encoding an aspartokinase is nucleic acid from a yeast.

8. The recombinant yeast according to claim 1, wherein the nucleic acid encoding an homoserine-O-acetyltransferase METX is nucleic acid from a bacterium.

9. The recombinant yeast according to claim 1, wherein at least one of the overexpressed nucleic acid is under the control of a strong promoter.

10. The recombinant yeast according to claim 1, wherein all of the inducible or repressible promoters are, independently, selected from the group consisting of promoters inducible or repressible with copper, promoters inducible or repressible with methionine and promoters inducible or repressible with threonine.

11. The recombinant yeast according to claim 1, wherein the weak promoter is, independently, selected from the group consisting of pURA3, pRPLA1, pNUP57 and pGAP1.

12. The recombinant yeast according to claim 1, wherein all of the inducible or repressible promoters are, independently, selected from the group consisting of promoters inducible or repressible with copper, promoters inducible or repressible with lysine and promoters inducible or repressible with methionine.

13. The recombinant yeast according to claim 1, in the genome of which at least one nucleic acid encoding an homoserine-O-acetyltransferase MET2 is overexpressed and/or is under the control of an inducible or repressible promoter.

14. Method for producing ectoine, said method comprising the steps of:
    (a) culturing a recombinant yeast as defined in claim 1 in a culture medium; and
    (b) recovering the ectoine from said culture medium.

15. Method according to claim 14, wherein the culture medium comprises at least a carbon source.

* * * * *